United States Patent [19]
Goodearl

[11] Patent Number: 5,882,893
[45] Date of Patent: Mar. 16, 1999

[54] NUCLEIC ACIDS ENCODING MUSCARINIC RECEPTORS AND USES THEREFOR

[75] Inventor: Andrew D.J. Goodearl, Natick, Mass.

[73] Assignee: Millennium Pharmaceuticals, Inc., Cambridge, Mass.

[21] Appl. No.: 985,090

[22] Filed: Dec. 4, 1997

[51] Int. Cl.⁶ .................................... C12N 15/12
[52] U.S. Cl. ................ 435/69.1; 435/252.3; 435/254.11; 435/320.1; 435/325; 536/24.31; 536/23.5
[58] Field of Search .................................... 435/69.1, 325, 435/252.3, 254.11, 320.1; 536/23.5, 24.31

[56] References Cited

PUBLICATIONS

Akiba, I. et al., "Primary Structure of Porcine Muscarinic Acetylcholine Receptor III and Antagonist Binding Studies," *FEBS Lett.*, vol. 235, No. 1–2, 257–61 (1988).
Allard, W.J. et al., "Sequence of the Gene Encoding the Human M1 Muscarinic Acetylcholine Receptor," *Nucleic Acids Res.*, vol. 15, No. 24, 10604 (1987).
Arden, J.R. et al., "Mutational Analysis of Third Cytoplasmic Loop Domains in G–protein Coupling of the HM1 Muscarinic Receptor," *Biochem. Biophys. Res. Commun.*, vol. 188, No. 3, 1111–5 (1992).
Bartels, J. et al., "Human Dermal Fibroblasts Express Eotaxin: Molecular Cloning, mRNA Expression, and Identification of Eotaxin Sequence Variants," *Biochemical and Biophysical Research Communications*, vol. 225, 1045–1051 (1996).
Bonner, T.I. et al., "Cloning and Expression of the Human and Rat m5 Muscarinic Acetylcholine Receptor Genes," *Neuron*, vol. 1, No. 5, 403–10 (1988).
Bonner, T.I. et al., "Identification of a Family of Muscarinic Acetylcholine Receptor Genes," *Science*, vol. 237, 527–32 (1987).
Braun, T. et al., A Novel Subtype of Muscarinic Receptor Identified by Homology Screening, *Biochem. Biophys. Commun.*, vol. 149, No. 1, 125–32 (1987).
Chapman, C.G. and Browne, M.J., "Isolation of the Human ml (Hml) Muscarinic Acetycholine Receptor Gene by PCR Amplification," *Nucleic Acids Res.*, vol. 18, No. 8, 2191 (1990).
Gadbut, A.P. and Galper, J.B., "A Novel $M_3$ Muscarinic Acetylcholine Receptor is Expressed in Chick Atrium and Ventricle," *J. Biol. Chem.*, vol. 269, No. 41, 25823–9 (1994).
Herrera, L. et al., "Cloning of a *Xenopus laevis* Muscarinic Receptor Encoded by an Intronless Gene," *FEBS Lett.*, vol. 352, No. 2, 175–9 (1994).
Himmelreich, R. et al., "Complete Sequence Analysis of the Genome of the Bacterium *Mycoplasma pneumoniae*," *Nucleic Acids Res.*, vol. 24, No. 22, 4420–49 (1996).
Kubo, T. et al., "Cloning, Sequencing and Expression of Complementary DNA Encoding the Muscarinic Acetylcholine Receptor," *Nature*, vol. 323, No. 6087, 411–6 (1986).
Kubo, T. et al., "Primary Structure of Porcine Cardiac Muscarinic Acetylcholine Receptor Deduced from the cDNA Sequence," *FEBS Lett.*, vol. 209, No. 2, 367–72 (1986).

Kurtenbach, E. et al., "Muscarinic Acetylcholine Receptors. Peptide Sequencing Identifies Residues Involved in Antagonist Binding and Disulfide Bond Formation," *J. Biol. Chem.*, vol. 265, No. 23, 13702–8 (1990).
Lai, J. et al., "Amplification of the Rat m2 Muscarinic Receptor Gene by the Polymerase Chain Reaction: Functional Expression of the $M_2$ Muscarinic Receptor," *Life Sci.*, vol. 47, No. 12, 1001–13 (1990).
Lai, J. et al., "The Molecular Properties of the $M_1$ Muscarinic Receptor and its Regulation of Cytosolic Calcium in a Eukaryotic Gene Expression System," *Adv. Exp. Med. Biol.*, vol. 287, 313–30 (1991).
Lee, P.H. et al., "Cloning and Expression of a cDNA Encoding Bovine Muscarinic Acetylcholine m3 Receptor," *Biochim. Biophys. Acta*, vol. 1223, No. 1, 151–4 (1994).
Liao, C.F. et al., "Molecular Cloning and Expression of a Fifth Muscarinic Acetylcholine Receptor," *J. Biol. Chem.*, vol. 264, No. 13, 7328–37 (1989).
Miles, J.S. et al., "Close Linkage of the Human Cytochrome P45011A and P45011B Gene Subfamilies: Implications for the Assignment of Substrate Specificity," *Nucleic Acids Res.*, vol. 17, No. 8, 2907–17 (1989).
Peralta, E.G. et al., "Distinct Primary Structures, Ligand–Binding Properties and Tissue–Specific Expression of Four Human Muscarinic Acetylcholine Receptors," *EMBO J.*, vol. 6, No. 13, 3923–9 (1987).
Peralta, E.G. et al., "Primary Structure and Biochemical Properties of an $M_2$ Muscarinic Receptor," *Science*, vol. 236, No. 4801, 600–5 (1987).
Phillips, I.R. et al., "Isolation and Sequence of a Human Cytochrome P–450 cDNA Clone," *PNAS*, vol. 82, No. 4, 983–7 (1985).
Savarese, T.M.et al., "Site–directed Mutagenesis of the Rat $m_1$ Muscarinic Acetylcholine Receptor. Role of Conserved Cysteines in Receptor Function," *J. Biol. Chem.*, vol. 267, No. 16, 11439–48 (1992).

(List continued on next page.)

*Primary Examiner*—Sally P. Teng
*Attorney, Agent, or Firm*—Lahive & Cockfield, LLP; Amy E. Mandragouras

[57] ABSTRACT

The invention provides isolated nucleic acids molecules, designated muscarinic acetylcholine receptor 6 ("mACHR-6") nucleic acid molecules, which encode polypeptides involved in the modulation of acetylcholine responses in acetylcholine responsive cells. The invention also provides antisense nucleic acid molecules, expression vectors containing mACHR-6 nucleic acid molecules, host cells into which the expression vectors have been introduced, and non-human transgenic animals in which an mACHR-6 gene has been introduced or disrupted. The invention still further provides isolated mACHR-6 polypeptides, fusion polypeptides, antigenic peptides, and anti-mACHR-6 antibodies. Diagnostic, screening, and therapeutic methods utilizing compositions of the invention are also provided.

19 Claims, 13 Drawing Sheets

PUBLICATIONS

Shapiro, R.A. et al., "Isolation, Sequence, and Functional Expression of the Mouse M1 Muscarinic Acetylcholine Receptor Gene," *J. Biol. Chem.*, vol. 263, No. 34, 18397–403 (1988).

Tietje, K.M. and Nathanson, N.M., "Embryonic Chick Heart Expresses Multiple Muscarinic Acetylcholine Receptor Subtypes. Isolation and Characterization of a Gene Encoding a Novel m2 Muscarinic Acetylcholine Receptor with High Affinity for Pirenzepine," *J. Biol. Chem.*, vol. 266, vol. 26, 17382–7 (1991).

Tietje, K.M. et al., "Cloning and Functional Analysis of a Gene Encoding a Novel Muscarinic Acetylcholine Receptor Expressed in Chick Heart and Brain," *J. Biol. Chem.*, vol. 265, No. 5, 2828–34 (1990).

van Koppen, C.J. et al., "Isolation, Sequence and Functional Expression of the Mouse m4 Muscarinic Acetylcholine Receptor Gene," *Biochim. Biophys. Acta*, vol. 1173, No. 3, 342–4 (1993).

Wess, J. et al., "Role of Conserved Threonine and Tyrosine Residues in Acetylcholine Binding and Muscarinic Receptor Activation. A Study with m3 Muscarinic Receptor Point Mutants," *J. Biol. Chem.*, vol. 267, No. 27, 19313–9 (1992).

Wess, J. et al., "Site–directed Mutagenesis of the m3 Muscarinic Receptor: Identification of a Series of Threonine and Tyrosine Residues Involved in Agonist but not Antagonist Binding," *EMBO J.*, vol. 10, No. 12, 3729–34 (1991).

Yamano, S. et al., "The CYP2A3 Gene Product Catalyzes Coumarin 7–hydroxylation in Human Liver Microsomes," *Biochemistry*, vol. 29, No. 5, 1322–9 (1990).

FIG. 1A

```
                                                                                          79
GTCGACCCACGCGTCCGCGCACCGGGCAGCGGCTCAGGCTCCGGCTGCAGCAGCCGCTGCCGGCCCC

158
ACTGGGCTCGGATCCGGCCCCCTCGGCACCCGCCCCCGCCTGCTCTGGCCCCGGAGCCCCGGGGAACCCGGACCATGCGCTGG

237
GCGCCCCCAGGGGAACCCGGCCAAGGGCCCGCCAAAGACGAGGCTCCCGGGGCCCCTCCCGGCGCCCAG 6 308
CTCTCGGCCGGCCCCTGCCCCGTCCCGGAGCCGCGTGAGCCTGCGGGGCC ATG GAG CGC GCG CCG CCC
                                                      M   E   R   A   P   P

D   G   P   L   N   A   S   G   A   L   A   G   E   A   A   A   G   G   A             26
GAC GGG CCG AAC GCT TCG GGG GCG CTG GCG GGC GAG GCG GCG GCG GGG GGG GCG             368

R   G   F   S   A   A   W   T   A   V   L   M   A   L   L   I   V                     46
CGC GGC TTC TCG GCA GCC TGG ACC GCG GTG CTC ATG GCG CTG CTC ATC GTG                     428

A   T   V   L   G   N   A   L   V   M   L   A   F   V   A   D   S   S   L   R         66
GCC ACG GTG CTG GGC AAC GCG CTG GTC ATG CTC GCC TTC GTG GCC GAC TCG AGC CTC CGC         488

T   Q   N   N   F   F   L   Y   P   Y   V   G   L   F   L   V   G   R   G   A   F     86
ACC CAG AAC AAC TTC CTG CTC AAC TAC GTG CTG CTG TTC CTC GTC GGC CGG GGC GCC TTC         548

C   I   P   L   W   L   V   D   Y   L   T   C   T   S   S   A   F   N   I   V   L    106
TGC ATC CCA CTG TGG CTG GTA GAC TAC CTG ACC TGC ACC TCC TCT GCC TTC AAC ATC GTG CTC    608

C   K   L   S   Y   D   R   F   L   S   V   T   R   A   V   S   Y   R   A   Q   Q    126
TGC AAG CTG TCG TAC GAC CGC TTC CTG TCG GTC ACC CGA GCG GTC TCA TAC CGG GCC CAG CAG    668

L   I   S   Y                                                                         146
CTC ATC AGC TAC                                                                        728
```

FIG. 1B

```
G   D   T   R   R   A   V   L   M   L   V   W   V   L   A   F   L   L   166
GGT GAC ACG CGG CGG GCA GTG CTG AAG ATG CTG GTG TGG GTG CTG GCC TTC CTG CTG 788

Y   G   P   A   I   L   S   W   E   Y   L   S   G   G   S   I   P   E   G   186
TAC GGA CCA GCC ATC CTG AGC TGG GAG TAC CTG TCC GGG GGC AGC TCC ATC CCC GAG GGC 848

H   C   Y   A   E   F   F   Y   N   W   Y   L   I   T   A   S   T   L   E   206
CAC TGC TAT GCC GAG TTC TTC TAC AAC TGG TAC CTC ATC ACG GCT TCC ACC CTG GAG 908

F   F   T   P   F   L   S   V   T   F   F   N   L   Y   I   N   Q   226
TTC TTT ACG CCC TTC CTC AGC GTC ACC TTC TTT AAC CTC TAC ATC AAC ATC CAG 968

R   R   T   R   L   R   L   D   G   A   R   E   A   A   G   P   E   P   P   246
AGG CGC ACC CGC CTC CGG CTG GAT GGG GCT CGA GAG GCA GCC GGC CCC GAG CCC CCT CCC 1028

E   A   Q   P   S   P   P   P   P   P   G   C   W   G   K   G   H   266
GAG GCC CAG CCC TCA CCA CCC CCG CCT GGC TGC TGG GGC AAG GGG CAC 1088

E   A   M   P   L   H   R   Y   G   V   G   E   A   V   A   S   P   A   286
GAG GCC ATG CCG CTG CAC AGG TAT GGG GTG GGT GAG GCC GTA GGC GCT GAG GCC 1148

G   E   A   T   L   G   G   G   G   G   S   V   S   P   T   S   306
GGG GAG GCG ACC CTC GGG GGT GGG GGC GGC TCC GTG GCT TCA CCC ACC TCC AGC 1208

G   S   S   R   G   T   E   R   P   R   S   L   K   R   G   S   K   P   326
TCC GGC AGC TCC TCG AGG GGC ACT GAG AGG CCG CGC TCA CTC AAG AGG GGC TCC AAG CCG 1268
```

FIG.1C

```
      S    A    S    S    A    L    E    K    R    M    K    M    V    S    Q    S    F    T    Q    346
     TCG  GCG  TCC  TCG  GCC  TCA  CTG  GAG  AAG  CGC  ATG  AAG  ATG  GTG  TCC  CAG  TTC  ACC  CAG 1328

R    F    R    L    S    R    D    R    K    V    A    K    S    I    V    A    C    H    I    366
     CGC  TTT  CGG  CTG  TCT  CGG  GAC  AGG  AAA  GTG  GCC  AAG  TCG  ATC  GTC  GCC  TGC  ATC  AGC  ATC 1388

F    G    L    C    W    A    P    Y    T    L    M    I    R    A    A    C    H    G    386
     TTT  GGG  CTC  TGC  TGG  GCC  CCA  TAC  ACG  CTG  ATG  ATC  CGG  GCC  GCC  TGC  CAT  GGC 1448

H    C    V    P    D    Y    W    Y    E    T    S    F    W    L    L    W    A    N    S    A    406
     CAC  TGC  GTC  CCT  GAC  TAC  TGG  TAC  GAA  ACC  TCC  TTC  TGG  CTC  CTG  TGG  GCC  AAC  TCG  GCT 1508

V    N    P    V    L    Y    P    L    C    H    S    F    R    R    A    F    T    K    L    426
     GTC  AAC  CCT  GTC  CTC  TAC  CCT  CTG  TGC  CAC  AGC  TTC  CGC  CGG  GCC  TTC  ACC  AAG  CTG 1568

L    C    P    Q    P    K    L    K    I    Q    P    H    S    L    E    H    C    W    K    *    446
     CTC  TGC  CCC  CAG  CCC  AAG  CTC  AAA  ATC  CAG  CCC  CAC  AGC  TCC  CTG  GAG  CAC  TGC  TGG  AAG  TGA 1628

GTGGCCCACCAGAGAGCCTCCCTCAGCCCACGCCTCTCTCTCAGCCCAGTGTCTCCTGGCATCTGCGCCCTGCCCCCTACCC 1707

GGCTCGTTCCCCAGGGGTGAGCCCCGCCGTGTCTGTGGCCCTCTCTTAATGCCACGGCAGCCACCCTGCCATGGAGGC 1786

GCCTTCCTGGGTTGGCCAGAGGGCCCCCTCACTGGCTGGAGGCTGGTGGCCGGCCCCTGCCCCCCACATTCTGGC 1865

TCCACCGGGAGGACAGTCTGGAGGTCCCAGACATGCTGCCCACCCCTTCGCAGTTACTGTT 1944

GGTGTTCTTCCCAAAGCAAGCACCTGGGTGTGCTCCAGCAGTTGCCTCTGCACGTGCACACACC 2023
```

FIG.1D

```
TGCACACCCCTGCACACACCTGCACACCGTCCCCTCCCCCGGACAAGCCCCAGGACACTGCCTTTGCTGCCTTCTGTCTC 2102
TTGCATAAGCCTCAGGCCTGGCCCCTTTCACCCCTCTTCCACCAACTCTCTGCCCCCAAAAGTGTCAAGGGCCCTA 2181
GGAACCTCGAAGCTGTTCTCTGCTTTTCCATTCTGGGTGTTTTCAGAAAGATGAAGAAGAAAACATGTCTGTGAACTTG 2260
ATGTTCCTGGGATGTTTAATCAAGAGACAAAATTGCTGAGGAGCTCAGGGCTGGATTGGCAGGTGTGGGCTCCCACG 2339
CCCTCCTCCCCTCCGTAAGGCTTCCGGCTGTGCCAGCTGTCTGCCCACCCCGCCTCTGGGCTCACACCAGCC 2418
CTGGTGGCCAAGCCTGCCCCGGCCACTCTGTTTGCTCACCCAGGACCCTCGGGGTTGTTGGGAGGAGGGCCCGGCT 2497
GGGCCCGAGGGTCCCAAGGCGTGCAGGGGGTCCAGAGGAGGTGCCCGGGGCCAGGGGCGCTTCGCCATGTGCTGTGCA 2576
CCCGTGCCACGCGCTCTGCATGCTCCTCTGCCTGCCCGCTGCCCTGCAAACCGTGAGGTCACAATAAAGTGT 2655
ATTTTTTAAAAAAAAAAAAAAAAGGGCGGCCGC 2689
```

FIG. 2A

| V | P | Y | V | L | T | G | R | W | T | F | G | A | F | C | I | P | L | Y | 8 |
|---|---|---|---|---|---|---|---|---|---|---|---|---|---|---|---|---|---|---|---|
| GTA | CCC | TAT | GTG | CTG | ACC | GGC | CGT | TGG | ACC | TTC | GGC | GCC | TTC | TGC | ATC | CCA | TTG | TAC | 24 |

| V | D | Y | L | C | R | A | S | V | F | G | R | L | C | K | L | W | L | 28 |
|---|---|---|---|---|---|---|---|---|---|---|---|---|---|---|---|---|---|---|
| GTG | GAC | TAC | CTA | TGT | CGA | GCC | TCC | GTC | TTC | GGC | CGG | GGC | CTC | TGC | AAG | CTG | TGG | CTG | 84 |

| R | F | L | S | V | T | R | A | V | W | G | S | V | F | N | A | Q | L | I | D | 48 |
|---|---|---|---|---|---|---|---|---|---|---|---|---|---|---|---|---|---|---|---|---|
| CGA | TTC | CTG | TCA | GTC | ACT | CGA | GCT | GTC | TGG | GGC | AGT | GTC | TTC | AAC | GCC | CAG | CTC | ATC | GAC | 144 |

| A | V | K | M | A | L | V | W | G | G | S | I | S | A | Y | R | D | T | Y | R | 68 |
|---|---|---|---|---|---|---|---|---|---|---|---|---|---|---|---|---|---|---|---|---|
| GCC | GTT | AAG | ATG | GCA | CTG | GTG/TGG | GGT | GGC | TCT | GGT | ATC | TCC | GCC | TAC | AGG | GAC | ACG | TAT | AGA | CGG | 204 |

| L | S | W | E | Y | L | S | G | I | S | A | F | R | L | Y | G | P | Y | A | I | 88 |
|---|---|---|---|---|---|---|---|---|---|---|---|---|---|---|---|---|---|---|---|
| CTG | AGT | TGG | GAG | TAC | CTG | TCT | GGC | ATC | TCG | GCC | TTC | AGG | CTG | TAT | GGG | CCT | TAT | GCT | ATC | 264 |

| F | F | Y | N | W | Y | L | F | I | S | A | L | Y | C | H | C | E | T | P | F | E | 108 |
|---|---|---|---|---|---|---|---|---|---|---|---|---|---|---|---|---|---|---|---|---|---|
| TTC | TTC | TAC | AAC | TGG | TAC | CTG | TTT | ATC | TCC | GCC | CTC | TAC | TGC | CAC | TGC | GAG | ACC | TAT | CCC | TTC | 324 |

| S | V | T | F | F | N | L | Y | L | S | A | I | Q | R | R | T | R | L | 128 |
|---|---|---|---|---|---|---|---|---|---|---|---|---|---|---|---|---|---|---|
| CTC | AGC | GTT | ACC | TTC | TTC | AAC | CTC | TAC | CTG | AGC | ATC | TAC | CAG | AGG | CGC | ACC | CGC | CTT | 384 | 148 / 444 |

FIG. 2B

```
R   L   D   G   G   R   E   A   G   P   P   E   P   P   D   A   Q   P   P   S   P              168
CGG CTT GAT GGG GGC CGT GAG GCT GGC CCA GAA CCC CCA GAT GCC CAG CCC TCG CCA              504

P   P   A   P   P   S   C   W   G   G   C   W   P   K   G   H   E   A   A   M   P              188
CCT CCA GCT CCC CCC AGC TGC TGG GGC TGC TGG CCA AAA GGG CAT GAG GCC GCC ATG CCG              564

L   H   R   Y   G   V   G   E   A   A   G   P   V   E   A   E   A   L              208
TTG CAC AGG TAT GGG GTG GGT GAG GCA GCA GGC CCT GTT GAG GCT GAG GCC CTC              624

G   G   G   S   G   G   A   A   S   P   T   S   S   P   S   S   S              228
GGG GGT GGC AGT GGT GGA GGT GCT GCC TCG CCC ACC TCC AGC TCC AGC TCA              684

R   G   T   E   R   P   R   S   L   K   R   G   K   P   S   A   S   A              248
AGG GGC ACT GAG AGG CCA CGC TCA CTC AAA AGG GGC AAG CCA TCT TCA GCA              744

S   L   E   K   R   M   K   M   V   S   Q   I   T   R   F   R   L   S              268
TCC CTG GAG AAG CGC ATG AAG ATG GTG TCC CAG AGC ACC CAG TTC CGG CTG TCG              804

R   D   K   K   V   A   K   S   L   A   I   I   V   S   I   F   G   L   C   W              288
CGG GAC AAG AAG GTG GCC AAG TCG CTG GCC ATC ATC GTG AGC ATC TTT GGG CTC TGC TGG              864

A   P   Y   T   L   L   M   I   R   A   C   H   G   R   C   I   P   D              308
GCG CCG TAC ACG CTC CTA ATG ATC CGA GCT TGC CAT GGC CGC TGC ATC CCC GAT              924

Y   W   Y   E   T   S   F   W   L   L   W   A   N   S   A   V   N   P   V   L              328
TAC TGG TAC GAG ACG TCC TTC TGG CTT CTG TGG GCC AAC TCG GCC GTC AAC CCC GTC CTC              984
```

FIG.2C

```
 Y   P   L   C   H   Y   S   F   R   R   A   F   T   K   L   L   C   P   Q   K                348
TAC CCA CTG TGC CAC TAC AGC TTC CGC AGA GCC TTC ACC AAG CTC CTC TGC CCC CAG AAG               1044

L   K   V   Q   P   H   G   S   L   E   Q   C   W   K   *                                    363
CTC AAG GTC CAG CCC CAC GGC TCC CTG GAG CAG TGC TGG AAG TGA                                   1089

GCAGCTGCCCCACCCTTCTGAGGCCAGGCCCTTGTACTTGTTTGAGTGGGCAGCCGGAGCGTGGGCGGGCCCTGGTCC                1168

ATGCTCCGCTCCAAATGCCATGGCGGCCTCTTAGATCATCAACCCCGCAGTGGGTAGCATGGCAGTGGGCCAAGAGC                1247

CCTAGTTGGTGGAGCTAGAGTGTGTGCTGGTTAGCTCTCTGCCGCCACATTCTCCTTCACCACACAGAAGACAATCCAGGA            1326

GTCCCAGGCATGCCTTCCACCTACACACACACACACACACACACACACAGTGCAGTGCCAGTGATGTC                          1405

CCCTTTTGCATATTTAGTGGTTGGTGTCCTCCCTAATGCAAACCTCGGTGTGCTCCCGGCCCTGCAATGC                       1484
```

FIG.2D

```
GTGCGTGCGCCCTGCATGTGCTCACACCCGCCACACACTTGCAACACCTCCTCTCCCAGAAG      1563
AGCTGGGACGATGCCCTTTGCTGCCACTGTCTCTTGCTTAATCCCAGAGCCTGGCTCCTTATCCCCCACTCTCCCTTC    1642
AACTCTGCCCCACAAAGTGTCGAGCGCCTCGGGAAACTTGAAGCTTCTCTGCTCCTTCCACTCTGGATGTTTCAGGAA    1721
GATGGAGGAGAAGAAAACACGTCTGTGAACTTGATGTTCCTTGGATGTTTAATCAAGAGAGACAAAATTGCCGAGGAGC   1800
TCGGGGCTGGATTGGCCAGGTGTGGGCTCCCACGCCCCTCCCCCTCAGTGCTGCAGCTTCCGGCTGCGAGCCGCCAGCTG  1879
CTTCTGCCTGCCCCGCCCAGGCTTGGGACGATGGCCCCTGCTTGCCCCGTCTGTACAATCAGAATTGGGGGT          1958
GGGTGGTTATGGGGTAGAGCGGCTCTTCACTGTGCCCTAAAGGTCCTGAGGCTCACAGGACAGTCAGGAGAGCAGG      2037
CAGGCCCGCGACACCTGGAGGAATGCTTGCCTCGTCCTGTGTACTCACCTCAGGCTTCTGCAATGCTCTGCTGCCCTT    2116
GTGCCCTGGTGTGCTGCCTCTGCCAATGTGAAAACACAATAAAGTGTATTTTTTAAAAAAAAAAAAAAAAAAA         2195
AAAAAAAAAAAAAGGGCGGCCGC                                                           2218
```

FIG.3A

```
                                                                                                        79
GTCGACCCACGCGTCCGGGCGGTGAGAGCGGGCTGGCGCGCAGCCAAGAACCCTTTAAGCCAAGAAAAAGCTTTCT

E   G   R   L   S   N   S   K   G   A   F   C   I   P   L   Y               16
CGGTTTTAAGCTGA GAA GGG AGG CTG TCC AAC AGC AAG GGT GCC TTC TGC ATC CCA TTG TAC   142

V   P   Y   V   L   T   G   R   W   T   F   G   R   G   L   C   K   L   W   L   36
GTA CCC TAT GTG CTG ACC GGC CGT TGG ACC TTC GGC CGG GGC CTC TGC AAG CTG TGG CTG  202

V   V   D   Y   L   L   C   A   S   S   V   F   N   I   V   L   I   S   Y   D   56
GTG GTA GAC TAC CTA CTG TGT GCC TCG TCC GTC TTC AAC ATC GTA CTC ATC AGC TAT GAC  262

R   F   L   S   V   T   R   A   V   S   Y   R   A   Q   Q   G   D   T   R   R   76
CGA TTC CTG TCA GTC ACT CGA GCT GTC TCC TAC AGG GCC CAG CAG GGG GAC ACG AGA CGG  322

A   V   R   K   M   A   L   V   W   V   L   A   F   L   L   Y   G   P   A   I   96
GCC GTT CGG AAG ATG GCA CTG GTG TGG GTG CTG GCC TTC CTG CTG TAT GGG CCT GCC ATC  382
```

FIG.3B

| | | | | | | | | | | | 116 |
|---|---|---|---|---|---|---|---|---|---|---|---|
| L | S | W | E | Y | L | S | G | G | S | I | P | E | G | H | C | Y | A | E | 116 |
| CTG | AGT | TGG | GAG | TAC | CTG | TCT | GGT | GGC | AGT | TCC | ATC | CCC | GAG | GGC | CAC | TGC | TAT | GCT | GAG | 442 |

| F | F | Y | N | W | Y | F | L | I | S | A | T | L | E | F | F | T | P | F | 136 |
| TTC | TTC | TAC | AAC | TGG | TAC | TTT | CTC | ATC | TCG | GCC | ACC | CTC | GAG | TTC | TTC | ACG | CCC | TTC | 502 |

| L | S | V | T | F | F | N | L | I | Y | L | N | I | Q | R | R | T | R | L | 156 |
| CTC | AGC | GTT | ACC | TTC | TTC | AAC | CTC | AGC | ATC | TAC | CTG | AAC | ATC | CAG | AGG | CGC | ACC | CGC | CTT | 562 |

| R | L | D | G | G | R | S | A | E | P | E | P | P | D | A | Q | P | S | P | 176 |
| CGG | CTT | GAT | GGG | GGC | CGT | AGC | GCT | GAG | CCA | GAA | CCC | CCA | GAT | GCC | CAG | CCC | TCG | CCA | 622 |

| P | A | P | S | C | W | C | W | P | K | G | H | G | E | R | E | A | M | P | 196 |
| CCT | CCA | GCT | CCC | CCC | AGC | TGC | TGG | TGG | CCA | AAA | GGG | CAT | GGC | GAG | GAG | GCC | ATG | CCG | 682 |

| L | H | R | Y | G | V | G | E | A | G | P | G | V | E | A | G | E | A | L | 216 |
| TTG | CAC | AGG | TAT | GGG | GTG | GGT | GAG | GCA | GGC | CCT | GGT | GTT | GAG | GCT | GGG | GAG | GCT | GCC | CTC | 742 |

FIG. 3C

```
  G   G   G   S   G   G   G   A   A   A   S   P   T   S   S   S   S   S   S    236
GGG GGT GGC AGT GGT GGA GGT GCT GCT GCC TCG CCC ACC TCC AGC TCT TCT AGC TCC TCA   802

R   G   T   E   R   P   R   S   L   K   R   G   S   K   P   S   A   S   A    256
AGG GGC ACT GAG AGG CCA CGC TCA CTC AAA AGG GGC TCC AAG CCA TCA GCA TCA GCA       862

S   L   E   K   R   M   K   M   V   S   Q   I   T   Q   R   F   R   L   S    276
TCC CTG GAG AAG CGC ATG AAG ATG GTG TCC CAG AGC ATC ACC CAG CGC TTC CGG CTG TCG   922

R   D   K   K   V   A   K   S   L   A   I   V   S   I   F   G   L   C   W    296
CGG GAC AAG AAG GTG GCC AAG TCG CTG GCC ATC ATC GTG AGC ATC TTT GGG CTC TGC TGG   982

A   P   Y   T   L   L   M   I   I   R   A   A   C   H   G   R   C   I   P   D    316
GCG CCG TAC ACG CTC CTC CTA ATG ATC CGA GCT GCT TGC CAT GGC CGC TGC ATC CCC GAT   1042

Y   W   Y   E   T   S   F   W   L   L   W   A   N   S   A   V   N   P   V   L    336
TAC TGG TAC GAG ACG TCC TTC TGG CTT CTG TGG GCC AAC TCG GCC GTC AAC CCC GTC CTC   1102
```

FIG. 3D

```
 Y   P   L   C   H   Y   S   F   R   R   A   F   T   K   L   L   C   P   Q   K      356
TAC CCA CTG TGC CAC TAC AGC TTC CGC AGA GCC TTC ACC AAG CTC CTC TGC CCC CAG AAG     1162

L   K   V   Q   P   H   G   S   L   E   Q   C   W   K   *                          371
CTC AAG GTC CAG CCC CAC GGC TCC CTG GAG CAG TGC TGG AAG TGA                         1207

GCAGCTGCCCCACCCTTCTGAGGCCAGGCCCTTGTACTTGTTTGAGTGGGCAGCCGGAGCGTGGGCGGGCCCTGGTCC     1286

ATGCTCCGCTCCAAATGCCATGGGCCTCTTAGATCATCAACCCCGCAGTGGGTAGCATGGCAGGTGGGCCAAGAGC      1365

CCTAGTTGGTGGAGCTAGAGTGTGCTGGTTAGCTCTGCCGCCACATTCTCCTTCACCACAGAAGAGACAATCCAGGA     1444

GTCCCAGGCATGCCTTCCACCTACACACACACACACACACACACACAGTGCCAGTGATGTC                     1523

CCCTTTTGCATATTTAGTGGTTGGTGTCCTCCCTAATGCAAACCTCGGTGTGTGTCCCGGCCTCCGGCCCTGGCAATGC   1602

GTGCGTGCGCCCTGCATGTGCTCACACCCGCCCACACACCGCCCACACACTTGCAACACCTCCTCTCCCAGAAG        1681
```

FIG.3E

```
AGCTGGGGACGATGCCCTTTGCTGCCACTGTCTCTTGCTTAATCCCAGAGCCTGGCTCCTTATCCCCCACTCTCCCTTC    1760
AACTCTGCCCCACAAAGTGTCGAGCGCCTCGGGAAACTTGAAGCTTCTCTGCTCCTTCCACTCTGGATGTTTTCAGGAA    1839
GATGGAGGAGAGAAAACACGTCTGTGAACTTGATGTTCCTTGGATGTTTAATCAAGAGAGACAAAATTGCCGAGGAGC    1918
TCGGGGCTGGATTGGCAGGTGTGGGCTCCCACGCCCTCCTCCCCTCAGTGCTGCAGCTTCCGGCTGAGCCGCGCCAGCTG    1997
CTTCTGCCCTGCCCCCCAGGCTTGGGACGATGGCCCCTGCTTGCCCCGTCTGTACAATCAGAATTTGGGGGT    2076
GGGTGGTTATGGGGTAGAGCGGCTCTTCACTGTGCCCTAAAGGTCCTGAGGCTCACAGGACAGTCAGCAGGAGAGCAGG    2155
CAGGCCCCGCGACACCTGGGAGGAATGCTTTGCCTCCTCGTGTACTCACCTCAGGCTTCTGCATGCTCTGCTGCCCTT    2234
GTGCCCTGGTGTGCTGCCTCTGCCAATGTGAAAACACAATAAAGTGTATTTTTTAAAAAAAAAAAAAAAAAAAA    2313
AAAAAAAAAAAAGGGGCGGCCGC
```

NUCLEIC ACIDS ENCODING MUSCARINIC RECEPTORS AND USES THEREFOR

BACKGROUND OF THE INVENTION

Muscarinic receptors, so named because the actions of acetylcholine on such receptors are similar to those produced by the mushroom alkaloid muscarine, mediate most of the inhibitory and excitatory effects of the neurotransmitter acetylcholine in the heart, smooth muscle, glands and in neurons (both presynaptic and postsynaptic) in the autonomic and the central nervous system (Eglen, R. and Watson, N. (1996) *Pharmacology & Toxicology* 78:59–68). The muscarinic receptors belong to the G protein-coupled receptor superfamily (Wess, J. et al. (1990) *Comprehensive Medicinal Chemistry* 3:423–491). Like all other G protein-coupled receptors, the muscarinic receptors are predicted to conform to a generic protein fold consisting of seven hydrophobic transmembrane helices joined by alternative intracellular and extracellular loops, an extracellular amino-terminal domain, and a cytoplasmic carboxyl-terminal domain. The mammalian muscarinic receptors display a high degree of sequence identity, particularly in the transmembrane domains, sharing approximately 145 invariant amino acids (Wess, J. (1993) *TIPS* 14:308–313). Moreover, all of the mammalian muscarinic receptors contain a very large third cytoplasmic loop which, except for the membrane-proximal portions, displays virtually no sequence identity among the different family members (Bonner, T. I. (1989) *Trends Neurosci.* 12:148–151). Ligand binding to the receptor is believed to trigger conformational changes within the helical bundle, which are then transmitted to the cytoplasmic domain, where the interaction with specific G proteins occurs.

Molecular cloning studies have revealed the existence of five molecularly distinct mammalian muscarinic receptor proteins, termed the $M_1$–$M_5$ receptors (Bonner, T. I. (1989) *Trends Neurosci.* 12:148–151; and Hulme, E. C. et al. (1990) *Annu. Rev. Pharmacol. Toxicol.* 30:633–673). The $M_1$ receptor is expressed primarily in the brain (cerebral cortex, olfactory bulb, olfactory tubercle, basal forebrain/septum, amygdala, and hippocampus) and in exocrine glands (Buckley, N. J. et al. (1988) *J. Neurosci.* 8:4646–4652). The $M_2$ receptor is expressed in the brain (olfactory bulb, basal forebrain/septum, thalamus and amygdala), and in the ileum and the heart. The $M_3$ receptor is expressed in the brain (cerebral cortex, olfactory tubercle, thalamus and hippocampus) the lung, the ileum, and in exocrine glands. The $M_4$ receptor is expressed in the brain (olfactory bulb, olfactory tubercle, hippocampus and striatum) and in the lung. Finally, the $M_5$ receptor is expressed primarily in the brain (substantia nigra) (Hulme, E. C. et al. (1990) *A. Rev. Pharmac. Toxic.* 30:633–673).

The two enzymes with which muscarinic receptors interact most directly are adenylate cyclase and phospholipase C. Studies with cloned receptors have shown that the $M_1$, $M_3$, and $M_5$ muscarinic receptors are coupled to the types of G proteins known as Go (a stimulatory protein linked to phospholipase C) or Gq and that their activation results in the activation of phospholipase C. The $M_2$ and $M_4$ muscarinic receptors are coupled to a Gi protein (an inhibitory protein linked to adenylate cyclase), and their activation results in the inhibition of adenylate cyclase. Through these signal transduction pathways, the muscarinic receptors are responsible for a variety of physiological functions including the regulation of neurotransmitter release (including acetylcholine release) from the brain, the regulation of digestive enzyme and insulin secretion in the pancreas, the regulation of amylase secretion by the parotid gland, and the regulation of contraction in cardiac and smooth muscle (Caulfield, M. P. (1993) *Pharmac. Ther.* 58:319–379).

SUMMARY OF THE INVENTION

This invention provides a novel nucleic acid molecule which encodes a polypeptide, referred to herein as muscarinic acetylcholine receptor 6 ("mACHR-6") polypeptide or protein, which is capable of, for example, modulating the effects of acetylcholine on acetylcholine responsive cells e.g., by modulating phospholipase C signaling/activity. Nucleic acid molecules encoding an mACHR-6 polypeptide are referred to herein as mACHR-6 nucleic acid molecules. In a preferred embodiment, the mACHR-6 polypeptide interacts with (e.g., binds to) a protein which is a member of the G family of proteins. Examples of such proteins include Go, Gi, Gs, Gq and Gt. These proteins are described in Lodish H. et al. Molecular Cell Biology, (Scientific American Books Inc., New York, N.Y., 1995); Dolphin A. C. et al. (1987) *Trends Neurosci.* 10:53; and Birnbaumer L. et al. (1992) *Cell* 71:1069, the contents of which are expressly incorporated herein by reference.

In a preferred embodiment, the mACHR-6 polypeptide interacts with (e.g., binds to) acetylcholine. Acetylcholine is the predominant neurotransmitter in the sympathetic and parasympathetic preganglionic synapses, as well as in the parasympathetic postganglionic synapses and in some sympathetic postganglionic synapses. Synapses in which acetylcholine is the neurotransmitter are called cholinergic synapses. Acetylcholine acts to regulate smooth muscle contraction, heart rate, glandular function such as gastric acid secretion, and neural function such as release of neurotransmitters from the brain. The mACHR-6 polypeptide of the present invention binds to acetylcholine and serves to mediate the acetylcholine induced signal to the cell. Thus, mACHR-6 molecules can be used as targets to modulate acetylcholine induced functions and thus to treat disorders associated with, for example, abnormal acetylcholine levels, or abnormal or aberrant mACHR-6 polypeptide activity or nucleic acid expression.

Accordingly, one aspect of the invention pertains to isolated nucleic acid molecules (e.g., cDNAs) comprising a nucleotide sequence encoding an mACHR-6 polypeptide or biologically active portions thereof, as well as nucleic acid fragments suitable as primers or hybridization probes for the detection of mACHR-6-encoding nucleic acid (e.g., mRNA). In particularly preferred embodiments, the isolated nucleic acid molecule comprises the nucleotide sequence of SEQ ID NO:1 or 4, the nucleotide sequence of the DNA insert of the plasmid deposited with ATCC as Accession Number 98902, or the coding region or a complement of either of these nucleotide sequences. In other particularly preferred embodiments, the isolated nucleic acid molecule of the invention comprises a nucleotide sequence which encodes naturally occurring allelic variants, genetically altered variants and non-human and non-rat homologues of the mACHR-6 polypeptides described herein. Such nucleic acid molecules are identifiable as being able to hybridize to or which are at least about 60–65%, preferably at least about 70–75%, more preferably at least about 80–85%, and even more preferably at least about 90–95% or more homologous to the nucleotide sequence shown in SEQ ID NO:1 or 4, the nucleotide sequence of the DNA insert of the plasmid deposited with ATCC as Accession Number 98902, or a portion of either of these nucleotide sequences. In other preferred embodiments, the isolated nucleic acid molecule encodes the amino acid sequence of SEQ ID NO:2 or 5 or an amino acid sequence encoded by the nucleotide sequence of the DNA insert of the plasmid deposited with ATCC as Accession Number 98902. The preferred mACHR-6 polypeptides of the present invention also preferably possess at least one of the mACHR-6 activities described herein.

In another embodiment, the isolated nucleic acid molecule encodes a polypeptide or portion thereof wherein the polypeptide or portion thereof includes an amino acid sequence which is sufficiently homologous to an amino acid sequence of SEQ ID NO:2 or 5, e.g., sufficiently homologous to an amino acid sequence of SEQ ID NO:2 or 5 such that the polypeptide or portion thereof maintains an mACHR-6 activity. Preferably, the polypeptide or portion thereof encoded by the nucleic acid molecule maintains the ability to modulate an acetylcholine response in an acetylcholine responsive cell. In one embodiment, the polypeptide encoded by the nucleic acid molecule is at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the amino acid sequence of SEQ ID NO:2 or 5 (e.g., the entire amino acid sequence of SEQ ID NO:2 or 5) or the amino acid sequence encoded by the nucleotide sequence of the DNA insert of the plasmid deposited with ATCC as Accession Number 98902. In another preferred embodiment the nucleic acid molecule encodes a polypeptide fragment comprising at least 15 contiguous amino acids of SEQ ID NO:2 or 5. In yet another preferred embodiment, the polypeptide is a full length human polypeptide which is substantially homologous to the entire amino acid sequence of SEQ ID NO:2 or 5 (encoded by the open reading frame shown in SEQ ID NO:3 or 6, respectively). In still another preferred embodiment, the nucleic acid molecule encodes a naturally occurring allelic variant of the polypeptide of SEQ ID NO:2 or 5 and hybridizes under stringent conditions to a nucleic acid molecule comprising the nucleotide sequence of SEQ ID NO:1 or 4, respectively.

In yet another embodiment, the isolated nucleic acid molecule is derived from a human and encodes a portion of a polypeptide which includes a transmembrane domain. Preferably, the transmembrane domain encoded by the human nucleic acid molecule is at least about 50–55%, preferably at least about 60–65%, more preferably at least about 70–75%, even more preferably at least about 80–85%, and most preferably at least about 90–95% or more homologous to any of the human transmembrane domains (i.e., amino acid residues 34–59, 109–130, 152–174, 197–219, or 396–416) of SEQ ID NO:2 which are shown as separate sequences designated SEQ ID NOs:7, 9, 10, 11, and 13, respectively, or to any of the rat transmembrane domains (i.e., amino acid residues 1–8, 26–47, 69–91, 114–136, 277–297, or 313–333) of SEQ ID NO:5 which are shown as separate sequences designated SEQ ID NOs:14, 15, 16, 17, 18, and 19, respectively. More preferably, the transmembrane domain encoded by the human nucleic acid molecule is at least about 75–80%, preferably at least about 80–85%, more preferably at least about 85–90%, and most preferably at least about 90–95% or more homologous to the transmembrane domain (i.e., amino acid residues 360–380) of SEQ ID NO:2 which is shown as a separate sequence designated SEQ ID NO: 12, or at least about 80–85%, more preferably at least about 85–90%, and most preferably at least about 90–95% or more homologous to the transmembrane domain (i.e., amino acid residues 73–91) of SEQ ID NO:2 which is shown as a separate sequence designated SEQ ID NO:8.

In another preferred embodiment, the isolated nucleic acid molecule is derived from a human and encodes a polypeptide (e.g., an mACHR-6 fusion polypeptide such as an mACHR-6 polypeptide fused with a heterologous polypeptide) which includes a transmembrane domain which is at least about 75% or more homologous to SEQ ID NO:7–13, or to the corresponding rat sequences shown as SEQ ID NOs: 14–20 and has one or more of the following mACHR-6 activities: 1) it can interact with (e.g., bind to) acetylcholine; 2) it can interact with (e.g., bind to) a G protein or another protein which naturally binds to mACHR-6; 3) it can modulate the activity of an ion channel (e.g., a potassium channel or a calcium channel); 4) it can modulate cytosolic ion, e.g., calcium, concentration; 5) it can modulate the release of a neurotransmitter, e.g., acetylcholine, from a neuron, e.g., a presynaptic neuron; 6) it can modulate an acetylcholine response in an acetylcholine responsive cell (e.g., a smooth muscle cell or a gland cell) to, for example, beneficially affect the acetylcholine responsive cell, e.g., a neuron; 7) it can signal ligand binding via phosphatidylinositol turnover; and 8) it can modulate, e.g., activate or inhibit, phospholipase C activity.

In another embodiment, the isolated nucleic acid molecule is at least 15 nucleotides, e.g., at least 15 contiguous nucleotides, in length and hybridizes under stringent conditions to a nucleic acid molecule comprising the nucleotide sequence of SEQ ID NO:1 or 4 or the nucleotide sequence of the DNA insert of the plasmid deposited with ATCC as Accession Number 98902. Preferably, the isolated nucleic acid molecule corresponds to a naturally-occurring nucleic acid molecule. More preferably, the isolated nucleic acid encodes naturally-occurring human mACHR-6 or a biologically active portion thereof. Moreover, given the disclosure herein of an mACHR-6-encoding cDNA sequence (e.g., SEQ ID NO:1 or 4), antisense nucleic acid molecules (e.g., molecules which are complementary to the coding strand of the mACHR-6 cDNA sequence) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce an mACHR-6 polypeptide by culturing the host cell in a suitable medium. If desired, the mACHR-6 polypeptide can then be isolated from the medium or the host cell.

Yet another aspect of the invention pertains to transgenic non-human animals in which an mACHR-6 gene has been introduced or altered. In one embodiment, the genome of the non-human animal has been altered by introduction of a nucleic acid molecule of the invention encoding mACHR-6 as a transgene. In another embodiment, an endogenous mACHR-6 gene within the genome of the non-human animal has been altered, e.g., functionally disrupted, by homologous recombination.

Still another aspect of the invention pertains to an isolated mACHR-6 polypeptide or a portion, e.g., a biologically active portion, thereof. In a preferred embodiment, the isolated mACHR-6 polypeptide or portion thereof can modulate an acetylcholine response in an acetylcholine responsive cell. In another preferred embodiment, the isolated mACHR-6 polypeptide or portion thereof is sufficiently homologous to an amino acid sequence of SEQ ID NO:2 or 5 such that the polypeptide or portion thereof maintains the ability to modulate an acetylcholine response in an acetylcholine responsive cell.

In one embodiment, the biologically active portion of the mACHR-6 polypeptide includes a domain or motif, preferably a domain or motif which has an mACHR-6 activity. The domain can be transmembrane domain. If the active portion of the polypeptide which comprises the transmembrane domain is isolated or derived from a human, it is preferred that the transmembrane domain be at least about 75–80%, preferably at least about 80–85%, more preferably at least about 85–90%, and most preferably at least about 90–95% or more homologous to SEQ ID NO:7, 8, 9, 10, 11, 12, 13, 14, 15, 16, 17, 18, 19, or 20. Preferably, the biologically active portion of the mACHR-6 polypeptide which includes a transmembrane domain also has one of the following mACHR-6 activities: 1) it can interact with (e.g., bind to) acetylcholine; 2) it can interact with (e.g., bind to) a G protein or another protein which naturally binds to mACHR-6; 3) it can modulate the activity of an ion channel (e.g., a potassium channel or a calcium channel); 4) it can modulate cytosolic ion, e.g., calcium, concentration; 5) it can modulate the release of a neurotransmitter, e.g., acetylcholine, from a neuron, e.g., a presynaptic neuron; 6) it can modulate an acetylcholine response in an acetylcholine responsive cell (e.g., a smooth muscle cell or a gland cell) to, for example, beneficially affect the acetylcholine responsive cell, e.g., a neuron; 7) it can signal ligand binding via phosphatidylinositol turnover; and 8) it can modulate, e.g., activate or inhibit, phospholipase C activity.

The invention also provides an isolated preparation of an mACHR-6 polypeptide. In referred embodiments, the mACHR-6 polypeptide comprises the amino acid sequence of SEQ ID NO:2 or 5 or an amino acid sequence encoded by the nucleotide sequence of the DNA insert of the plasmid deposited with ATCC as Accession Number 98902. In another preferred embodiment, the invention pertains to an isolated full length polypeptide which is substantially homologous to the entire amino acid sequence of SEQ ID NO:2 or 5 (encoded by the open reading frame shown in SEQ ID NO:3 or 6, respectively) such as a naturally occurring allelic variant of the mACHR-6 polypeptides described herein. In yet another embodiment, the polypeptide is at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the entire amino acid sequence of SEQ ID NO:2 or 5 such as a non-human or non-rat homologue of the mACHR-6 polypeptides described herein. In other embodiments, the isolated mACHR-6 polypeptide comprises an amino acid sequence which is at least about 30–40% or more homologous to the amino acid sequence of SEQ ID NO:2 or 5 and has an one or more of the following mACHR-6 activities: 1) it can interact with (e.g., bind to) acetylcholine; 2) it can interact with (e.g., bind to) a G protein or another protein which naturally binds to mACHR-6; 3) it can modulate the activity of an ion channel (e.g., a potassium channel or a calcium channel); 4) it can modulate cytosolic ion, e.g., calcium, concentration; 5) it can modulate the release of a neurotransmitter, e.g., acetylcholine, from a neuron, e.g., a presynaptic neuron; 6) it can modulate an acetylcholine response in an acetylcholine responsive cell (e.g., a smooth muscle cell or a gland cell) to, for example, beneficially affect the acetylcholine responsive cell, e.g., a neuron; 7) it can signal ligand binding via phosphatidylinositol turnover; and 8) it can modulate, e.g., activate or inhibit, phospholipase C activity.

Alternatively, the isolated mACHR-6 polypeptide can comprise an amino acid sequence which is encoded by a nucleotide sequence which hybridizes, e.g., hybridizes under stringent conditions, or is at least about 60–65%, preferably at least about 70–75%, more preferably at least about 80–85%, and even more preferably at least about 90–95% or more homologous to the nucleotide sequence of SEQ ID NO:1 or 4 or the nucleotide sequence of the DNA insert of the plasmid deposited with ATCC as Accession Number 98902, such as the allelic variants and non-human and non-rat homologues of the mACHR-6 polypeptides described herein as well as genetically altered variants generated by recombinant DNA methodologies. It is also preferred that the preferred forms of mACHR-6 also have one or more of the mACHR-6 activities described herein.

The mACHR-6 polypeptide (or protein) or a biologically active portion thereof can be operatively linked to a non-mACHR-6 polypeptide (e.g., a polypeptide comprising heterologous amino acid sequences) to form a fusion polypeptide. In addition, the mACHR-6 polypeptide or a biologically active portion thereof can be incorporated into a pharmaceutical composition comprising the polypeptide and a pharmaceutically acceptable carrier.

The mACHR-6 polypeptide of the invention, or portions or fragments thereof, can be used to prepare anti-mACHR-6 antibodies. Accordingly, the invention also provides an antigenic peptide of mACHR-6 which comprises at least 8 amino acid residues of the amino acid sequence shown in SEQ ID NO:2 or 5 and encompasses an epitope of mACHR-6 such that an antibody raised against the peptide forms a specific immune complex with mACHR-6. Preferably, the antigenic peptide comprises at least 10 amino acid residues, more preferably at least 15 amino acid residues, even more preferably at least 20 amino acid residues, and most preferably at least 30 amino acid residues. The invention further provides an antibody that specifically binds mACHR-6. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for modulating a cell activity mediated by mACHR-6, e.g., biological processes mediated by phosphatidylinositol turnover and signaling; secretion of a molecule, e.g., a neurotransmitter from a brain cell, or an enzyme from a gland cell; or contraction of a smooth muscle cell, e.g., an ileum smooth muscle cell or a cardiac cell, e.g., a cardiomyocyte. Such methods include contacting the cell with an agent which modulates mACHR-6 polypeptide activity or mACHR-6 nucleic acid expression such that an mACHR-6-mediated cell activity is altered relative to the same cellular activity which occurs in the absence of the agent. In a preferred embodiment, the cell (e.g., a smooth muscle cell or a neural cell) is capable of responding to acetylcholine through a signaling pathway involving an mACHR-6 polypeptide. The agent which modulates mACHR-6 activity can be an agent which stimulates mACHR-6 polypeptide activity or mACHR-6 nucleic acid expression. Examples of agents which stimulate mACHR-6 polypeptide activity or mACHR-6 nucleic acid expression include small molecules, active mACHR-6 polypeptides, and nucleic acids encoding mACHR-6 that have been introduced into the cell. Examples of agents which inhibit mACHR-6 activity or expression include small molecules, antisense mACHR-6 nucleic acid molecules, and antibodies that specifically bind to mACHR- 6. In a preferred embodiment, the cell is present within a subject and the agent is administered to the subject.

The present invention also pertains to methods for treating subjects having various disorders, e.g., disorders mediated by abnormal mACHR-6 polypeptide activity, such as conditions caused by over, under, or inappropriate expression of mACHR-6. For example, the invention pertains to methods for treating a subject having a disorder characterized by aberrant mACHR-6 polypeptide activity or nucleic acid expression such as a nervous system disorder, e.g., a cognitive disorder, a sleep disorder, a movement disorder, a schizo-effective disorder, a disorder affecting pain generation mechanisms, a drinking disorder, or an eating disorder; a smooth muscle related disorder, e.g., irritable bowel syndrome, a cardiac muscle related disorder, e.g., bradycardia, or a gland related disorder, e.g., xerostomia. These methods include administering to the subject an mACHR-6 modulator (e.g., a small molecule) such that treatment of the subject occurs.

In other embodiments, the invention pertains to methods for treating a subject having a disorder mediated by abnormal mACHR-6 polypeptide activity, such as conditions caused by over, under, or inappropriate expression of mACHR-6, e.g., a nervous system disorder, e.g., a cognitive disorder, a sleep disorder, a movement disorder, a schizo-effective disorder, a disorder affecting pain generation mechanisms, a drinking disorder, or an eating disorder; a smooth muscle related disorder, e.g., irritable bowel syndrome; a cardiac muscle related disorder, e.g., bradycardia; or a gland related disorder, e.g., xerostomia. The method includes administering to the subject an mACHR-6 polypeptide or portion thereof such that treatment occurs. A nervous system disorder, smooth muscle related disorder, cardiac muscle related disorder or a gland related disorder can also be treated according to the invention by administering to the subject having the disorder a nucleic acid encoding an mACHR-6 polypeptide or portion thereof such that treatment occurs.

The invention also pertains to methods for detecting naturally occurring and recombinantly created genetic mutations in an mACHR-6 gene, thereby determining if a subject with the mutated gene is at risk for (or is predisposed to have) a disorder characterized by aberrant or abnormal mACHR-6 nucleic acid expression or mACHR-6 polypeptide activity, e.g., a nervous system disorder, a smooth muscle related disorder, a cardiac muscle related disorder or a gland related disorder. In preferred embodiments, the methods include detecting, in a sample of cells from the subject, the presence or absence of a genetic mutation characterized by an alteration affecting the integrity of a gene encoding an mACHR-6 polypeptide, or the misexpression of the mACHR-6 gene, such as that caused by a nucleic acid base substitution, deletion or addition, or gross sequence changes caused by a genetic translation, inversion or insertion.

Another aspect of the invention pertains to methods for detecting the presence of mACHR-6, or allelic variants thereof, in a biological sample. In a preferred embodiment, the methods involve contacting a biological sample (e.g., a brain or smooth muscle cell sample) with a compound or an agent capable of detecting mACHR-6 polypeptide or mACHR-6 mRNA such that the presence of mACHR-6 is detected in the biological sample. The compound or agent can be, for example, a labeled or labelable nucleic acid probe capable of hybridizing to mACHR-6 mRNA or a labeled or labelable antibody capable of binding to mACHR-6 polypeptide. The invention further provides methods for diagnosis of a subject with, for example, a nervous system disorder, a smooth muscle related disorder, a cardiac muscle related disorder or a gland related disorder, based on detection of mACHR-6 polypeptide or mRNA. In one embodiment, the method involves contacting a cell or tissue sample (e.g., a brain or smooth muscle cell sample) from the subject with an agent capable of detecting mACHR-6 polypeptide or mRNA, determining the amount of mACHR-6 polypeptide or mRNA expressed in the cell or tissue sample, comparing the amount of mACHR-6 polypeptide or mRNA expressed in the cell or tissue sample to a control sample and forming a diagnosis based on the amount of mACHR-6 polypeptide or mRNA expressed in the cell or tissue sample as compared to the control sample. Preferably, the cell sample is a brain cell sample. Kits for detecting mACHR-6 in a biological sample which include agents capable of detecting mACHR-6 polypeptide or mRNA are also within the scope of the invention.

Still another aspect of the invention pertains to methods, e.g., screening assays, for identifying a compound, e.g., a test compound, for treating a disorder characterized by aberrant mACHR-6 nucleic acid expression or polypeptide activity, e.g., a nervous system disorder, a smooth muscle related disorder, a cardiac muscle related disorder or a gland related disorder. These methods typically include assaying the ability of the compound or agent to modulate the expression of the mACHR-6 gene or the activity of the mACHR-6 polypeptide thereby identifying a compound for treating a disorder characterized by aberrant mACHR-6 nucleic acid expression or polypeptide activity. In a preferred embodiment, the method involves contacting a biological sample, e.g., a cell or tissue sample, e.g., a brain or smooth muscle cell sample, obtained from a subject having the disorder with the compound or agent, determining the amount of mACHR-6 polypeptide expressed and/or measuring the activity of the mACHR-6 polypeptide in the biological sample, comparing the amount of mACHR-6 polypeptide expressed in the biological sample and/or the measurable mACHR-6 biological activity in the cell to that of a control sample. An alteration in the amount of mACHR-6 polypeptide expression or mACHR-6 activity in the cell exposed to the compound or agent in comparison to the control is indicative of a modulation of mACHR-6 expression and/or mACHR-6 activity.

The invention also pertains to methods for identifying a compound or agent, e.g., a test compound or agent, which interacts with (e.g., binds to) an mACHR-6 polypeptide. These methods can include the steps of contacting the mACHR-6 polypeptide with the compound or agent under conditions which allow binding of the compound to the mACHR-6 polypeptide to form a complex and detecting the formation of a complex of the mACHR-6 polypeptide and the compound in which the ability of the compound to bind to the mACHR-6 polypeptide is indicated by the presence of the compound in the complex.

The invention further pertains to methods for identifying a compound or agent, e.g., a test compound or agent, which modulates, e.g., stimulates or inhibits, the interaction of the mACHR-6 polypeptide with a target molecule, e.g., acetylcholine, or a cellular protein involved in phosphatidylinositol turnover and signaling. In these methods, the mACHR-6 polypeptide is contacted, in the presence of the compound or agent, with the target molecule under conditions which allow binding of the target molecule to the mACHR-6 polypeptide to form a complex. An alteration, e.g., an increase or decrease, in complex formation between the mACHR-6 polypeptide and the target molecule as compared to the amount of complex formed in the absence of the compound or agent is indicative of the ability of the compound or agent to modulate the interaction of the mACHR-6 polypeptide with a target molecule.

BRIEF DESCRIPTION OF THE DRAWINGS

FIG. 1 depicts the human mACHR-6 nucleotide (SEQ ID NO:1) and amino acid (SEQ ID NO:2) sequences. The coding region without the 5' and 3' untranslated region of the human mACHR-6 gene is shown in SEQ ID NO:3.

FIG. 2 depicts the rat mACHR-6 nucleotide (SEQ ID NO:4) and amino acid (SEQ ID NO:5) sequences. The partial coding region without the 3' untranslated region of the rat mACHR-6 gene is shown in SEQ ID NO:6.

FIG. 3 depicts the rat mACHR-6 nucleotide and amino acid sequences shown in SEQ ID NOs:4 and 5, respectively, together with a 5' sequence upstream (nucleotides 1–118 of the nucleotide sequence shown in FIG. 3) from the codon in SEQ ID NO:4 which encodes the first amino acid (Gly). This additional 5' sequence may represent sequences, e.g., intronic sequences, which are not part of the rat sequence.

DETAILED DESCRIPTION OF THE INVENTION

The present invention is based on the discovery of novel molecules, referred to herein as mACHR-6 nucleic acid and polypeptide molecules, which play a role in or function in acetylcholine signaling pathways. In one embodiment, the mACHR-6 molecules modulate the activity of one or more proteins involved in a neurotransmitter signaling pathway, e.g., an acetylcholine signaling pathway. In a preferred embodiment, the mACHR-6 molecules of the present invention are capable of modulating the activity of proteins involved in the acetylcholine signaling pathway to thereby modulate the effects of acetylcholine on acetylcholine responsive cells.

As used herein, the phrase "acetylcholine responsive cells" refers to cells which have a function which can be modulated (e.g., stimulated or inhibited) by the neurotransmitter acetylcholine. Examples of such functions include mobilization of intracellular molecules which participate in a signal transduction pathway, e.g., phosphatidylinositol 4,5-bisphosphate ($PIP_2$) or inositol 1,4,5-triphosphate ($IP_3$), polarization of the plasma membrane, production or secretion of molecules, alteration in the structure of a cellular component, cell proliferation, cell migration, cell differentiation, and cell survival. Acetylcholine responsive cells preferably express an acetylcholine receptor, e.g., a muscarinic receptor. Examples of acetylcholine responsive cells include neural cells, e.g., central nervous system and peripheral nervous system cells (such as sympathetic and parasympathetic neurons); smooth muscle cells, e.g., smooth muscle cells in the digestive tract, the urinary tract, the blood vessels, the airways and the lungs, or the uterus; cardiac muscle cells, e.g., cardiomyocytes; and gland cells such as exocrine gland cells, e.g., pancreatic gland cells, e.g., pancreatic beta cells, tear gland cells, sweat gland cells, or parotid gland cells.

Depending on the type of cell, the response elicited by acetylcholine is different. For example, in neural cells, acetylcholine regulates ion channels, and neural signal to noise ratio. Inhibition or over stimulation of the activity of proteins involved in the acetylcholine signaling pathway or misexpression of acetylcholine can lead to hypo- or hyperpolarization of the neural plasma membrane and to perturbed neural signal to noise ratio, which can in turn lead to nervous system related disorders. Examples of nervous system related disorders include cognitive disorders, e.g., memory and learning disorders, such as amnesia, apraxia, agnosia, amnestic dysnomia, amnestic spatial disorientation, Kluver-Bucy syndrome, Alzheimer's related memory loss (Eglen R. M. (1996) *Pharmacol. and Toxicol.* 78(2):59–68; Perry E. K. (1995) *Brain and Cognition* 28(3):240–58) and learning disability; disorders affecting consciousness, e.g., visual hallucinations, perceptual disturbances, or delerium associated with Lewy body dementia; schitzo-effective disorders (Dean B. (1996) *Mol. Psychiatry* 1(1):54–8), schizophrenia with mood swings (Bymaster F. P. (1997) *J. Clin. Psychiatry* 58 (suppl.10):28–36; Yeomans J. S. (1995) *Neuropharmacol.* 12(1):3–16; Reimann D. (1994) *J. Psychiatric Res.* 28(3):195–210), depressive illness (primary or secondary); affective disorders (Janowsky D. S. (1994) *Am. J. Med. Genetics* 54(4):335–44); sleep disorders (Kimura F. (1997) *J. Neurophysiol.* 77(2):709–16), e.g., REM sleep abnormalities in patients suffering from, for example, depression (Riemann D. (1994) *J. Psychosomatic Res.* 38 Suppl. 1:15–25; Bourgin P. (1995) *Neuroreport* 6(3): 532–6), paradoxical sleep abnormalities (Sakai K. (1997) *Eur. J. Neuroscience* 9(3):415–23), sleep-wakefulness, and body temperature or respiratory depression abnormalities during sleep (Shuman S. L. (1995) *Am. J. Physiol.* 269(2 Pt 2):R308–17; Mallick B. N. (1997) *Brain Res.* 750(1–2) :311–7). Other examples of nervous system related disorders include disorders affecting pain generation mechanisms, e.g., pain related to irritable bowel syndrome (Mitch C. H. (1997) *J. Med. Chem.* 40(4):538–46; Shannon H. E. (1997) *J. Pharmac. and Exp. Therapeutics* 281(2):884–94; Bouaziz H. (1995) *Anesthesia and Analgesia* 80(6):1 140–4; or Guimaraes A. P. (1994) *Brain Res.* 647(2):220–30) or chest pain; movement disorders (Monassi C. R. (1997) *Physiol. and Behav.* 62(1):53–9), e.g., Parkinson's disease related movement disorders (Finn M. (1997) *Pharmacol. Biochem. & Behavior* 57(1–2):243–9; Mayorga A. J. (1997) *Pharmacol. Biochem. & Behavior* 56(2):273–9); eating disorders, e.g., insulin hypersecretion related obesity (Maccario M. (1997) *J. Endocrinol. Invest.* 20(l):8–12; Premawardhana L. D. (1994) *Clin. Endocrinol.* 40(5): 617–21); or drinking disorders, e.g., diabetic polydipsia (Murzi E. (1997) *Brain Res.* 752(1–2):184–8; Yang X. (1994) *Pharmacol. Biochem. & Behavior* 49(1):1–6).

In smooth muscle, acetylcholine regulates (e.g., stimulates or inhibits) contraction. Inhibition or overstimulation of the activity of proteins involved in the acetylcholine signaling pathway or misexpression of acetylcholine can lead to smooth muscle related disorders such as irritable bowel syndrome, diverticular disease, urinary incontinence, oesophageal achalasia, or chronic obstructive airways disease.

In cardiac muscle, acetylcholine induces a reduction in the heart rate and in cardiac contractility. Inhibition or overstimulation of the activity of proteins involved in the acetylcholine signaling pathway or misexpression of acetylcholine can lead to heart muscle related disorders such as pathologic bradycardia or tachycardia, arrhythmia, flutter or fibrillation.

In glands such as exocrine glands, acetylcholine regulates the secretion of enzymes or hormones, e.g., in the parotid gland acetylcholine induces the release of amylase, and in the pancreas acetylcholine induces the release of digestive enzymes and insulin. Inhibition or over stimulation of the activity of proteins involved in the acetylcholine signaling pathway or misexpression of acetylcholine can lead to gland related disorders such as xerostomia, or diabetes mellitus.

In a particularly preferred embodiment, the mACHR-6 molecules are capable of modulating the activity of G proteins, as well as phosphatidylinositol metabolism and turnover in acetylcholine responsive cells. As used herein, a "G protein" is a protein which participates, as a secondary signal, in a variety of intracellular signal transduction pathways, e.g., in the acetylcholine signaling pathway primarily through phosphatidylinositol metabolism and turnover. G proteins represent a family of heterotrimeric proteins composed of α, β and γ subunits, which bind guanine nucleotides. These proteins are usually linked to cell surface receptors, e.g., receptors containing seven transmembrane domains, such as the muscarinic receptors. Following ligand binding to the receptor, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cyclic AMP (e.g., by activation of adenylate cyclase), diacylglycerol or inositol phosphates. Greater than 20 different types of α-subunits are known in man, which associate with a smaller pool of β and γ subunits. Examples of mammalian G proteins include Gi, Go, Gq, Gs and Gt. G proteins are described extensively in Lodish H. et al. Molecular Cell Biology, (Scientific American Books Inc., New York, N.Y., 1995).

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of acetylcholine to a muscarinic receptor activates the plasma-membrane enzyme phospholipase C which in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

mACHR-6 nucleic acid molecules were identified by screening appropriate cDNA libraries (described in detail in Example 1). The rat mACHR-6 nucleic acid molecule was identified by screening a rat brain cDNA library. Positive clones were sequenced and the partial sequences were analyzed by comparison with sequences in a nucleic acid sequence data base. This analysis indicated that the sequences were homologous to the muscarinic family of receptors. A longer rat clone was then isolated and sequenced. The human mACHR-6 nucleic acid molecule was identified by screening a human cerebellum cDNA library using probes designed based on the rat sequence.

Because of its ability to interact with (e.g., bind to) acetylcholine, G proteins and other proteins involved in the acetylcholine signaling pathway, the mACHR-6 polypeptide is also a polypeptide which functions in the acetylcholine signaling pathway.

The nucleotide sequence of the isolated human mACHR-6 cDNA and the predicted amino acid sequence of the human mACHR-6 polypeptide are shown in FIG. 1 and in SEQ ID NOs:1 and 2, respectively. A plasmid containing the full length nucleotide sequence encoding human mACHR-6 was deposited with ATCC (American type Culture Collection, 10801 University Boulevard, Manassas, Va. 20110-2209) on Sep. 18, 1998 and assigned Accession Number 98902. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The nucleotide sequence of the isolated rat mACHR-6 cDNA and the predicted amino acid sequence of the rat mACHR-6 polypeptide are shown in FIG. 2 and in SEQ ID NOs:4 and 5, respectively.

The human mACHR-6 gene, which is approximately 2689 nucleotides in length, encodes a full length polypeptide having a molecular weight of approximately 51.2 KDa and which is approximately 445 amino acid residues in length. The human mACHR-6 polypeptide is expressed at least in the brain, in particular, regions of the brain such as the cerebellum, the cerebral cortex, the medulla, the occipital pole, the frontal lobe, the temporal lobe, the putamen, the corpus callosum the amygdala, the caudate nucleus, the hippocampus, the substantia nigra, the subthalamic nucleus and the thalamus; spinal cord, placenta, lungs, spleen, liver, skeletal muscle, kidney, and testis. Based on structural analysis, amino acid residues 34–59 (SEQ ID NO:7), 73–91 (SEQ ID NO:8), 109–130 (SEQ ID NO:9), 152–174 (SEQ ID NO:10), 197–219 (SEQ ID NO:11), 360–380 (SEQ ID NO:12), and 396–416 (SEQ ID NO:13) comprise transmembrane domains. As used herein, the term "transmembrane domain" refers to a structural amino acid motif which includes a hydrophobic helix that spans the plasma membrane. A transmembrane domain also preferably includes a series of conserved serine, threonine, and tyrosine residues. For example, the transmembrane domains between residues 109–130 (SEQ ID NO:9), 197–219 (SEQ ID NO:11), 360–380 (SEQ ID NO:12), and 396–416 (SEQ ID NO:13), contain threonine and tyrosine residues (located about 1–2 helical turns away from the membrane surface), which are important for ligand, e.g., acetylcholine, binding. Other important residues in the transmembrane domains include the conserved aspartate residue in the transmembrane domain between residues 109–130 (SEQ ID NO:9) and the conserved proline residue in the transmembrane domain between residues 152–174 (SEQ ID NO:10), which are also important for ligand, e.g., acetylcholine, binding. A skilled artisan will readily appreciate that the beginning and ending amino acid residue recited for various domains/fragments of mACHR-6 are based on structural analysis and that the actual beginning/ending amino acid for each may vary by a few amino acids from that identified herein.

The rat mACHR-6 gene, which is at least about 2218 nucleotides in length, encodes a full length polypeptide having a molecular weight of at least about 41.6 kDa and which is at least about 362 amino acid residues in length. The rat mACHR-6 polypeptide is expressed in the brain. Amino acid residues 1–8 (SEQ ID NO:14), 26–47 (SEQ ID NO:15), 69–91 (SEQ ID NO:16), 114–136 (SEQ ID NO:17), 277–297 (SEQ ID NO:18), and 313–333 (SEQ ID NO:19) comprise transmembrane domains.

The mACHR-6 polypeptide, a biologically active portion or fragment of the polypeptide, or an allelic variant thereof can have one or more of the following mACHR-6 activities: 1) it can interact with (e.g., bind to) acetylcholine; 2) it can interact with (e.g., bind to) a G protein or another protein which naturally binds to mACHR-6; 3) it can modulate the activity of an ion channel (e.g., a potassium channel or a calcium channel); 4) it can modulate cytosolic ion, e.g., calcium, concentration; 5) it can modulate the release of a neurotransmitter, e.g., acetylcholine, from a neuron, e.g., a presynaptic neuron; 6) it can modulate an acetylcholine response in an acetylcholine responsive cell (e.g., a smooth muscle cell or a gland cell) to, for example, beneficially affect the acetylcholine responsive cell, e.g., a neuron; 7) it can signal ligand binding via phosphatidylinositol turnover; and 8) it can modulate, e.g., activate or inhibit, phospholipase C activity.

Various aspects of the invention are described in further detail in the following subsections:

I. Isolated Nucleic Acid Molecules

One aspect of the invention pertains to isolated nucleic acid molecules that encode mACHR-6 or biologically active portions thereof, as well as nucleic acid fragments sufficient for use as hybridization probes to identify mACHR-6-encoding nucleic acid (e.g., mACHR-6 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated mACHR-6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a hippocampal cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1 or 4, or a portion thereof, can be isolated using standard molecular biology techniques and the sequence information provided herein. For example, a human mACHR-6 cDNA can be isolated from a human hippocampus library using all or portion of SEQ ID NO:1 or 4 as a hybridization probe and standard hybridization techniques (e.g., as described in Sambrook, J., Fritsh, E. F., and Maniatis, T. *Molecular Cloning: A Laboratory Manual. 2nd, ed., Cold Spring Harbor Laboratory,* Cold Spring harbor Laboratory Press, Cold Spring Harbor, N.Y., 1989). Moreover, a nucleic acid molecule encompassing all or a portion of SEQ ID NO:1 or 4 can be isolated by the polymerase chain reaction using oligonucleotide primers designed based upon the sequence of SEQ ID NO:1 or 4. For example, mRNA can be isolated from normal brain cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1 or 4. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an mACHR-6 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1 or 4 or the nucleotide sequence of the DNA insert of the plasmid deposited with ATCC as Accession Number 98902. The sequence of SEQ ID NO:1 corresponds to the human mACHR-6 cDNA. This cDNA comprises sequences encoding the human mACHR-6 polypeptide (i.e., "the coding region", from nucleotides 291 to 1628 of SEQ ID NO:1), as well as 5' untranslated sequences (nucleotides 1 to 290 of SEQ ID NO:1) and 3' untranslated sequences (nucleotides 1629 to 2689 of SEQ ID NO:1). Alternatively, the nucleic acid molecule can comprise only the coding region of SEQ ID NO:1 (e.g., nucleotides 291 to 1628 shown separately as SEQ ID NO:3). The sequence of SEQ ID NO:4 corresponds to the rat mACHR-6 cDNA. This cDNA comprises sequences encoding part of the rat mACHR-6 polypeptide (i.e., part of "the coding region", from nucleotides 1 to 1089 of SEQ ID NO:4), and 3' untranslated sequences (nucleotides 1090 to 2218 of SEQ ID NO:4). Alternatively, the nucleic acid molecule can comprise only the partial coding region of SEQ ID NO:4 (e.g., nucleotides 1 to 1089, shown separately as SEQ ID NO:6).

In another preferred embodiment, an isolated nucleic acid molecule of the invention comprises a nucleic acid molecule which is a complement of the nucleotide sequence shown in SEQ ID NO:1 or 4, the nucleotide sequence of the DNA insert of the plasmid deposited with ATCC as Accession Number 98902, or a portion of either of these nucleotide sequences. A nucleic acid molecule which is complementary to the nucleotide sequence shown in SEQ ID NO:1 or 4 or FIG. 3 is one which is sufficiently complementary to the nucleotide sequence shown in SEQ ID NO:1 or 4 or FIG. 3 such that it can hybridize to the nucleotide sequence shown in SEQ ID NO:1 or 4 or FIG. 3, respectively, thereby forming a stable duplex.

In still another preferred embodiment, an isolated nucleic acid molecule of the invention comprises a nucleotide sequence which is at least about 60–65%, preferably at least about 70–75%, more preferably at least about 80–85%, and even more preferably at least about 90–95% or more homologous to the nucleotide sequence shown in SEQ ID NO:1 or 4 or FIG. 3, or to the nucleotide sequence of the DNA insert of the plasmid deposited with ATCC as Accession Number 98902, or a portion of these nucleotide sequences. Preferably, such nucleic acid molecules encode functionally active or inactive allelic variants of mACHR-6. In an additional preferred embodiment, an isolated nucleic acid molecule of the invention comprises a nucleotide sequence which hybridizes, e.g., hybridizes under stringent conditions, to the nucleotide sequence shown in SEQ ID NO:1 or 4, FIG. 3, or the nucleotide sequence of the DNA insert of the plasmid deposited with ATCC as Accession Number 98902, or a portion of either of these nucleotide sequences.

Moreover, the nucleic acid molecule of the invention can comprise only a portion of the coding region of SEQ ID NO:1 or 4, for example a fragment which can be used as a probe or primer or a fragment encoding a biologically active portion of mACHR-6. The nucleotide sequence determined from the cloning of the mACHR-6 gene from a mammal allows for the generation of probes and primers designed for use in identifying and/or cloning mACHR-6 homologues in other cell types, e.g., from other tissues, as well as mACHR-6 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 or 4 sense, an anti-sense sequence of SEQ ID NO:1 or 4, or naturally occurring mutants thereof. Primers based on the nucleotide sequence in SEQ ID NO:1 or 4 can be used in PCR reactions to clone mACHR-6 homologues. Probes based on the mACHR-6 nucleotide sequences can be used to detect transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an mACHR-6 polypeptide, such as by measuring a level of an mACHR-6-encoding nucleic acid in a sample of cells from a subject e.g., detecting mACHR-6 mRNA levels or determining whether a genomic mACHR-6 gene has been mutated or deleted.

In one embodiment, the nucleic acid molecule of the invention encodes a polypeptide or portion thereof which includes an amino acid sequence which is sufficiently homologous to an amino acid sequence of SEQ ID NO:2 or 5 or an amino acid sequence encoded by the nucleotide sequence of the DNA insert of the plasmid deposited with ATCC as Accession Number 98902 such that the polypeptide or portion thereof maintains the ability to modulate an acetylcholine response in an acetylcholine responsive cell (e.g., naturally occurring allelic variants of the rat and human mACHR-6 polypeptides described herein). As used herein, the language "sufficiently homologous" refers to polypeptides or portions thereof which have amino acid sequences which include a minimum number of identical or equivalent (e.g., an amino acid residue which has a similar side chain as an amino acid residue in SEQ ID NO:2 or 5) amino acid residues to an amino acid sequence of SEQ ID NO:2 or 5 or an amino acid sequence encoded by the nucleotide sequence of the DNA insert of the plasmid deposited with ATCC as Accession Number 98902 such that the polypeptide or portion thereof is able to modulate an acetylcholine response in an acetylcholine responsive cell or a skilled artisan would clearly recognize it as a non-functional allelic variant of the rat and human mACHR-6 polypeptides described herein. Acetylcholine, as described herein, initiates a variety of responses in many different cell types. Examples of such responses are also described herein. In another embodiment, the polypeptide is at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the amino acid sequence of SEQ ID NO:2 or 5.

Portions of polypeptides encoded by the mACHR-6 nucleic acid molecule of the invention are preferably biologically active portions of the mACHR-6 polypeptide. As used herein, the term "biologically active portion of mACHR-6" is intended to include a portion, e.g., a domain/motif, of mACHR-6 that has one or more of the following mACHR-6 activities: 1) it can interact with (e.g., bind to) acetylcholine; 2) it can interact with (e.g., bind to) a G protein or another protein which naturally binds to mACHR-6; 3) it can modulate the activity of an ion channel (e.g., a potassium channel or a calcium channel); 4) it can modulate cytosolic ion, e.g., calcium, concentration; 5) it can modulate the release of a neurotransmitter, e.g., acetylcholine, from a neuron, e.g., a presynaptic neuron; 6) it can modulate an acetylcholine response in an acetylcholine responsive cell (e.g., a smooth muscle cell or a gland cell) to, for example, beneficially affect the acetylcholine responsive cell, e.g., a neuron; 7) it can signal ligand binding via phosphatidylinositol turnover; and 8) it can modulate, e.g., activate or inhibit, phospholipase C activity.

Standard binding assays, e.g., immunoprecipitations and yeast two-hybrid assays as described herein, can be performed to determine the ability of an mACHR-6 polypeptide or a biologically active portion thereof to interact with (e.g., bind to) a binding partner such as a G protein. To determine whether an mACHR-6 polypeptide or a biologically active portion thereof can modulate an acetylcholine response in an acetylcholine responsive cell, such cells can be transfected with a construct driving the overexpression of an mACHR-6 polypeptide or a biologically active portion thereof. Methods for the preparation of acetylcholine responsive cells, e.g., intact smooth muscle cells or extracts from such cells are known in the art and described in Glukhova et al. (1987) *Tissue Cell* 19 (5):657–63, Childs et al. (1992) *J. Biol. Chem.* 267(32):22853–9, and White et al. (1996) *J. Biol. Chem.* 271 (25):15008–17. The cells can be subsequently treated with acetylcholine, and a biological effect of acetylcholine on the cells, such as phosphatidylinositol turnover or cytosolic calcium concentration can be measured using methods known in the art (see Hartzell H. C. et al. (1988) *Prog. Biophys. Mol. Biol.* 52:165–247). Alternatively, transgenic animals, e.g., mice overexpressing an mACHR-6 polypeptide or a biologically active portion thereof, can be used. Tissues from such animals can be obtained and treated with acetylcholine. For example, methods for preparing detergent-skinned muscle fiber bundles are known in the art (Strauss et al. (1992) *Am. J. Physiol.* 262:1437–45). The contractility of these tissues in response to acetylcholine can be determined using, for example, isometric force measurements as described in Strauss et al., supra. Similarly, to determine whether an mACHR-6 polypeptide or a biologically active portion thereof can modulate an acetylcholine response in an acetylcholine responsive cell such as a gland cell, gland cells, e.g., parotid gland cells grown in tissue culture, can be transfected with a construct driving the overexpression of an mACHR-6 polypeptide or a biologically active portion thereof. The cells can be subsequently treated with acetylcholine, and the effect of the acetylcholine on amylase secretion from such cells can be determined using, for example an enzymatic assay with a labeled substrate. The preferred assays used for mACHR-6 activity will be based on phosphatidylinositol turnover such as those developed for the M1, M3 and M5 classes of receptors (see E. Watson et al. The *G Protein Linked Receptor: FactsBook* (Academic Press, Boston, Mass., 1994), the contents of which are incorporated herein by reference).

In one embodiment, the biologically active portion of mACHR-6 comprises a transmembrane domain. Preferably, the transmembrane domain is encoded by a nucleic acid molecule derived from a human and is at least about 50–55%, preferably at least about 60–65%, more preferably at least about 70–75%, even more preferably at least about 80–85%, and most preferably at least about 90–95% or more homologous to any of the transmembrane domains (i.e., amino acid residues 34–59, 109–130, 152–174, 197–219, or 396–416) of SEQ ID NO:2 which are shown as separate sequences designated SEQ ID NOs:7, 9, 10, 11, and 13, respectively, or to the rat transmembrane domains (i.e., amino acid residues 1–8, 26–47, 69–91, 114–136, 277–297, or 313–383) of SEQ ID NO:5 which are shown as separate sequences designated SEQ ID NOs: 14, 15, 16, 17, 18, and 19, respectively. More preferably, the transmembrane domain encoded by the human nucleic acid molecule is at least about 75–80%, preferably at least about 80–85%, more preferably at least about 85–90%, and most preferably at least about 90–95% or more homologous to the transmembrane domain (i.e., amino acid residues 360–380) of SEQ ID NO:2 which is shown as a separate sequence designated SEQ ID NO:12, or at least about 80–85%, more preferably at least about 85–90%, and most preferably at least about 90–95% or more homologous to the transmembrane domain (i.e., amino acid residues 73–91) of SEQ ID NO:2 which is shown as a separate sequence designated SEQ ID NO:8. In a preferred embodiment, the biologically active portion of the polypeptide which includes the transmembrane domain can modulate the activity of a G protein or other binding partner in a cell and/or modulate an acetylcholine response in an acetylcholine responsive cell, e.g., a brain cell, to thereby beneficially affect the cell. In a preferred embodiment, the biologically active portion comprises a transmembrane domain of the human mACHR-6 as represented by amino acid residues 34–59 (SEQ ID NO:7), 73–91 (SEQ ID NO:8), 109–130 (SEQ ID NO:9), 152–174 (SEQ ID NO:10), 197–219 (SEQ ID NO:11), 360–380 (SEQ ID NO:12), and 396–416 (SEQ ID NO:13) or a transmembrane domain of the rat mACHR-6 as represented by amino acid residues 1–8 (SEQ ID NO:14), 26–47 (SEQ ID NO:15), 69–91 (SEQ ID NO:16), 114–136 (SEQ ID NO:17), 277–297 (SEQ ID NO:18), and 313–333 (SEQ ID NO:19). Additional nucleic acid fragments encoding biologically active portions of mACHR-6 can be prepared by isolating a portion of SEQ ID NO:1 or 4, expressing the encoded portion of mACHR-6 polypeptide or peptide (e.g., by recombinant expression in vitro) and assessing the activity of the encoded portion of mACHR-6 polypeptide or peptide.

The invention further encompasses nucleic acid molecules that differ from the nucleotide sequence shown in SEQ ID NO:1 or 4 (and portions thereof) due to degeneracy of the genetic code and thus encode the same mACHR-6 polypeptide as that encoded by the nucleotide sequence shown in SEQ ID NO:1 or 4. In another embodiment, an isolated nucleic acid molecule of the invention has a nucleotide sequence encoding a polypeptide having an amino acid sequence shown in SEQ ID NO:2 or 5 or a polypeptide having an amino acid sequence encoded by the nucleotide sequence of the DNA insert of the plasmid deposited with ATCC as Accession Number 98902. In a still further embodiment, the nucleic acid molecule of the invention encodes a full length human polypeptide which is substantially homologous to the amino acid sequence of SEQ ID NO:2 or 4 (encoded by the open reading frame shown in SEQ ID NO:3 or 6, respectively) or an amino acid sequence encoded by the nucleotide sequence of the DNA insert of the plasmid deposited with ATCC as Accession Number 98902.

In addition to the mACHR-6 nucleotide sequence shown in SEQ ID NO:1 or 4, it will be appreciated by those skilled in the art that DNA sequence polymorphisms that lead to changes in the amino acid sequences of mACHR-6 may exist within a population (e.g., the human population). Such genetic polymorphism in the mACHR-6 gene may exist among individuals within a population due to natural allelic variation. As used herein, the terms "gene" and "recombinant gene" refer to nucleic acid molecules comprising an open reading frame encoding an mACHR-6 polypeptide, preferably a mammalian mACHR-6 polypeptide. Such natural allelic variations can typically result in 1–5% variance in the nucleotide sequence of the mACHR-6 gene. Any and all such nucleotide variations and resulting amino acid polymorphisms in mACHR-6 that are the result of natural allelic variation are intended to be within the scope of the invention. Such allelic variation includes both active allelic variants as well as non-active or reduced activity allelic variants, the later two types typically giving rise to a pathological disorder. Moreover, nucleic acid molecules encoding mACHR-6 polypeptides from other species, and thus which have a nucleotide sequence which differs from the human sequence of SEQ ID NO:1, are intended to be within the scope of the invention. Nucleic acid molecules corresponding to natural allelic variants and non-human homologues of the human mACHR-6 cDNA of the invention can be isolated based on their homology to the human mACHR-6 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or the nucleotide sequence of the DNA insert of the plasmid deposited with ATCC as Accession Number 98902. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50°–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide). In one embodiment, the nucleic acid encodes a natural human mACHR-6.

In addition to naturally-occurring allelic variants of the mACHR-6 sequence that may exist in the population, the skilled artisan will further appreciate that changes can be introduced by mutation into the nucleotide sequence of SEQ ID NO:1 or 4, thereby leading to changes in the amino acid sequence of the encoded mACHR-6 polypeptide, without altering the functional ability of the mACHR-6 polypeptide. For example, nucleotide substitutions leading to amino acid substitutions at "non-essential" amino acid residues can be made in the sequence of SEQ ID NO:1 or 4. A "non-essential" amino acid residue is a residue that can be altered from the wild-type sequence of mACHR-6 (e.g., the sequence of SEQ ID NO:2 or 5) without altering the activity of mACHR-6, whereas an "essential" amino acid residue is required for mACHR-6 activity. For example, conserved amino acid residues, e.g., aspartates, prolines threonines and tyrosines, in the transmembrane domains of mACHR-6 are most likely important for binding to acetylcholine and are thus essential residues of mACHR-6. Other amino acid residues, however, (e.g., those that are not conserved or only semi-conserved in the transmembrane domain) may not be essential for activity and thus are likely to be amenable to alteration without altering mACHR-6 activity.

Accordingly, another aspect of the invention pertains to nucleic acid molecules encoding mACHR-6 polypeptides that contain changes in amino acid residues that are not essential for mACHR-6 activity. Such mACHR-6 polypeptides differ in amino acid sequence from SEQ ID NO:2 or 5 yet retain at least one of the mACHR-6 activities described herein. In one embodiment, the isolated nucleic acid molecule comprises a nucleotide sequence encoding a polypeptide, wherein the polypeptide comprises an amino acid sequence at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the amino acid sequence of SEQ ID NO:2 or 5.

To determine the percent homology of two amino acid sequences (e.g., SEQ ID NO:2 or 5 and a mutant form thereof) or of two nucleic acids, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence (e.g., SEQ ID NO:2 or 5) is occupied by the same amino acid residue or nucleotide as the corresponding position in the other sequence (e.g., a mutant form of mACHR-6), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions× 100).

An isolated nucleic acid molecule encoding an mACHR-6 polypeptide homologous to the polypeptide of SEQ ID NO:2 or 5 can be created by introducing one or more nucleotide substitutions, additions or deletions into the nucleotide sequence of SEQ ID NO:1 or 4, respectively, such that one or more amino acid substitutions, additions or deletions are introduced into the encoded polypeptide. Mutations can be introduced into SEQ ID NO:1 or 4 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in mACHR-6 is preferably replaced with another amino acid residue from the same side chain family. Alternatively, in another embodiment, mutations can be introduced randomly along all or part of an mACHR-6 coding sequence, such as by saturation mutagenesis, and the resultant mutants can be screened for an mACHR-6 activity described herein to identify mutants that retain mACHR-6 activity. Following mutagenesis of SEQ ID NO:1 or 4, the encoded polypeptide can be expressed recombinantly (e.g., as described in Examples 3 and 4) and the activity of the polypeptide can be determined using, for example, assays described herein.

In addition to the nucleic acid molecules encoding mACHR-6 polypeptides described above, another aspect of the invention pertains to isolated nucleic acid molecules which are antisense thereto. An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire mACHR-6 coding strand, or to only a portion thereof. In one embodiment, an antisense nucleic acid molecule is antisense to a "coding region" of the coding strand of a nucleotide sequence encoding mACHR-6.

The term "coding region" refers to the region of the nucleotide sequence comprising codons which are translated into amino acid residues, e.g., the entire coding region of SEQ ID NO:1 comprises nucleotides 291 to 1628 (shown separately as SEQ ID NO:3) and the coding region of SEQ ID NO:4 comprises nucleotides 1 to 1089 (shown separately as SEQ ID NO:6). In another embodiment, the antisense nucleic acid molecule is antisense to a "noncoding region" of the coding strand of a nucleotide sequence encoding mACHR-6. The term "noncoding region" refers to 5' and 3' sequences which flank the coding region that are not translated into amino acids (i.e., also referred to as 5' and 3' untranslated regions).

Given the coding strand sequences encoding mACHR-6 disclosed herein (e.g., SEQ ID NOs:1 and 4), antisense nucleic acids of the invention can be designed according to the rules of Watson and Crick base pairing. The antisense nucleic acid molecule can be complementary to the entire coding region of mACHR-6 mRNA, but more preferably is an oligonucleotide which is antisense to only a portion of the coding or noncoding region of mACHR-6 mRNA. For example, the antisense oligonucleotide can be complementary to the region surrounding the translation start site of mACHR-6 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5 -carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3 -methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an mACHR-6 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An a-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mACHR-6 mRNA transcripts to thereby inhibit translation of mACHR-6 mRNA. A ribozyme having specificity for an mACHR-6-encoding nucleic acid can be designed based upon the nucleotide sequence of an mACHR-6 cDNA disclosed herein (i.e., SEQ ID NO:1 or 4). For example, a derivative of a *Tetrahymena* L-19 IVS RNA can be constructed in which the nucleotide sequence of the active site is complementary to the nucleotide sequence to be cleaved in an mACHR-6-encoding mRNA. See, e.g., Cech et al. U.S. Pat. No. 4,987,071 and Cech et al. U.S. Pat. No. 5,116,742. Alternatively, mACHR-6 mRNA can be used to select a catalytic RNA having a specific ribonuclease activity from a pool of RNA molecules. See, e.g., Bartel, D. and Szostak, J. W. (1993) *Science* 261:1411–1418.

Alternatively, mACHR-6 gene expression can be inhibited by targeting nucleotide sequences complementary to the regulatory region of the mACHR-6 (e.g., the mACHR-6 promoter and/or enhancers) to form triple helical structures that prevent transcription of the mACHR-6 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

II. Recombinant Expression Vectors and Host Cells

Another aspect of the invention pertains to vectors, preferably expression vectors, containing a nucleic acid encoding mACHR-6 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mACHR-6 polypeptides, mutant forms of mACHR-6, fusion polypeptides, and the like).

The recombinant expression vectors of the invention can be designed for expression of mACHR-6 in prokaryotic or eukaryotic cells. For example, mACHR-6 can be expressed in bacterial cells such as *E. coli*, insect cells (e.g., using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide. In one embodiment, the coding sequence of the mACHR-6 is cloned into a pGEX expression vector to create a vector encoding a fusion polypeptide comprising, from the N-terminus to the C-terminus, GST-thrombin cleavage site-mACHR-6. The fusion polypeptide can be purified by affinity chromatography using glutathione-agarose resin. Recombinant mACHR-6 unfused to GST can be recovered by cleavage of the fusion polypeptide with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant polypeptide expression in *E. coli* is to express the polypeptide in a host bacteria with an impaired capacity to proteolytically cleave the recombinant polypeptide (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the mACHR-6 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, mACHR-6 can be expressed in insect cells using, for example, baculovirus expression vectors. Baculovirus vectors available for expression of polypeptides in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO. J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) Cell 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to mACHR-6 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, mACHR-6 polypeptide can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding mACHR-6 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) mACHR-6 polypeptide. Accordingly, the invention further provides methods for producing mACHR-6 polypeptide using the host cells of the invention. In one embodiment, the method comprises culturing the host cell of invention (into which a recombinant expression vector encoding mACHR-6 has been introduced) in a suitable medium until mACHR-6 is produced. In another embodiment, the method further comprises isolating mACHR-6 from the medium or the host cell.

The host cells of the invention can also be used to produce non-human transgenic animals. The non-human transgenic animals can be used in screening assays designed to identify agents or compounds, e.g., drugs, pharmaceuticals, etc., which are capable of ameliorating detrimental symptoms of selected disorders such as nervous system disorders, smooth muscle related disorders, cardiac muscle related disorders and gland related disorders. For example, in one embodiment, a host cell of the invention is a fertilized oocyte or an embryonic stem cell into which mACHR-6-coding sequences have been introduced. Such host cells can then be used to create non-human transgenic animals in which exogenous mACHR-6 sequences have been introduced into their genome or homologous recombinant animals in which endogenous mACHR-6 sequences have been altered. Such animals are useful for studying the function and/or activity of mACHR-6 and for identifying and/or evaluating modulators of mACHR-6 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous mACHR-6 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing mACHR-6-encoding nucleic acid into the male pronuclei of a fertilized oocyte, e.g., by microinjection, retroviral infection, and allowing the oocyte to develop in a pseudopregnant female foster animal. The human mACHR-6 cDNA sequence of SEQ ID NO:1 can be introduced as a transgene into the genome of a non-human animal. Furthermore, the rat mACHR-6 cDNA sequence of SEQ ID NO:4 can be introduced as a transgene into the genome of a non-rat animal. Moreover, a non-human homologue of the human mACHR-6 gene, such as a mouse mACHR-6 gene, can be isolated based on hybridization to the human or rat mACHR-6 cDNA (described further in subsection 1 above) and used as a transgene. Intronic sequences and polyadenylation signals can also be included in the transgene to increase the efficiency of expression of the transgene. A tissue-specific regulatory sequence(s) can be operably linked to the mACHR-6 transgene to direct expression of mACHR-6 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the mACHR-6 transgene in its genome and/or expression of mACHR-6 mRNA in tissues or cells of the animals. A transgenic founder animal can then be used to breed additional animals carrying the transgene. Moreover, transgenic animals carrying a transgene encoding mACHR-6 can further be bred to other transgenic animals carrying other transgenes.

To create a homologous recombinant animal, a vector is prepared which contains at least a portion of an mACHR-6 gene into which a deletion, addition or substitution has been introduced to thereby alter, e.g., functionally disrupt, the mACHR-6 gene. The mACHR-6 gene can be a human gene (e.g., from a human genomic clone isolated from a human genomic library screened with the cDNA of SEQ ID NO:1), but more preferably, is a rat mACHR-6 gene of SEQ ID NO:4 or another non-human homologue of a human mACHR-6 gene. For example, a mouse mACHR-6 gene can be isolated from a mouse genomic DNA library using the mACHR-6 cDNA of SEQ ID NO:1 or 4 as a probe. The mouse mACHR-6 gene then can be used to construct a homologous recombination vector suitable for altering an endogenous mACHR-6 gene in the mouse genome. In a preferred embodiment, the vector is designed such that, upon homologous recombination, the endogenous mACHR-6 gene is functionally disrupted (i.e., no longer encodes a functional polypeptide; also referred to as a "knock out" vector). Alternatively, the vector can be designed such that, upon homologous recombination, the endogenous mACHR-6 gene is mutated or otherwise altered but still encodes functional polypeptide (e.g., the upstream regulatory region can be altered to thereby alter the expression of the endogenous mACHR-6 polypeptide). In the homologous recombination vector, the altered portion of the mACHR-6 gene is flanked at its 5' and 3' ends by additional nucleic acid of the mACHR-6 gene to allow for homologous recombination to occur between the exogenous mACHR-6 gene carried by the vector and an endogenous mACHR-6 gene in an embryonic stem cell. The additional flanking mACHR-6 nucleic acid is of sufficient length for successful homologous recombination with the endogenous gene. Typically, several kilobases of flanking DNA (both at the 5' and 3' ends) are included in the vector (see for example, Thomas, K. R. and Capecchi, M. R. (1987) *Cell* 51:503 for a description of homologous recombination vectors). The vector is introduced into an embryonic stem cell line (e.g., by electroporation) and cells in which the introduced mACHR-6 gene has homologously recombined with the endogenous mACHR-6 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells, A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; WO 92/0968; and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated mACHR-6 polypeptides and Anti-mACHR-6 Antibodies

Another aspect of the invention pertains to isolated mACHR-6 polypeptides, and biologically active portions thereof, as well as peptide fragments suitable for use as immunogens to raise anti-mACHR-6 antibodies. An "isolated" or "purified" polypeptide or biologically active portion thereof is substantially free of cellular material when produced by recombinant DNA techniques, or chemical precursors or other chemicals when chemically synthesized. The language "substantially free of cellular material" includes preparations of mACHR-6 polypeptide in which the polypeptide is separated from cellular components of the cells in which it is naturally or recombinantly produced. In one embodiment, the language "substantially free of cellular material" includes preparations of mACHR-6 polypeptide having less than about 30% (by dry weight) of non-mACHR-6 polypeptide (also referred to herein as a "contaminating polypeptide"), more preferably less than about 20% of non-mACHR-6 polypeptide, still more preferably less than about 10% of non-mACHR-6 polypeptide, and most preferably less than about 5% non-mACHR-6 polypeptide. When the mACHR-6 polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mACHR-6 polypeptide in which the polypeptide is separated from chemical precursors or other chemicals which are involved in the synthesis of the polypeptide. In one embodiment, the language "substantially free of chemical precursors or other chemicals" includes preparations of mACHR-6 polypeptide having less than about 30% (by dry weight) of chemical precursors or non-mACHR-6 chemicals, more preferably less than about 20% chemical precursors or non-mACHR-6 chemicals, still more preferably less than about 10% chemical precursors or non-mACHR-6 chemicals, and most preferably less than about 5% chemical precursors or non-mACHR-6 chemicals. In preferred embodiments, isolated polypeptides or biologically active portions thereof lack contaminating polypeptides from the same animal from which the mACHR-6 polypeptide is derived. Typically, such polypeptides are produced by recombinant expression of, for example, a human mACHR-6 polypeptide in a non-human cell.

An isolated mACHR-6 polypeptide or a portion thereof of the invention can modulate an acetylcholine response in an acetylcholine responsive cell or be a naturally occurring, non-functional allelic variant of an mACHR-6 polypeptide. In preferred embodiments, the polypeptide or portion thereof comprises an amino acid sequence which is sufficiently homologous to an amino acid sequence of SEQ ID NO:2 or 5 such that the polypeptide or portion thereof maintains the ability to modulate an acetylcholine response in an acetylcholine responsive cell. The portion of the polypeptide is preferably a biologically active portion as described herein. In another preferred embodiment, the human mACHR-6 polypeptide (i.e., amino acid residues 1–398 of SEQ ID NO:2) or the rat mACHR-6 polypeptide (i.e., amino acid residues 1–401 of SEQ ID NO:5) has an amino acid sequence shown in SEQ ID NO:2 or 5, respectively, or an amino acid sequence which is encoded by the nucleotide sequence of the DNA insert of the plasmid deposited with ATCC as Accession Number 98902. In yet another preferred embodiment, the mACHR-6 polypeptide has an amino acid sequence which is encoded by a nucleotide sequence which hybridizes, e.g., hybridizes under stringent conditions, to the nucleotide sequence of the DNA insert of the plasmid deposited with ATCC as Accession Number 98902. In still another preferred embodiment, the mACHR-6 polypeptide has an amino acid sequence which is encoded by a nucleotide sequence that is at least about 60–65%, preferably at least about 70–75%, more preferably at least about 80–85%, and even more preferably at least about 90–95% or more homologous to the nucleotide sequence of the DNA insert of the plasmid deposited with ATCC as Accession Number 98902. The preferred mACHR-6 polypeptides of the present invention also preferably possess at least one of the mACHR-6 activities described herein. For example, a preferred mACHR-6 polypeptide of the present invention includes an amino acid sequence encoded by a nucleotide sequence which hybridizes, e.g., hybridizes under stringent conditions, to the nucleotide sequence of the DNA insert of the plasmid deposited with ATCC as Accession Number 98902 and which can modulate an acetylcholine response in an acetylcholine responsive cell.

In other embodiments, the mACHR-6 polypeptide is substantially homologous to the amino acid sequence of SEQ ID NO:2 or 4 and retains the functional activity of the polypeptide of SEQ ID NO:2 or 4 yet differs in amino acid sequence due to natural allelic variation or mutagenesis, as described in detail in subsection 1 above. Accordingly, in another embodiment, the mACHR-6 polypeptide is a polypeptide which comprises an amino acid sequence which is at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the amino acid sequence of SEQ ID NO:2 or 5 and which has at least one of the mACHR-6 activities described herein. In still other embodiments, the invention pertains to a full length human polypeptide which is substantially homologous to the entire amino acid sequence of SEQ ID NO:2 or 5. In still another embodiment, the invention pertains to nonfunctional, naturally occurring allelic variants of the mACHR-6 polypeptides described herein. Such allelic variants will typically contain a non-conservative substitution, a deletion, or insertion or premature truncation of the amino acid sequence of SEQ ID NO:2 or 5.

Biologically active portions of the mACHR-6 polypeptide include peptides comprising amino acid sequences derived from the amino acid sequence of the mACHR-6 polypeptide, e.g., the amino acid sequence shown in SEQ ID NO:2 or 5 or the amino acid sequence of a polypeptide homologous to the mACHR-6 polypeptide, which include less amino acids than the full length mACHR-6 polypeptide or the full length polypeptide which is homologous to the mACHR-6 polypeptide, and exhibit at least one activity of the mACHR-6 polypeptide. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a transmembrane domain, with at least one activity of the mACHR-6 polypeptide. Preferably, the domain is a transmembrane domain derived from a human and is at least about 75–80%, preferably at least about 80–85%, more preferably at least about 85–90%, and most preferably at least about 90–95% or more homologous to SEQ ID NO:7, 8, 9, 10, 11, 12, or 13 or to the corresponding rat sequences. In a preferred embodiment, the biologically active portion of the polypeptide which includes the transmembrane domain can modulate the activity of a G protein in a cell and/or modulate an acetylcholine response in a cell, e.g., an acetylcholine responsive cell, e.g., a brain cell, to thereby beneficially affect the acetylcholine responsive cell. In a preferred embodiment, the biologically active portion comprises a transmembrane domain of mACHR-6 as represented by amino acid residues 34–59 (SEQ ID NO:7), 73–91 (SEQ ID NO:8), 109–130 (SEQ ID NO:9), 152–174 (SEQ ID NO:10), 197–219 (SEQ ID NO:11), 360–380 (SEQ ID NO:12), and 396–416 (SEQ ID NO:13), or the corresponding rat sequences shown in SEQ ID NOs: 14–20. Moreover, other biologically active portions, in which other regions of the polypeptide are deleted, can be prepared by recombinant techniques and evaluated for one or more of the activities described herein. Preferably, the biologically active portions of the mACHR-6 polypeptide include one or more selected domains/motifs or portions thereof having biological activity.

mACHR-6 polypeptides are preferably produced by recombinant DNA techniques. For example, a nucleic acid molecule encoding the polypeptide is cloned into an expression vector (as described above), the expression vector is introduced into a host cell (as described above) and the mACHR-6 polypeptide is expressed in the host cell. The mACHR-6 polypeptide can then be isolated from the cells by an appropriate purification scheme using standard polypeptide purification techniques. Alternative to recombinant expression, an mACHR-6 polypeptide, protein, or peptide can be synthesized chemically using standard peptide synthesis techniques. Moreover, native mACHR-6 polypeptide can be isolated from cells (e.g., hippocampal cells, substantia nigra cells, or parotid gland cells), for example using an anti-mACHR-6 antibody (described further below).

The invention also provides mACHR-6 chimeric or fusion polypeptides. As used herein, an mACHR-6 "chimeric polypeptide" or "fusion polypeptide" comprises an mACHR-6 polypeptide operatively linked to a non-mACHR-6 polypeptide. An "mACHR-6 polypeptide" refers to a polypeptide having an amino acid sequence corresponding to mACHR-6, whereas a "non-mACHR-6 polypeptide" refers to a heterologous polypeptide having an amino acid sequence corresponding to a polypeptide which is not substantially homologous to the mACHR-6 polypeptide, e.g., a polypeptide which is different from the mACHR-6 polypeptide and which is derived from the same or a different organism. Within the fusion polypeptide, the term "operatively linked" is intended to indicate that the mACHR-6 polypeptide and the non-mACHR-6 polypeptide are fused in-frame to each other. The non-mACHR-6 polypeptide can be fused to the N-terminus or C-terminus of the mACHR-6 polypeptide. For example, in one embodiment the fusion polypeptide is a GST-mACHR-6 fusion polypeptide in which the mACHR-6 sequences are fused to the C-terminus of the GST sequences. Other types of fusion polypeptides include, but are not limited to, enzymatic fusion polypeptides, for example beta-galactosidase fusions, yeast two-hybrid GAL fusions, poly His fusions and Ig fusions. Such fusion polypeptides, particularly poly His fusions, can facilitate the purification of recombinant mACHR-6. In another embodiment, the fusion polypeptide is an mACHR-6 polypeptide containing a heterologous signal sequence at its N-terminus. In certain host cells (e.g., mammalian host cells), expression and/or secretion of mACHR-6 can be increased through use of a heterologous signal sequence.

Preferably, an mACHR-6 chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An mACHR-6-encoding nucleic acid can be cloned into such an expression vector such that the fusion moiety is linked in-frame to the mACHR-6 polypeptide.

The present invention also pertains to homologues of the mACHR-6 polypeptides which function as either an mACHR-6 agonist (mimetic) or an mACHR-6 antagonist. In a preferred embodiment, the mACHR-6 agonists and antagonists stimulate or inhibit, respectively, a subset of the biological activities of the naturally occurring form of the mACHR-6 polypeptide. Thus, specific biological effects can be elicited by treatment with a homologue of limited function. In one embodiment, treatment of a subject with a homologue having a subset of the biological activities of the naturally occurring form of the polypeptide has fewer side effects in a subject relative to treatment with the naturally occurring form of the mACHR-6 polypeptide.

Homologues of the mACHR-6 polypeptide can be generated by mutagenesis, e.g., discrete point mutation or truncation of the mACHR-6 polypeptide. As used herein, the term "homologue" refers to a variant form of the mACHR-6 polypeptide which acts as an agonist or antagonist of the activity of the mACHR-6 polypeptide. An agonist of the mACHR-6 polypeptide can retain substantially the same, or a subset, of the biological activities of the mACHR-6 polypeptide. An antagonist of the mACHR-6 polypeptide can inhibit one or more of the activities of the naturally occurring form of the mACHR-6 polypeptide, by, for example, competitively binding to a downstream or upstream member of the mACHR-6 cascade which includes the mACHR-6 polypeptide. Thus, the mammalian mACHR-6 polypeptide and homologous thereof of the present invention can be either positive or negative regulators of acetylcholine responses in acetylcholine responsive cells.

In an alternative embodiment, homologues of the mACHR-6 polypeptide can be identified by screening combinatorial libraries of mutants, e.g., truncation mutants, of the mACHR-6 polypeptide for mACHR-6 polypeptide agonist or antagonist activity. In one embodiment, a variegated library of mACHR-6 variants is generated by combinatorial mutagenesis at the nucleic acid level and is encoded by a variegated gene library. A variegated library of mACHR-6 variants can be produced by, for example, enzymatically ligating a mixture of synthetic oligonucleotides into gene sequences such that a degenerate set of potential mACHR-6 sequences is expressible as individual polypeptides, or alternatively, as a set of larger fusion polypeptides (e.g., for phage display) containing the set of mACHR-6 sequences therein. There are a variety of methods which can be used to produce libraries of potential mACHR-6 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential mACHR-6 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the mACHR-6 polypeptide coding can be used to generate a variegated population of mACHR-6 fragments for screening and subsequent selection of homologues of an mACHR-6 polypeptide. In one embodiment, a library of coding sequence fragments can be generated by treating a double stranded PCR fragment of an mACHR-6 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the mACHR-6 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of mACHR-6 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify mACHR-6 homologues (Arkin and Yourvan (1992) PNAS89:7811–7815; Delgrave et al. (1993) *Protein Engineering* 6(3):327–331).

In one embodiment, cell based assays can be exploited to analyze a variegated mACHR-6 library. For example, a library of expression vectors can be transfected into a cell line ordinarily responsive to acetylcholine. The transfected cells are then contacted with acetylcholine and the effect of the mACHR-6 mutant on signaling by acetylcholine can be detected, e.g., by measuring intracellular calcium concentration. Plasmid DNA can then be recovered from the cells which score for inhibition, or alternatively, potentiation of acetylcholine induction, and the individual clones further characterized.

An isolated mACHR-6 polypeptide, or a portion or fragment thereof, can be used as an immunogen to generate antibodies that bind mACHR-6 using standard techniques for polyclonal and monoclonal antibody preparation. The full-length mACHR-6 polypeptide can be used or, alternatively, the invention provides antigenic peptide fragments of mACHR-6 for use as immunogens. The antigenic peptide of mACHR-6 comprises at least 8 amino acid residues of the amino acid sequence shown in SEQ ID NO:2 or 5 and encompasses an epitope of mACHR-6 such that an antibody raised against the peptide forms a specific immune complex with mACHR-6. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of mACHR-6 that are located on the surface of the polypeptide, e.g., hydrophilic regions.

An mACHR-6 immunogen typically is used to prepare antibodies by immunizing a suitable subject, (e.g., rabbit, goat, mouse or other mammal) with the immunogen. An appropriate immunogenic preparation can contain, for example, recombinantly expressed mACHR-6 polypeptide or a chemically synthesized mACHR-6 peptide. The preparation can further include an adjuvant, such as Freund's complete or incomplete adjuvant, or similar immunostimulatory agent. Immunization of a suitable subject with an immunogenic mACHR-6 preparation induces a polyclonal anti-mACHR-6 antibody response.

Accordingly, another aspect of the invention pertains to anti-mACHR-6 antibodies. The term "antibody" as used herein refers to immunoglobulin molecules and immunologically active portions of immunoglobulin molecules, i.e., molecules that contain an antigen binding site which specifically binds (immunoreacts with) an antigen, such as mACHR-6. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind mACHR-6. The term "monoclonal antibody" or "monoclonal antibody composition", as used herein, refers to a population of antibody molecules that contain only one species of an antigen binding site capable of immunoreacting with a particular epitope of mACHR-6. A monoclonal antibody composition thus typically displays a single binding affinity for a particular mACHR-6 polypeptide with which it immunoreacts.

Polyclonal anti-mACHR-6 antibodies can be prepared as described above by immunizing a suitable subject with an mACHR-6 immunogen. The anti-mACHR-6 antibody titer in the immunized subject can be monitored over time by standard techniques, such as with an enzyme linked immunosorbent assay (ELISA) using immobilized mACHR-6. If desired, the antibody molecules directed against mACHR-6 can be isolated from the mammal e.g., from the blood) and further purified by well known techniques, such as protein A hromatography to obtain the IgG fraction. At an appropriate time after immunization, e.g., hen the anti-mACHR-6 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1 976) *PNAS* 76:2927–3 1; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy,* Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses,* Plenum Publishing Corp., New York, New York (1980); E. A.

Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an mACHR-6 immunogen as described above, and the culture supernatants of the resulting hybridoma cells are screened to identify a hybridoma producing a monoclonal antibody that binds mACHR-6.

Any of the many well known protocols used for fusing lymphocytes and immortalized cell lines can be applied for the purpose of generating an anti-mACHR-6 monoclonal antibody (see, e.g., G. Galfre et al. (1977) *Nature* 266:55052; Gefter et al. *Somatic Cell Genet.,* cited supra; Lerner, *Yale J. Biol. Med.,* cited supra; Kenneth, *Monoclonal Antibodies,* cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Agl4 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind mACHR-6, e.g., using a standard ELISA assay.

Alternative to preparing monoclonal antibody-secreting hybridomas, a monoclonal anti-mACHR-6 antibody can be identified and isolated by screening a recombinant combinatorial immunoglobulin library (e.g., an antibody phage display library) with mACHR-6 to thereby isolate immunoglobulin library members that bind mACHR-6. Kits for generating and screening phage display libraries are commercially available (e.g., the Pharmacia *Recombinant Phage Antibody System,* Catalog No. 27-9400-01; and the Stratagene *SurfZAP™ Phage Display Kit,* Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Iluse et al. (1989) *Science* 246:1275–128 1; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-mACHR-6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. PCT International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-mACHR-6 antibody (e.g., monoclonal antibody) can be used to isolate mACHR-6 by standard techniques, such as affinity chromatography or immunoprecipitation. An anti-mACHR-6 antibody can facilitate the purification of natural mACHR-6 from cells and of recombinantly produced mACHR-6 expressed in host cells. Moreover, an anti-mACHR-6 antibody can be used to detect mACHR-6 polypeptide (e.g., in a cellular lysate or cell supernatant) in order to evaluate the abundance and pattern of expression of the mACHR-6 polypeptide or a fragment of an mACHR-6 polypeptide. The detection of circulating fragments of an mACHR-6 polypeptide can be used to identify mACHR-6 turnover in a subject. Anti-mACHR-6 antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

IV. Pharmaceutical Compositions

The mACHR-6 nucleic acid molecules, mACHR-6 polypeptides (particularly fragments of mACHR-6), mACHR-6 modulators, and anti-mACHR-6 antibodies (also referred to herein as "active compounds") of the invention can be incorporated into pharmaceutical compositions suitable for administration to a subject, e.g., a human. Such compositions typically comprise the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an mACHR-6 polypeptide or anti-mACHR-6 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, polypeptides, polypeptide homologues, modulators, and antibodies described herein can be used in one or more of the following methods: a) drug screening assays; b) diagnostic assays particularly in disease identification, allelic screening and pharmocogenetic testing; c) methods of treatment; d) pharmacogenomics; and e) monitoring of effects during clinical trials. An mACHR-6 polypeptide of the invention has one or more of the activities described herein and can thus be used to, for example, modulate an acetylcholine response in an acetylcholine responsive cell, for example by binding to acetylcholine or an mACHR-6 binding partner making it unavailable for binding to the naturally present mACHR-6 polypeptide. The isolated nucleic acid molecules of the invention can be used to express mACHR-6 polypeptide (e.g., via a recombinant expression vector in a host cell or in gene therapy applications), to detect mACHR-6 mRNA (e.g., in a biological sample) or a naturally occurring or recombinantly generated genetic mutation in an mACHR-6 gene, and to modulate mACHR-6 activity, as described further below. In addition, the mACHR-6 polypeptides can be used to screen drugs or compounds which modulate mACHR-6 polypeptide activity as well as to treat disorders characterized by insufficient production of mACHR-6 polypeptide or production of mACHR-6 polypeptide forms which have decreased activity compared to wild type mACHR-6. Moreover, the anti-mACHR-6 antibodies of the invention can be used to detect and isolate an mACHR-6 polypeptide, particularly fragments of mACHR-6 present in a biological sample, and to modulate mACHR-6 polypeptide activity.

a. Drug Screening Assays:

The invention provides methods for identifying compounds or agents which can be used to treat disorders characterized by (or associated with) aberrant or abnormal mACHR-6 nucleic acid expression and/or mACHR-6 polypeptide activity. These methods are also referred to herein as drug screening assays and typically include the step of screening a candidate/test compound or agent to be an agonist or antagonist of mACHR-6, and specifically for the ability to interact with (e.g., bind to) an mACHR-6 polypeptide, to modulate the interaction of an mACHR-6 polypeptide and a target molecule, and/or to modulate mACHR-6 nucleic acid expression and/or mACHR-6 polypeptide activity. Candidate/test compounds or agents which have one or more of these abilities can be used as drugs to treat disorders characterized by aberrant or abnormal mACHR-6 nucleic acid expression and/or mACHR-6 polypeptide activity. Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which interact with (e.g., bind to) mACHR-6 polypeptide. Typically, the assays are recombinant cell based or cell-free assays which include the steps of combining an mACHR-6 polypeptide or a bioactive fragment thereof, and a candidate/test compound, e.g., under conditions which allow for interaction of (e.g., binding of) the candidate/test compound to the mACHR-6 polypeptide or fragment thereof to form a complex, and detecting the formation of a complex, in which the ability of the candidate compound to interact with (e.g., bind to) the mACHR-6 polypeptide or fragment thereof is indicated by the presence of the candidate compound in the complex. Formation of complexes between the mACHR-6 polypeptide and the candidate compound can be quantitated, for example, using standard immunoassays.

In another embodiment, the invention provides screening assays to identify candidate/test compounds which modulate (e.g., stimulate or inhibit) the interaction (and most likely mACHR-6 activity as well) between an mACHR-6 polypeptide and a molecule (target molecule) with which the mACHR-6 polypeptide normally interacts. Examples of such target molecules include polypeptides in the same signaling path as the mACHR-6 polypeptide, e.g., polypeptides which may function upstream (including both stimulators and inhibitors of activity) or downstream of the mACHR-6 polypeptide in, for example, a cognitive function signaling pathway or in a pathway involving mACHR-6 activity, e.g., a G protein or other interactor involved in phosphatidylinositol turnover and/or phospholipase C activation. Typically, the assays are recombinant cell based or cell-free assays which include the steps of combining a cell expressing an mACHR-6 polypeptide, or a bioactive fragment thereof, an mACHR-6 target molecule (e.g., an mACHR-6 ligand) and a candidate/test compound, e.g., under conditions wherein but for the presence of the candidate compound, the mACHR-6 polypeptide or biologically active portion thereof interacts with (e.g., binds to) the target molecule, and detecting the formation of a complex which includes the mACHR-6 polypeptide and the target molecule or detecting the interaction/reaction of the mACHR-6 polypeptide and the target molecule. Detection of complex formation can include direct quantitation of the complex by, for example, measuring inductive effects of the mACHR-6 polypeptide. A statistically significant change, such as a decrease, in the interaction of the mACHR-6 and target molecule (e.g., in the formation of a complex between the mACHR-6 and the target molecule) in the presence of a candidate compound (relative to what is detected in the absence of the candidate compound) is indicative of a modulation (e.g., stimulation or inhibition) of the interaction between the mACHR-6 polypeptide and the target molecule. Modulation of the formation of complexes between the mACHR-6 polypeptide and the target molecule can be quantitated using, for example, an immunoassay.

To perform cell free drug screening assays, it is desirable to immobilize either mACHR-6 or its target molecule to facilitate separation of complexes from uncomplexed forms of one or both of the polypeptides, as well as to accommodate automation of the assay. Interaction (e.g., binding of) of mACHR-6 to a target molecule, in the presence and absence of a candidate compound, can be accomplished in any vessel suitable for containing the reactants. Examples of such vessels include microtitre plates, test tubes, and microcentrifuge tubes. In one embodiment, a fusion polypeptide can be provided which adds a domain that allows the polypeptide to be bound to a matrix. For example, glutathione-S-transferase/mACHR-6 fusion polypeptides can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of mACHR-6-binding polypeptide found in the bead fraction quantitated from the gel using standard electrophoretic techniques.

Other techniques for immobilizing polypeptides on matrices can also be used in the drug screening assays of the invention. For example, either mACHR-6 or its target molecule can be immobilized utilizing conjugation of biotin and streptavidin. Biotinylated mACHR-6 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with mACHR-6 but which do not interfere with binding of the polypeptide to its target molecule can be derivatized to the wells of the plate, and mACHR-6 trapped in the wells by antibody conjugation. As described above, preparations of an mACHR-6 -binding polypeptide and a candidate compound are incubated in the mACHR-6 -presenting wells of the plate, and the amount of complex trapped in the well can be quantitated. Methods for detecting such complexes, in addition to those described above for the GST-immobilized complexes, include immunodetection of complexes using antibodies reactive with the mACHR-6 target molecule, or which are reactive with mACHR-6 polypeptide and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal mACHR-6 nucleic acid expression or mACHR-6 polypeptide activity. This method typically includes the step of assaying the ability of the compound or agent to modulate the expression of the mACHR-6 nucleic acid or the activity of the mACHR-6 polypeptide thereby identifying a compound for treating a disorder characterized by aberrant or abnormal mACHR-6 nucleic acid expression or mACHR-6 polypeptide activity. Disorders characterized by aberrant or abnormal mACHR-6 nucleic acid expression or mACHR-6 polypeptide activity are described herein. Methods for assaying the ability of the compound or agent to modulate the expression of the mACHR-6 nucleic acid or activity of the mACHR-6 polypeptide are typically cell-based assays. For example, cells which are sensitive to ligands which transduce signals via a pathway involving mACHR-6 can be induced to overexpress an mACHR-6 polypeptide in the presence and absence of a candidate compound. Candidate compounds which produce a statistically significant change in mACHR-6 -dependent responses (either stimulation or inhibition) can be identified. In one embodiment, expression of the mACHR-6 nucleic acid or activity of an mACHR-6 polypeptide is modulated in cells and the effects of candidate compounds on the readout of interest (such as phosphatidylinositol turnover) are measured. For example, the expression of genes which are up- or down-regulated in response to an mACHR-6-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of mACHR-6 or mACHR-6 target molecules can also be measured, for example, by immunoblotting.

Alternatively, modulators of mACHR-6 expression (e.g., compounds which can be used to treat a disorder characterized by aberrant or abnormal mACHR-6 nucleic acid expression or mACHR-6 polypeptide activity) can be identified in a method wherein a cell is contacted with a candidate compound and the expression of mACHR-6 mRNA or polypeptide in the cell is determined. The level of expression of mACHR-6 mRNA or polypeptide in the presence of the candidate compound is compared to the level of expression of mACHR-6 mRNA or polypeptide in the absence of the candidate compound. The candidate compound can then be identified as a modulator of mACHR-6 nucleic acid expression based on this comparison and be used to treat a disorder characterized by aberrant mACHR-6 nucleic acid expression. For example, when expression of mACHR-6 mRNA or polypeptide is greater (statistically significantly greater) in the presence of the candidate compound than in its absence, the candidate compound is identified as a stimulator of mACHR-6 nucleic acid expression. Alternatively, when mACHR-6 nucleic acid expression is less (statistically significantly less) in the presence of the candidate compound than in its absence, the candidate compound is identified as an inhibitor of mACHR-6 nucleic acid expression. The level of mACHR-6 nucleic acid expression in the cells can be determined by methods described herein for detecting mACHR-6 mRNA or polypeptide.

In yet another aspect of the invention, the mACHR-6 polypeptides, or fragments thereof, can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with mACHR-6 ("mACHR-6-binding proteins" or "mACHR-6-bp") and modulate mACHR-6 polypeptide activity. Such mACHR-6-binding proteins are also likely to be involved in the propagation of signals by the mACHR-6 polypeptides as, for example, upstream or downstream elements of the mACHR-6 pathway.

The two-hybrid system is based on the modular nature of most transcription factors, which consist of separable DNA-binding and activation domains. Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179. Briefly, the assay utilizes two different DNA constructs. In one construct, the gene that codes for mACHR-6 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an mACHR-6-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with mACHR-6.

Modulators of mACHR-6 polypeptide activity and/or mACHR-6 nucleic acid expression identified according to these drug screening assays can be used to treat, for example, nervous system disorders, smooth muscle related disorders, cardiac muscle related disorders, and gland related disorders. These methods of treatment include the steps of administering the modulators of mACHR-6 polypeptide activity and/or nucleic acid expression, e.g., in a pharmaceutical composition as described in subsection IV above, to a subject in need of such treatment, e.g., a subject with a disorder described herein.

b. Diagnostic Assays:

The invention further provides a method for detecting the presence of mACHR-6, or fragment thereof, in a biological sample. The method involves contacting the biological sample with a compound or an agent capable of detecting mACHR-6 polypeptide or mRNA such that the presence of mACHR-6 is detected in the biological sample. A preferred agent for detecting mACHR-6 mRNA is a labeled or labelable nucleic acid probe capable of hybridizing to mACHR-6 mRNA. The nucleic acid probe can be, for example, the full-length mACHR-6 cDNA of SEQ ID NO:1 or 4, or a portion thereof, such as an oligonucleotide of at least 15, 30, 50, 100, 250 or 500 nucleotides in length and sufficient to specifically hybridize under stringent conditions to mACHR-6 mRNA. A preferred agent for detecting mACHR-6 polypeptide is a labeled or labelable antibody capable of binding to mACHR-6 polypeptide. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mACHR-6 mRNA or polypeptide in a biological sample in vitro as well as in vivo. For example, in vitro techniques for detection of mACHR-6 mRNA include Northern hybridizations and in situ hybridizations. In vitro techniques for detection of mACHR-6 polypeptide include enzyme linked immunosorbent assays (ELISAs), Western blots, immunoprecipitations and immunofluorescence. Alternatively, mACHR-6 polypeptide can be detected in vivo in a subject by introducing into the subject a labeled anti-mACHR-6 antibody. For example, the antibody can be labeled with a radioactive marker whose presence and location in a subject can be detected by standard imaging techniques. Particularly useful are methods which detect the allelic variant of mACHR-6 expressed in a subject and methods which detect fragments of an mACHR-6 polypeptide in a sample.

The invention also encompasses kits for detecting the presence of mACHR-6 in a biological sample. For example, the kit can comprise a labeled or labelable compound or agent capable of detecting mACHR-6 polypeptide or mRNA in a biological sample; means for determining the amount of mACHR-6 in the sample; and means for comparing the amount of mACHR-6 in the sample with a standard. The compound or agent can be packaged in a suitable container. The kit can further comprise instructions for using the kit to detect mACHR-6 mRNA or polypeptide.

The methods of the invention can also be used to detect naturally occurring genetic mutations in an mACHR-6 gene, thereby determining if a subject with the mutated gene is at risk for a disorder characterized by aberrant or abnormal mACHR-6 nucleic acid expression or mACHR-6 polypeptide activity as described herein. In preferred embodiments, the methods include detecting, in a sample of cells from the subject, the presence or absence of a genetic mutation characterized by at least one of an alteration affecting the integrity of a gene encoding an mACHR-6 polypeptide, or the misexpression of the mACHR-6 gene. For example, such genetic mutations can be detected by ascertaining the existence of at least one of 1) a deletion of one or more nucleotides from an mACHR-6 gene; 2) an addition of one or more nucleotides to an mACHR-6 gene; 3) a substitution of one or more nucleotides of an mACHR-6 gene, 4) a chromosomal rearrangement of an mACHR-6 gene; 5) an alteration in the level of a messenger RNA transcript of an mACHR-6 gene, 6) aberrant modification of an mACHR-6 gene, such as of the methylation pattern of the genomic DNA, 7) the presence of a non-wild type splicing pattern of a messenger RNA transcript of an mACHR-6 gene, 8) a non-wild type level of an mACHR-6-polypeptide, 9) allelic loss of an mACHR-6 gene, and 10) inappropriate post-translational modification of an mACHR-6-polypeptide. As described herein, there are a large number of assay techniques known in the art which can be used for detecting mutations in an mACHR-6 gene.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the mACHR-6-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an mACHR-6 gene under conditions such that hybridization and amplification of the mACHR-6-gene (if present) occurs, and detecting the presence or absence of an amplification product, or detecting the size of the amplification product and comparing the length to a control sample.

In an alternative embodiment, mutations in an mACHR-6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the mACHR-6 gene and detect mutations by comparing the sequence of the sample mACHR-6 with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the mACHR-6 gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal mACHR-6 nucleic acid expression and/or mACHR-6 polypeptide activity. These methods include the step of administering an mACHR-6 modulator (agonist or antagonist) to the subject such that treatment occurs. The language "aberrant or abnormal mACHR-6 expression" refers to expression of a non-wild-type mACHR-6 polypeptide or a non-wild-type level of expression of an mACHR-6 polypeptide. Aberrant or abnormal mACHR-6 activity refers to a non-wild-type mACHR-6 activity or a non-wild-type level of mACHR-6 activity. As the mACHR-6 polypeptide is involved in a pathway involving modulation of neurotransmitter, e.g., acetylcholine, release; modulation of smooth muscle contraction; modulation of cardiac muscle contraction; and modulation of gland, e.g., exocrine gland function, aberrant or abnormal mACHR-6 activity or expression interferes with the normal neurotransmitter, e.g., acetylcholine, release; normal smooth muscle; and cardiac muscle contraction; and normal gland, e.g., exocrine gland function. Non-limiting examples of disorders or diseases characterized by or associated with abnormal or aberrant mACHR-6 activity or expression include nervous system related disorders, e.g., central nervous system related disorders. Examples of nervous system related disorders include cognitive disorders, e.g., memory and learning disorders, such as amnesia, apraxia, agnosia, amnestic dysnomia, amnestic spatial disorientation, Kluver-Bucy syndrome, Alzheimer's related memory loss (Eglen R. M. (1996) *Pharmacol. and Toxicol.* 78(2):59–68; Perry E. K. (1995) *Brain and Cognition* 28(3):240–58) and learning disability; disorders affecting consciousness, e.g., visual hallucinations, perceptual disturbances, or delerium associated with Lewy body dementia; schitzo-effective disorders (Dean B. (1996) *Mol. Psychiatry* 1(l):54–8), schizophrenia with mood swings (Bymaster F. P. (1997) *J. Clin. Psychiatry* 58 (suppl.10):28–36; Yeomans J. S. (1995) *Neuropharmacol.* 12(l):3–16; Reimann D. (1994) *J. Psychiatric Res.* 28(3):195–210), depressive illness (primary or secondary); affective disorders (Janowsky D. S. (1994) *Am. J. Med. Genetics* 54(4):335–44); sleep disorders (Kimura F. (1997) *J. Neurophysiol.* 77(2):709–16), e.g., REM sleep abnormalities in patients suffering from, for example, depression (Riemann D. (1994) *J. Psychosomatic Res.* 38 Suppl. 1:15–25; Bourgin P. (1995) *Neuroreport* 6(3): 532–6), paradoxical sleep abnormalities (Sakai K. (1997) *Eur. J. Neuroscience* 9(3):415–23), sleep-wakefulness, and body temperature or respiratory depression abnormalities during sleep (Shuman S. L. (1995) *Am. J. Physiol.* 269(2 Pt 2):R308–17; Mallick B. N. (1997) *Brain Res.* 750(1–2) :311–7). Other examples of nervous system related disorders include disorders affecting pain generation mechanisms, e.g., pain related to irritable bowel syndrome (Mitch C. H. (1997) *J. Med. Chem.* 40(4):538–46; Shannon H. E. (1997) *J. Pharmac. and Exp. Therapeutics* 281(2):884–94; Bouaziz H. (1995) *Anesthesia and Analgesia* 80(6):1140–4; or Guimaraes A. P. (1994) *Brain Res.* 647(2):220–30) or chest pain; movement disorders (Monassi C. R. (1997) *Physiol. and Behav.* 62(1):53–9), e.g., Parkinson's disease related movement disorders (Finn M. (1997) *Pharmacol. Biochem. & Behavior* 57(1–2):243–9; Mayorga A. J. (1997) *Pharmacol. Biochem. & Behavior* 56(2):273–9); eating disorders, e.g., insulin hypersecretion related obesity (Maccario M. (1997) *J. Endocrinol. Invest.* 20(1):8–12; Premawardhana L. D. (1994) *Clin. Endocrinol.* 40(5): 617–21); or drinking disorders, e.g., diabetic polydipsia (Murzi E. (1997) *Brain Res.* 752(1–2):184–8; Yang X. (1994) *Pharmacol. Biochem. & Behavior* 49(1):1–6). Yet further examples of disorders or diseases characterized by or associated with abnormal or aberrant mACHR-6 activity or expression include smooth muscle related disorders such as irritable bowel syndrome, diverticular disease, urinary incontinence, oesophageal achalasia, or chronic obstructive airways disease; heart muscle related disorders such as pathologic bradycardia or tachycardia, arrhythmia, flutter or fibrillation; or gland related disorders such as xerostomia, or diabetes mellitus. The terms "treating" or "treatment", as used herein, refer to reduction or alleviation of at least one adverse effect or symptom of a disorder or disease, e.g., a disorder or disease characterized by or associated with abnormal or aberrant mACHR-6 polypeptide activity or mACHR-6 nucleic acid expression.

As used herein, an mACHR-6 modulator is a molecule which can modulate mACHR-6 nucleic acid expression and/or mACHR-6 polypeptide activity. For example, an mACHR-6 modulator can modulate, e.g., upregulate (activate/agonize) or downregulate (suppress/antagonize), mACHR-6 nucleic acid expression. In another example, an mACHR-6 modulator can modulate (e.g., stimulate/agonize or inhibit/antagonize) mACHR-6 polypeptide activity. If it is desirable to treat a disorder or disease characterized by (or associated with) aberrant or abnormal (non-wild-type) mACHR-6 nucleic acid expression and/or mACHR-6 polypeptide activity by inhibiting mACHR-6 nucleic acid expression, an mACHR-6 modulator can be an antisense molecule, e.g., a ribozyme, as described herein. Examples of antisense molecules which can be used to inhibit mACHR-6 nucleic acid expression include antisense molecules which are complementary to a portion of the 5' untranslated region of SEQ ID NO:1 which also includes the start codon and antisense molecules which are complementary to a portion of the 3' untranslated region of SEQ ID NO:1 or 4. An example of an antisense molecule which is complementary to a portion of the 5' untranslated region of SEQ ID NO:1 and which also includes the start codon is a nucleic acid molecule which includes nucleotides which are complementary to nucleotides 280 to 296 of SEQ ID NO:1. This antisense molecule has the following nucleotide sequence: 5' CCTGCGGGGCCATGGAG 3' (SEQ ID NO:20). An example of an antisense molecule which is complementary to a portion of the 3' untranslated region of SEQ ID NO:1 is a nucleic acid molecule which includes nucleotides which are complementary to nucleotides 1629 to 1645 of SEQ ID NO:1. This antisense molecule has the following sequence: 5' GTGGCCCACCAGAGCCT 3' (SEQ ID NO:21). An additional example of an antisense molecule which is complementary to a portion of the 3' untranslated region of SEQ ID NO:1 is a nucleic acid molecule which includes nucleotides which are complementary to nucleotides 1650 to 1666 of SEQ ID NO:1. This antisense molecule has the following sequence: 5' CAGCCACGCCTCTCTCA 3' (SEQ ID NO:22). An example of an antisense molecule which is complementary to a portion of the 3' untranslated region of SEQ ID NO:4 is a nucleic acid molecule which includes nucleotides which are complementary to nucleotides 1087 to 1102 of SEQ ID NO:4. This antisense molecule has the following sequence: 5' TGAGCAGCTGCCCCAC 3' (SEQ ID NO:23). An additional example of an antisense molecule which is complementary to a portion of the 3' untranslated region of SEQ ID NO:4 is a nucleic acid molecule which includes nucleotides which are complementary to nucleotides 1107 to 1122 of SEQ ID NO:4. This antisense molecule has the following sequence: 5' CTGAGGCCAG-GCCCTT 3' (SEQ ID NO:24).

An mACHR-6 modulator which inhibits mACHR-6 nucleic acid expression can also be a small molecule or other drug, e.g., a small molecule or drug identified using the screening assays described herein, which inhibits mACHR-6 nucleic acid expression. If it is desirable to treat a disease or disorder characterized by (or associated with) aberrant or abnormal (non-wild-type) mACHR-6 nucleic acid expression and/or mACHR-6 polypeptide activity by stimulating mACHR-6 nucleic acid expression, an mACHR-6 modulator can be, for example, a nucleic acid molecule encoding mACHR-6 (e.g., a nucleic acid molecule comprising a nucleotide sequence homologous to the nucleotide sequence of SEQ ID NO:1 or 4) or a small molecule or other drug, e.g., a small molecule (peptide) or drug identified using the screening assays described herein, which stimulates mACHR-6 nucleic acid expression.

Alternatively, if it is desirable to treat a disease or disorder characterized by (or associated with) aberrant or abnormal (non-wild-type) mACHR-6 nucleic acid expression and/or mACHR-6 polypeptide activity by inhibiting mACHR-6 polypeptide activity, an mACHR-6 modulator can be an anti-mACHR-6 antibody or a small molecule or other drug, e.g., a small molecule or drug identified using the screening assays described herein, which inhibits mACHR-6 polypeptide activity. If it is desirable to treat a disease or disorder characterized by (or associated with) aberrant or abnormal (non-wild-type) mACHR-6 nucleic acid expression and/or mACHR-6 polypeptide activity by stimulating mACHR-6 polypeptide activity, an mACHR-6 modulator can be an active mACHR-6 polypeptide or portion thereof (e.g., an mACHR-6 polypeptide or portion thereof having an amino acid sequence which is homologous to the amino acid sequence of SEQ ID NO:2 or 5 or a portion thereof) or a small molecule or other drug, e.g., a small molecule or drug identified using the screening assays described herein, which stimulates mACHR-6 polypeptide activity.

Other aspects of the invention pertain to methods for modulating a cell associated activity. These methods include contacting the cell with an agent (or a composition which includes an effective amount of an agent) which modulates mACHR-6 polypeptide activity or mACHR-6 nucleic acid expression such that a cell associated activity is altered relative to a cell associated activity (for example, phosphatidylinositol metabolism) of the cell in the absence of the agent. As used herein, "a cell associated activity" refers to a normal or abnormal activity or function of a cell. Examples of cell associated activities include phosphatidylinositol turnover, production or secretion of molecules, such as proteins, contraction, proliferation, migration, differentiation, and cell survival. In a preferred embodiment, the cell is neural cell of the brain, e.g., a hippocampal cell. The term "altered" as used herein refers to a change, e.g., an increase or decrease, of a cell associated activity particularly phosphatidylinositol turnover and phospholipase C activation. In one embodiment, the agent stimulates mACHR-6 polypeptide activity or mACHR-6 nucleic acid expression. Examples of such stimulatory agents include an active mACHR-6 polypeptide, a nucleic acid molecule encoding mACHR-6 that has been introduced into the cell, and a modulatory agent which stimulates mACHR-6 polypeptide activity or mACHR-6 nucleic acid expression and which is identified using the drug screening assays described herein. In another embodiment, the agent inhibits mACHR-6 polypeptide activity or mACHR-6 nucleic acid expression. Examples of such inhibitory agents include an antisense mACHR-6 nucleic acid molecule, an anti-mACHR-6 antibody, and a modulatory agent which inhibits mACHR-6 polypeptide activity or mACHR-6 nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant mACHR-6 polypeptide activity or mACHR-6 nucleic acid expression.

A nucleic acid molecule, a polypeptide, an mACHR-6 modulator, a compound etc. used in the methods of treatment can be incorporated into an appropriate pharmaceutical composition described herein and administered to the subject through a route which allows the molecule, polypeptide, modulator, or compound etc. to perform its intended function. Examples of routes of administration are also described herein under subsection IV.

d. Pharmacogenomics

Test/candidate compounds, or modulators which have a stimulatory or inhibitory effect on mACHR-6 activity (e.g., mACHR-6 gene expression) as identified by a screening assay described herein can be administered to individuals to treat (prophylactically or therapeutically) disorders (e.g., CNS disorders) associated with aberrant mACHR-6 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permit the selection of effective compounds (e.g., drugs) for prophylactic or therapeutic treatments based on a consideration of the individual's genotype. Such pharmacogenomics can further be used to determine appropriate dosages and therapeutic regimens. Accordingly, the activity of mACHR-6 polypeptide, expression of mACHR-6 nucleic acid, or mutation content of mACHR-6 genes in an individual can be determined to thereby select appropriate compound(s) for therapeutic or prophylactic treatment of the individual.

Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985 and Linder, M. W. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of mACHR-6 polypeptide, expression of mACHR-6 nucleic acid, or mutation content of mACHR-6 genes in an individual can be determined to thereby select appropriate agent(s) for therapeutic or prophylactic treatment of a subject. In addition, pharmacogenetic studies can be used to apply genotyping of polymorphic alleles encoding drug-metabolizing enzymes to the identification of a subject's drug responsiveness phenotype. This knowledge, when applied to dosing or drug selection, can avoid adverse reactions or therapeutic failure and thus enhance therapeutic or prophylactic efficiency when treating a subject with an mACHR-6 modulator, such as a modulator identified by one of the exemplary screening assays described herein.

e. Monitoring of Effects During Clinical Trials

Monitoring the influence of compounds (e.g., drugs) on the expression or activity of mACHR-6 (e.g., the ability to modulate the effects of acetylcholine on acetylcholine responsive cells) can be applied not only in basic drug screening, but also in clinical trials. For example, the effectiveness of an agent determined by a screening assay, as described herein, to increase mACHR-6 gene expression, polypeptide levels, or up-regulate mACHR-6 activity, can be monitored in clinical trails of subjects exhibiting decreased mACHR-6 gene expression, polypeptide levels, or down-regulated mACHR-6 activity. Alternatively, the effectiveness of an agent, determined by a screening assay, to decrease mACHR-6 gene expression, polypeptide levels, or down-regulate mACHR-6 activity, can be monitored in clinical trails of subjects exhibiting increased mACHR-6 gene expression, polypeptide levels, or up-regulated mACHR-6 activity. In such clinical trials, the expression or activity of mACHR-6 and, preferably, other genes which have been implicated in, for example, a nervous system related disorder can be used as a "read out" or markers of the acetylcholine responsiveness of a particular cell.

For example, and not by way of limitation, genes, including mACHR-6, which are modulated in cells by treatment with a compound (e.g., drug or small molecule) which modulates mACHR-6 activity (e.g., identified in a screening assay as described herein) can be identified. Thus, to study the effect of compounds on CNS disorders, for example, in a clinical trial, cells can be isolated and RNA prepared and analyzed for the levels of expression of mACHR-6 and other genes implicated in the disorder. The levels of gene expression (i.e., a gene expression pattern) can be quantified by Northern blot analysis or RT-PCR, as described herein, or alternatively by measuring the amount of polypeptide produced, by one of the methods described herein, or by measuring the levels of activity of mACHR-6 or other genes. In this way, the gene expression pattern can serve as a marker, indicative of the physiological response of the cells to the compound. Accordingly, this response state may be determined before, and at various points during, treatment of the individual with the compound.

In a preferred embodiment, the present invention provides a method for monitoring the effectiveness of treatment of a subject with a compound (e.g., an agonist, antagonist, peptidomimetic, polypeptide, peptide, nucleic acid, small molecule, or other drug candidate identified by the screening assays described herein) comprising the steps of (i) obtaining a pre-administration sample from a subject prior to administration of the compound; (ii) detecting the level of expression of an mACHR-6 polypeptide, mRNA, or genomic DNA in the preadministration sample; (iii) obtaining one or more post-administration samples from the subject; (iv) detecting the level of expression or activity of the mACHR-6 polypeptide, mRNA, or genomic DNA in the post-administration samples; (v) comparing the level of expression or activity of the mACHR-6 polypeptide, mRNA, or genomic DNA in the pre-administration sample with the mACHR-6 polypeptide, mRNA, or genomic DNA in the post administration sample or samples; and (vi) altering the administration of the compound to the subject accordingly. For example, increased administration of the compound may be desirable to increase the expression or activity of mACHR-6 to higher levels than detected, i.e., to increase the effectiveness of the agent. Alternatively, decreased administration of the agent may be desirable to decrease expression or activity of mACHR-6 to lower levels than detected, i.e. to decrease the effectiveness of the compound.

VI. Uses of Partial mACHR-6 Sequences

Portions or fragments of the cDNA sequences identified herein (and the corresponding complete gene sequences) can be used in numerous ways as polynucleotide reagents. For example, these sequences can be used to: (a) map their respective genes on a chromosome; and, thus, locate gene regions associated with genetic disease; (b) identify an individual from a minute biological sample (tissue typing); and (c) aid in forensic identification of a biological sample. These applications are described in the subsections below.

a. Chromosome Mapping

Once the sequence (or a portion of the sequence) of a gene has been isolated, this sequence can be used to map the location of the gene on a chromosome. This process is called chromosome mapping. Accordingly, portions or fragments of the mACHR-6, sequences, described herein, can be used to map the location of the mACHR-6 gene, respectively, on a chromosome. The mapping of the mACHR-6 sequence to chromosomes is an important first step in correlating these sequence with genes associated with disease.

Briefly, the mACHR-6 gene can be mapped to a chromosome by preparing PCR primers (preferably 15–25 bp in length) from the mACHR-6 sequence. Computer analysis of the mACHR-6, sequence can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the mACHR-6 sequence will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the mACHR-6 sequence to design oligonucleotide primers, sublocalization can be achieved with panels of fragments from specific chromosomes. Other mapping strategies which can similarly be used to map a mACHR-6 sequence to its chromosome include in situ hybridization (described in Fan, Y. et al. (1990) *PNAS,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York, 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the mACHR-6 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

b. Tissue Typing

The mACHR-6 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the mACHR-6 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The mACHR-6 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NOs:1 and 4, can comfortably provide positive individual identification with a panel of perhaps 10 to 1,000 primers which each yield a noncoding amplified sequence of 100 bases. If predicted coding sequences, such as those in SEQ ID NOs:3 and 6, are used, a more appropriate number of primers for positive individual identification would be 500–2,000.

If a panel of reagents from mACHR-6 sequences described herein is used to generate a unique identification database for an individual, those same reagents can later be used to identify tissue from that individual. Using the unique identification database, positive identification of the individual, living or dead, can be made from extremely small tissue samples.

c. Use of Partial mACHR-6 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to noncoding regions of SEQ ID NOs:1 and 4 are particularly appropriate for this use as greater numbers of polymorphisms occur in the noncoding regions, making it easier to differentiate individuals using this technique. Examples of polynucleotide reagents include the mACHR-6 sequences or portions thereof, e.g., fragments derived from the noncoding regions of SEQ ID NOs:1 and 5, having a length of at least 20 bases, preferably at least 30 bases.

The mACHR-6 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such mACHR-6 probes can be used to identify tissue by species and/or by organ type.

In a similar fashion, these reagents, e.g., mACHR-6 primers or probes can be used to screen tissue culture for contamination (i.e. screen for the presence of a mixture of different types of cells in a culture).

This invention is further illustrated by the following examples which should not be construed as limiting. The contents of all references, patent applications, patents, and published patent applications cited throughout this application are hereby incorporated by reference.

EXAMPLES

Example 1

Identification of Rat and human mACHR-6 cDNA

In this example, mACHR-6 nucleic acid molecules were identified by screening appropriate cDNA libraries. More specifically, a rat frontal cortex oligo dT-primed cDNA library was plated out and colonies picked into 96 well plates. The colonies were cultured, plasmids were prepared from each well, and the 5' end of each insert sequenced. After automated "trimming" of non-insert sequences, the nucleotide sequences were compared against the public protein databases using the BLAST sequence comparison program (BLASTN1.3MP, Altschul et al. (1990) *J. Mol. Biol.* 215:403). Upon review of the results from this sequence comparison, a single clone was identified, designated 84g5, whose highest similarity was with the rat muscarinic acetylcholine receptor M1 (mACHR M1; GenBank™ Accession Number P08482). The clone containing this sequence was recovered from the 96 well plate, plasmid was prepared using standard methods and the insert fully sequenced using standard "contigging" techniques. A repeat BLAST analysis using the entire insert sequence once again showed that the sequence in the protein database with the greatest similarity corresponded to GenBank™ Accession Number P08482. This sequence and the insert sequence were compared using the GAP program in (www.gcg.com) using a gap weight of 5.000 and a length weight of 0.100. The results showed a 27.97% identity and 49.01 % similarity between the two sequences with the insertion of 4 gaps for optimized sequence alignment. The alignment indicated that the 84g5 clone does not extend fully across the P08482 sequence, apparently missing approximately 30 amino acid residues at the N-terminal region of the molecule. BLAST analysis of public nucleotide databases revealed no equivalent human sequences. Only a single mouse EST was identified (GenBank™ Accession Number AA118949) which is similar to the 84g5 clone between residues 1101 and 1650.

The human mACHR-6 nucleic acid molecule was identified by screening a human cerebellum cDNA library using a NciI/NotI restriction fragment of the rat cDNA as a probe. BLAST analysis of protein and nucleic acid databases in the public domain again showed that the mACHR-6 nucleic acid molecule is most similar to mACHR M1 sequences. The alignments also revealed that mACHR-6 nucleic acid molecule encodes a full length ACHR polypeptide.

Example 2

Tissue Expression of the mACHR-6 Gene

Northern Analysis Using RNA from Human and Rat Tissue

Human brain multiple tissue northern (MTN) blots, human MTN 1, 11, and III blots, and rat MTN blots (Clontech, Palo Alto, Calif.), containing 2 μg of poly A+ RNA per lane were probed with the rat mACHR-6 nucleotide sequence (NciI/NotI restriction fragment). The filters were prehybridized in 10 ml of Express Hyb hybridization solution (Clontech, Palo Alto, Calif.) at 68° C. for 1 hour, after which 100 ng of $^{32}$P labeled probe was added. The probe was generated using the Stratagene Prime-It kit, Catalog Number 300392 (Clontech, Palo Alto, Calif.). Hybridization was allowed to proceed at 68° C. for approximately 2 hours. The filters were washed in a 0.05% SDS/2× SSC solution for 15 minutes at room temperature and then twice with a 0.1% SDS/0.1× SSC solution for 20 minutes at 5° C. and then exposed to autoradiography film overnight at –80° C. with one screen. The human tissues tested included: heart, brain (regions of the brain tested included cerebellum, corpus callosum, cerebral cortex, medulla, occipital pole, frontal lobe, temporal lobe, putamen, amygdala, caudate nucleus, hippocampus, substantia nigra, subthalamic nucleus and thalamus), placenta, lung, liver, skeletal muscle, kidney, pancreas, spleen, thymus, prostate, testis, ovary, small intestine, colon, peripheral blood leukocyte, stomach, thyroid, spinal cord, lymph node, trachea, adrenal gland and bone marrow. The rat tissues tested included: heart, brain, spleen, lung, liver, skeletal muscle, kidney, and testis.

There was a strong hybridization to human whole brain, the following human brain regions: cerebellum, corpus callosum, cerebral cortex, medulla, occipital pole, frontal lobe, temporal lobe, putamen, amygdala, caudate nucleus, hippocampus, substantia nigra, subthalamic nucleus and thalamus; and rat brain indicating that the approximately 3 kb mACHR-6 gene transcript is expressed in these tissues. There was also hybridization to human spinal cord.

In Situ Hybridization

For in situ analysis, the brain of an adult Sprague-Dawley rat was removed and frozen on dry ice. Ten-micrometer-thick coronal sections of the brain were postfixed with 4% formaldehyde in DEPC treated 1× phosphate-buffered saline at room temperature for 10 minutes before being rinsed twice in DEPC 1× phosphate-buffered saline and once in 0.1M triethanolamine-HCl (pH 8.0). Following incubation in 0.25% acetic anhydride-0.1M triethanolamine-HCl for 10 minutes, sections were rinsed in DEPC 2× SSC (1× SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled (5×10$^7$ cpm/ml) cRNA probes encoding a 474-bp fragment of the rat gene (generated with PCR primers F, 5'-CAAGAACCCTTTAAGCCAAG (SEQ ID NO:25), and R, 5' -GAAGAAGGTAACGCTGAGGA (SEQ ID NO:26)) and a 529-bp fragment of the rat gene (generated with PCR primers F, 5'-CAGAACCCCCACCAGATGCC (SEQ ID NO:27), and R, 5'-TAGTGGCACAGTGGGTAGAG (SEQ ID NO:28)). Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2× SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2× SSC at room temperature, washed with 2× SSC at 50° C. for 1 hour, washed with 0.2× SSC at 55° C. for 1 hour, and 0.2× SSC at 60° C. for 1 hour. Sections were then dehydrated rapidly through serial ethanol-0.3M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Significant hybridization was seen in a number of brain regions. These included the cortex, caudate putamen, hippocampus, thalamus and cerebellum. Analysis of these regions at high magnification showed that significant labeling was seen over the cell bodies of neurons.

Example 3

Expression of Recombinant mACHR-6 Polypeptide in Bacterial Cells

In this example, mACHR-6 is expressed as a recombinant glutathione-S-transferase (GST) fusion polypeptide in *E. coli* and the fusion polypeptide is isolated and characterized. Specifically, mACHR-6 is fused to GST and this fusion polypeptide is expressed in *E. coli*, e.g., strain PEB199. As the human and rat mACHR-6 polypeptides are predicted to be approximately 51.3 kDa, and 41.6 kDa, respectively, and GST is predicted to be 26 kDa, the fusion polypeptides are predicted to be approximately 77.3 kDa and 67.6 kDa, respectively, in molecular weight. Expression of the GST-mACHR-6 fusion polypeptide in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4
Expression of Recombinant mACHR-6 Polypeptide in COS Cells

To express the mACHR-6 gene in COS cells, the pcDNA/Amp vector by Invitrogen orporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire mACHR-6 polypeptide and a HA tag (Wilson et al. (1984) *Cell* 37:767) fused in-frame to its 3' end of the fragment is cloned into the polylinker region of the vector, thereby placing the expression of the recombinant polypeptide under the control of the CMV promoter.

To construct the plasmid, the mACHR-6 DNA sequence is amplified by PCR using two primers. The 5' primer contains the restriction site of interest followed by approximately twenty nucleotides of the mACHR-6 coding sequence starting from the initiation codon; the 3' end sequence contains complementary sequences to the other restriction site of interest, a translation stop codon, the HA tag and the last 20 nucleotides of the mACHR-6 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the mACHR-6 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the mACHR-6-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the mACHR-6 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the mACHR-6 coding sequence is cloned directly into the polylinker of the pcDNA/Amp vector using the appropriate restriction sites. The resulting plasmid is transfected into COS cells in the manner described above, and the expression of the mACHR-6 polypeptide is detected by radiolabelling and immunoprecipitation using an mACHR-6 specific monoclonal antibody

Example 5
Characterization of the Human and Rat mACHR-6 Polypeptides

In this example, the amino acid sequences of the human and the rat mACHR-6 polypeptides were compared to amino acid sequences of known polypeptides and various motifs were identified.

The human mACHR-6 polypeptide, the amino acid sequence of which is shown in FIG. 1 (SEQ ID NO:2), is a novel polypeptide which includes 445 amino acid residues.

The human mACHR-6 polypeptide contains seven transmembrane domains between amino acid residues 34–59 (SEQ ID NO:7), 73–91 (SEQ ID NO:8), 109–1 30 (SEQ ID NO:9), 152–174 (SEQ ID NO:10), 197–219 (SEQ ID NO:11), 360–380 (SEQ ID NO:12), and 396–416 20 (SEQ ID NO:13). The nucleotide sequence of the human mACHR-6 was used as a database query using the BLASTN program (BLASTN1.3MP, Altschul et al. (1990) *J. Mol. Biol.* 215:403). The closest hits were human, rat, mouse and pig mACHR M1 (GenBank™ Accession Numbers P11229, P08482, P12657, and P04761, respectively). The highest similarity is 32/70 amino acid identities.

The rat mACHR-6 polypeptide, the amino acid sequence of which is shown in FIG. 2 (SEQ ID NO:5), is a novel polypeptide which includes at least about 362 amino acid residues. The partial rat mACHR-6 polypeptide contains six transmembrane domains between amino acid residues 1–8 (SEQ ID NO:14), 26–47 (SEQ ID NO:15), 69–91 (SEQ ID NO:16), 114–136 (SEQ ID NO:17), 277–297 (SEQ ID NO:18), and 313–333 (SEQ ID NO:19), which correspond to the human mACHR-6 polypeptide transmembrane domains 2–7 (SEQ ID NOs:9–13). Transmembrane domain 2 (SEQ ID NO:14) of the rat mACHR-6 polypeptide is partial and transmembrane domain 1 of the rat mACHR-6 polypeptide is missing. Based on the overall identity between the rat and the human mACHR-6 polypeptides, the rat transmembrane domain 1 is expected to be at least about 50% homologous to the human transmembrane domain 1 (SEQ ID NO:7). The nucleotide sequence of the rat mACHR-6 was used as a database query using the BLASTN program (BLASTN1.3MP, Altschul et al. (1990) *J. Mol. Biol.* 215:403). The closest hits were human, rat, mouse and pig mACHR M1 (GenBank™ Accession Numbers P11229, P08482, P12657, and P04761, respectively). The highest similarity is 33/70 amino acid identities. Hydropathy plots indicated that the transmembrane domains of the rat mACHR-6 polypeptide are similar to those of the rat mACHR M1. The cysteines (residues 63 and 44 of SEQ ID NO:5) that give rise to intramolecular disulfide bonds are also conserved.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence selected from the group consisting of:
   a) a nucleotide sequence which encodes a polypeptide comprising the amino acid sequence of SEQ ID NO:2;
   b) a nucleotide sequence which encodes a polypeptide comprising the amino acid sequence of SEQ ID NO:5;
   c) a nucleotide sequence which encodes a naturally occurring allelic variant of a polypeptide comprising the amino acid sequence of SEQ ID NO;2, wherein the nucleotide sequence hybridizes to a nucleic acid molecule comprising SEQ ID NO: 1 under stringent conditions;

d) a nucleotide sequence which encodes a naturally occurring allelic variant of a polypeptide comprising the amino acid sequence of SEQ ID NO:5, wherein the nucleotide sequence hybridizes to a nucleic acid molecule comprising SEQ ID NO:4 under stringent conditions;

e) a nucleotide sequence which encodes a naturally occurring allelic variant of a polypeptide comprising the amino acid sequence of SEQ ID NO:2, wherein the nucleotide sequence hybridizes to a nucleic acid molecule comprising SEQ ID NO:3 under stringent conditions; and f) a nucleotide sequence which encodes a naturally occurring allelic variant of a polypeptide comprising the amino acid sequence of SEQ ID NO:5, wherein the nucleotide sequence hybridizes to a nucleic acid molecule comprising SEQ ID NO:6 under stringent conditions.

2. An isolated nucleic acid molecule comprising a nucleotide sequence which is selected from the group consisting of:

a) a nucleotide sequence which consists of the coding region of SEQ ID NO:1;

b) a nucleotide sequence which consists of the coding region of SEQ ID NO:4;

c) a nucleotide sequence which encodes a polypeptide comprising the amino acid sequence of SEQ ID NO:7;

d) a nucleotide sequence which encodes a polypeptide comprising the amino acid sequence of SEQ ID NO:8;

e) a nucleotide sequence which encodes a polypeptide comprising the amino acid sequence of SEQ ID NO:9;

f) a nucleotide sequence which encodes a polypeptide comprising the amino acid sequence of SEQ ID NO:10;

g) a nucleotide sequence which encodes a polypeptide comprising the amino acid sequence of SEQ ID NO:11;

h) a nucleotide sequence which encodes a polypeptide comprising the amino acid sequence of SEQ ID NO:12;

i) a nucleotide sequence which encodes a polypeptide comprising The amino acid sequence of SEQ ID NO:13;

j) the nucleotide sequence of SEQ ID NO:1;

k) the nucleotide sequence of SEQ ID NO:3;

l) the nucleotide sequence of SEQ ID NO:4; and m) the nucleotide sequence of SEQ ID NO:6.

3. A vector comprising the nucleic acid molecule of claim 1 or 2.

4. An isolated nucleic acid molecule comprising the nucleic acid molecule of claim 1 or 2 and a nucleic acid sequence encoding a heterologous polypeptide.

5. An isolated host cell which is transfected with the nucleic acid molecule of claim 1 or 2.

6. The host cell of claim 5 which is a mammalian host cell.

7. A method for expressing a polypeptide comprising culturing the isolated host cell of claim 5 under conditions in which the nucleic acid molecule is expressed, thereby expressing said polypeptide.

8. A method for producing an isolated polypeptide, comprising culturing the isolated host cell of claim 5 under conditions in which the nucleic acid molecule is expressed and isolating said polypeptide from the culture medium.

9. An isolated non-human mammalian host cell which is transfected with the nucleic acid molecule of claim 1 or 2.

10. A kit comprising a nucleic acid molecule of claim 1 or 2 and instructions for use in detecting the presence of a nucleic acid molecule which hybridizes under stringent conditions to the nucleic acid molecule of claim 1 or 2.

11. A composition comprising the nucleic acid molecule of claim 1 or 2 and a carrier.

12. An isolated nucleic acid molecule comprising a nucleotide sequence which encodes a polypeptide comprising the amino acid sequence of SEQ ID NO:2.

13. An isolated nucleic acid molecule comprising a nucleotide sequence which encodes a polypeptide comprising the amino acid sequence of SEQ ID NO:5.

14. An isolated nucleic acid molecule comprising a nucleotide sequence which encodes a naturally occurring allelic variant of a polypeptide comprising the amino acid sequence of SEQ ID NO:2, wherein the nucleotide sequence hybridizes to a nucleic acid molecule comprising SEQ ID NO:1 under stringent conditions.

15. An isolated nucleic acid molecule comprising a nucleotide sequence which encodes a naturally occurring allelic variant of a polypeptide comprising the amino acid sequence of SEQ ID NO:5, wherein the nucleotide sequence hybridizes to a nucleic acid molecule comprising SEQ ID NO:4 under stringent conditions.

16. An isolated nucleic acid molecule comprising the nucleotide sequence of SEQ ID NO:1.

17. An isolated nucleic acid molecule comprising the nucleotide sequence of SEQ ID NO:3.

18. An isolated nucleic acid molecule comprising a nucleotide sequence encoding a polypeptide which is at least 90 percent identical to the amino acid sequence of SEQ ID NO:2 or 5, wherein said percent identity is calculated using the GAP program in the GCG software package, using a gap weight of 5,000 and a length weight of 0.100.

19. An isolated nucleic acid molecule comprising a nucleotide sequence encoding a polypeptide, wherein said nucleotide sequence is at least 90 percent identical to the nucleotide sequence of SEQ ID NO:1 or 4, and wherein said percent identity is calculated using the GAP program in the GCG software package, using a gap weight of 5,000 and a length weight of 0.100.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 2689 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 291..1625

( x i ) SEQUENCE DESCRIPTION: SEQ ID NO:1:

```
GTCGACCCAC GCGTCCGCGC ACCGGCAGCG GCTCAGGCTC CGGCTCCTCT CCCGCTGCAG      60

CAGCCGCGCT GCCGGCCCCA CTGGGCTCGG ATCCGGCCCC GGCCCCCTCG GCACCGCCTG     120

CTCTGGCCCC GGCCCCGGCC CCGCGGACCA TGCGCTGGGC GCCCCCAGGG GAACCCGACC     180

CGGCCAAGGG CCCGCAAAGA CGAGGCTCCC GGGCCGGGGC CCCTCCCGGC CGCCCAGCTC     240

TCGGCCGGCG CCCTGCCCCG CGTCCCGGAG CCGCGTGAGC CTGCGGGGCC ATG GAG        296
                                                       Met Glu
                                                         1

CGC GCG CCG CCC GAC GGG CCG CTG AAC GCT TCG GGG GCG CTG GCG GGC       344
Arg Ala Pro Pro Asp Gly Pro Leu Asn Ala Ser Gly Ala Leu Ala Gly
         5                  10                  15

GAG GCG GCG GCG GCG GGC GGG GCG CGC GGC TTC TCG GCA GCC TGG ACC       392
Glu Ala Ala Ala Ala Gly Gly Ala Arg Gly Phe Ser Ala Ala Trp Thr
     20                  25                  30

GCG GTG CTG GCC GCG CTC ATG GCG CTG CTC ATC GTG GCC ACG GTG CTG       440
Ala Val Leu Ala Ala Leu Met Ala Leu Leu Ile Val Ala Thr Val Leu
 35                  40                  45                  50

GGC AAC GCG CTG GTC ATG CTC GCC TTC GTG GCC GAC TCG AGC CTC CGC       488
Gly Asn Ala Leu Val Met Leu Ala Phe Val Ala Asp Ser Ser Leu Arg
                 55                  60                  65

ACC CAG AAC AAC TTC TTC CTG CTC AAC CTC GCC ATC TCC GAC TTC CTC       536
Thr Gln Asn Asn Phe Phe Leu Leu Asn Leu Ala Ile Ser Asp Phe Leu
                 70                  75                  80

GTC GGC GCC TTC TGC ATC CCA CTG TAT GTA CCC TAC GTG CTG ACA GGC       584
Val Gly Ala Phe Cys Ile Pro Leu Tyr Val Pro Tyr Val Leu Thr Gly
             85                  90                  95

CGC TGG ACC TTC GGC CGG GGC CTC TGC AAG CTG TGG CTG GTA GTG GAC       632
Arg Trp Thr Phe Gly Arg Gly Leu Cys Lys Leu Trp Leu Val Val Asp
100                 105                 110

TAC CTG CTG TGC ACC TCC TCT GCC TTC AAC ATC GTG CTC ATC AGC TAC       680
Tyr Leu Leu Cys Thr Ser Ser Ala Phe Asn Ile Val Leu Ile Ser Tyr
115                 120                 125                 130

GAC CGC TTC CTG TCG GTC ACC CGA GCG GTC TCA TAC CGG GCC CAG CAG       728
Asp Arg Phe Leu Ser Val Thr Arg Ala Val Ser Tyr Arg Ala Gln Gln
                135                 140                 145

GGT GAC ACG CGG CGG GCA GTG CGG AAG ATG CTG CTG GTG TGG GTG CTG       776
Gly Asp Thr Arg Arg Ala Val Arg Lys Met Leu Leu Val Trp Val Leu
                150                 155                 160

GCC TTC CTG CTG TAC GGA CCA GCC ATC CTG AGC TGG GAG TAC CTG TCC       824
Ala Phe Leu Leu Tyr Gly Pro Ala Ile Leu Ser Trp Glu Tyr Leu Ser
            165                 170                 175
```

```
GGG GGC AGC TCC ATC CCC GAG GGC CAC TGC TAT GCC GAG TTC TTC TAC        872
Gly Gly Ser Ser Ile Pro Glu Gly His Cys Tyr Ala Glu Phe Phe Tyr
180             185                 190

AAC TGG TAC TTC CTC ATC ACG GCT TCC ACC CTG GAG TTC TTT ACG CCC        920
Asn Trp Tyr Phe Leu Ile Thr Ala Ser Thr Leu Glu Phe Phe Thr Pro
195             200                 205                     210

TTC CTC AGC GTC ACC TTC TTT AAC CTC AGC ATC TAC CTG AAC ATC CAG        968
Phe Leu Ser Val Thr Phe Phe Asn Leu Ser Ile Tyr Leu Asn Ile Gln
            215                 220                 225

AGG CGC ACC CGC CTC CGG CTG GAT GGG GCT CGA GAG GCA GCC GGC CCC       1016
Arg Arg Thr Arg Leu Arg Leu Asp Gly Ala Arg Glu Ala Ala Gly Pro
            230                 235                 240

GAG CCC CCT CCC GAG GCC CAG CCC TCA CCA CCC CCA CCG CCT GGC TGC       1064
Glu Pro Pro Pro Glu Ala Gln Pro Ser Pro Pro Pro Pro Pro Gly Cys
        245                 250                 255

TGG GGC TGC TGG CAG AAG GGG CAC GGG GAG GCC ATG CCG CTG CAC AGG       1112
Trp Gly Cys Trp Gln Lys Gly His Gly Glu Ala Met Pro Leu His Arg
    260                 265                 270

TAT GGG GTG GGT GAG GCG GCC GTA GGC GCT GAG GCC GGG GAG GCG ACC       1160
Tyr Gly Val Gly Glu Ala Ala Val Gly Ala Glu Ala Gly Glu Ala Thr
275             280                 285                     290

CTC GGG GGT GGC GGT GGG GGC GGC TCC GTG GCT TCA CCC ACC TCC AGC       1208
Leu Gly Gly Gly Gly Gly Gly Gly Ser Val Ala Ser Pro Thr Ser Ser
                295                 300                 305

TCC GGC AGC TCC TCG AGG GGC ACT GAG AGG CCG CGC TCA CTC AAG AGG       1256
Ser Gly Ser Ser Ser Arg Gly Thr Glu Arg Pro Arg Ser Leu Lys Arg
            310                 315                 320

GGC TCC AAG CCG TCG GCG TCC TCG GCC TCA CTG GAG AAG CGC ATG AAG       1304
Gly Ser Lys Pro Ser Ala Ser Ser Ala Ser Leu Glu Lys Arg Met Lys
        325                 330                 335

ATG GTG TCC CAG AGC TTC ACC CAG CGC TTT CGG CTG TCT CGG GAC AGG       1352
Met Val Ser Gln Ser Phe Thr Gln Arg Phe Arg Leu Ser Arg Asp Arg
340                 345                 350

AAA GTG GCC AAG TCG CTG GCC GTC ATC GTG AGC ATC TTT GGG CTC TGC       1400
Lys Val Ala Lys Ser Leu Ala Val Ile Val Ser Ile Phe Gly Leu Cys
355             360                 365                     370

TGG GCC CCA TAC ACG CTG CTG ATG ATC ATC CGG GCC GCC TGC CAT GGC       1448
Trp Ala Pro Tyr Thr Leu Leu Met Ile Ile Arg Ala Ala Cys His Gly
            375                 380                 385

CAC TGC GTC CCT GAC TAC TGG TAC GAA ACC TCC TTC TGG CTC CTG TGG       1496
His Cys Val Pro Asp Tyr Trp Tyr Glu Thr Ser Phe Trp Leu Leu Trp
        390                 395                 400

GCC AAC TCG GCT GTC AAC CCT GTC CTC TAC CCT CTG TGC CAC CAC AGC       1544
Ala Asn Ser Ala Val Asn Pro Val Leu Tyr Pro Leu Cys His His Ser
    405                 410                 415

TTC CGC CGG GCC TTC ACC AAG CTG CTC TGC CCC CAG AAG CTC AAA ATC       1592
Phe Arg Arg Ala Phe Thr Lys Leu Leu Cys Pro Gln Lys Leu Lys Ile
420                 425                 430

CAG CCC CAC AGC TCC CTG GAG CAC TGC TGG AAG TGAGTGGCCC ACCAGAGCCT     1645
Gln Pro His Ser Ser Leu Glu His Cys Trp Lys
435                 440                 445

CCCTCAGCCA CGCCTCTCTC AGCCCAGGTC TCCTGGGCAT CTGGCCCTGC TGCCCCCTAC     1705

CCGGCTCGTT CCCCCAGGGG TGAGCCCGC CGTGTCTGTG GCCCTCTCTT AATGCCACGG      1765

CAGCCACCCT GCCATGGAGG CGCCTTCCTG GGTTGGCCAG AGGGCCCCTC ACTGGCTGGA     1825

CTGGAGGCTG GGTGGCCGGC CCTGCCCCCC ACATTCTGGC TCCACCGGGA GGGACAGTCT    1885

GGAGGTCCCA GACATGCTGC CCACCCCCTG CTGGTGCCCA CCCTTCGCAG TTACTGGTTG    1945

GTGTTCTTCC CAAAGCAAGC ACCTGGGTGT GCTCCAGGCT TCCTGCCCTA GCAGTTTGCC    2005
```

-continued

```
TCTGCACGTG CACACACCTG CACACCCCTG CACACACCTG CACACCGTCC CTCTCCCCGG      2065

ACAAGCCCAG GACACTGCCT TTGCTGCCTT CTGTCTCTTG CATAAGCCTC AGGCCTGGCC      2125

CTTTCACCCC TCTTCCCACC AACTCTCTCT GCCCCAAAA GTGTCAAGGG GCCCTAGGAA       2185

CCTCGAAGCT GTTCTCTGCT TTTCCATTCT GGGTGTTTTC AGAAAGATGA AGAAGAAAAC     2245

ATGTCTGTGA ACTTGATGTT CCTGGGATGT TTAATCAAGA GAGACAAAAT TGCTGAGGAG      2305

CTCAGGGCTG GATTGGCAGG TGTGGGCTCC CACGCCCTCC TCCCTCCGCT AAGGCTTCCG      2365

GCTGAGCTGT GCCAGCTGCT TCTGCCCACC CCGCCTCTGG GCTCACACCA GCCCTGGTGG     2425

CCAAGCCTGC CCCGGCCACT CTGTTTGCTC ACCCAGGACC TCTGGGGGTT GTTGGGAGGA     2485

GGGGGCCCGG CTGGGCCCGA GGGTCCCAAG GCGTGCAGGG GCGGTCCAGA GGAGGTGCCC     2545

GGGCAGGGGC CGCTTCGCCA TGTGCTGTGC ACCCGTGCCA CGCGCTCTGC ATGCTCCTCT      2605

GCCTGTGCCC GCTGCGCTGC CCTGCAAACC GTGAGGTCAC AATAAAGTGT ATTTTTTAA      2665

AAAAAAAAAA AAAAGGGCGG CCGC                                             2689
```

( 2 ) INFORMATION FOR SEQ ID NO:2:

( i ) SEQUENCE CHARACTERISTICS:
        ( A ) LENGTH: 445 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Arg Ala Pro Pro Asp Gly Pro Leu Asn Ala Ser Gly Ala Leu
 1               5                  10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
            35                  40                  45

Val Leu Gly Asn Ala Leu Val Met Leu Ala Phe Val Ala Asp Ser Ser
        50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
            115                 120                 125

Ser Tyr Asp Arg Phe Leu Ser Val Thr Arg Ala Val Ser Tyr Arg Ala
        130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
        210                 215                 220

Ile Gln Arg Arg Thr Arg Leu Arg Leu Asp Gly Ala Arg Glu Ala Ala
225                 230                 235                 240
```

```
Gly  Pro  Glu  Pro  Pro  Pro  Glu  Ala  Gln  Pro  Ser  Pro  Pro  Pro  Pro  Pro
               245                      250                      255

Gly  Cys  Trp  Gly  Cys  Trp  Gln  Lys  Gly  His  Gly  Glu  Ala  Met  Pro  Leu
               260                      265                      270

His  Arg  Tyr  Gly  Val  Gly  Glu  Ala  Ala  Val  Gly  Ala  Glu  Ala  Gly  Glu
               275                      280                      285

Ala  Thr  Leu  Gly  Gly  Gly  Gly  Gly  Gly  Ser  Val  Ala  Ser  Pro  Thr
          290                      295                      300

Ser  Ser  Ser  Gly  Ser  Ser  Ser  Arg  Gly  Thr  Glu  Arg  Pro  Arg  Ser  Leu
305                      310                      315                      320

Lys  Arg  Gly  Ser  Lys  Pro  Ser  Ala  Ser  Ser  Ala  Ser  Leu  Glu  Lys  Arg
               325                      330                      335

Met  Lys  Met  Val  Ser  Gln  Ser  Phe  Thr  Gln  Arg  Phe  Arg  Leu  Ser  Arg
               340                      345                      350

Asp  Arg  Lys  Val  Ala  Lys  Ser  Leu  Ala  Val  Ile  Val  Ser  Ile  Phe  Gly
               355                      360                      365

Leu  Cys  Trp  Ala  Pro  Tyr  Thr  Leu  Leu  Met  Ile  Ile  Arg  Ala  Ala  Cys
          370                      375                      380

His  Gly  His  Cys  Val  Pro  Asp  Tyr  Trp  Tyr  Glu  Thr  Ser  Phe  Trp  Leu
385                      390                      395                      400

Leu  Trp  Ala  Asn  Ser  Ala  Val  Asn  Pro  Val  Leu  Tyr  Pro  Leu  Cys  His
               405                      410                      415

His  Ser  Phe  Arg  Arg  Ala  Phe  Thr  Lys  Leu  Leu  Cys  Pro  Gln  Lys  Leu
               420                      425                      430

Lys  Ile  Gln  Pro  His  Ser  Ser  Leu  Glu  His  Cys  Trp  Lys
               435                      440                      445
```

( 2 ) INFORMATION FOR SEQ ID NO:3:

( i ) SEQUENCE CHARACTERISTICS:
        ( A ) LENGTH: 1335 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1335

( x i ) SEQUENCE DESCRIPTION: SEQ ID NO:3:

```
ATG  GAG  CGC  GCG  CCG  CCC  GAC  GGG  CCG  CTG  AAC  GCT  TCG  GGG  GCG  CTG      48
Met  Glu  Arg  Ala  Pro  Pro  Asp  Gly  Pro  Leu  Asn  Ala  Ser  Gly  Ala  Leu
 1              5                        10                       15

GCG  GGC  GAG  GCG  GCG  GCG  GCG  GGC  GGG  GCG  CGC  GGC  TTC  TCG  GCA  GCC      96
Ala  Gly  Glu  Ala  Ala  Ala  Ala  Gly  Gly  Ala  Arg  Gly  Phe  Ser  Ala  Ala
               20                       25                       30

TGG  ACC  GCG  GTG  CTG  GCC  GCG  CTC  ATG  GCG  CTG  CTC  ATC  GTG  GCC  ACG     144
Trp  Thr  Ala  Val  Leu  Ala  Ala  Leu  Met  Ala  Leu  Leu  Ile  Val  Ala  Thr
               35                       40                       45

GTG  CTG  GGC  AAC  GCG  CTG  GTC  ATG  CTC  GCC  TTC  GTG  GCC  GAC  TCG  AGC     192
Val  Leu  Gly  Asn  Ala  Leu  Val  Met  Leu  Ala  Phe  Val  Ala  Asp  Ser  Ser
          50                       55                       60

CTC  CGC  ACC  CAG  AAC  AAC  TTC  TTC  CTG  CTC  AAC  CTC  GCC  ATC  TCC  GAC     240
Leu  Arg  Thr  Gln  Asn  Asn  Phe  Phe  Leu  Leu  Asn  Leu  Ala  Ile  Ser  Asp
 65                      70                       75                       80

TTC  CTC  GTC  GGC  GCC  TTC  TGC  ATC  CCA  CTG  TAT  GTA  CCC  TAC  GTG  CTG     288
Phe  Leu  Val  Gly  Ala  Phe  Cys  Ile  Pro  Leu  Tyr  Val  Pro  Tyr  Val  Leu
               85                       90                       95
```

| | | | | | | | | | | | | | | | | |
|---|---|---|---|---|---|---|---|---|---|---|---|---|---|---|---|---|
| ACA | GGC | CGC | TGG | ACC | TTC | GGC | CGG | GGC | CTC | TGC | AAG | CTG | TGG | CTG | GTA | 336 |
| Thr | Gly | Arg | Trp | Thr | Phe | Gly | Arg | Gly | Leu | Cys | Lys | Leu | Trp | Leu | Val | |
| | | | 100 | | | | 105 | | | | | 110 | | | | |
| GTG | GAC | TAC | CTG | CTG | TGC | ACC | TCC | TCT | GCC | TTC | AAC | ATC | GTG | CTC | ATC | 384 |
| Val | Asp | Tyr | Leu | Leu | Cys | Thr | Ser | Ser | Ala | Phe | Asn | Ile | Val | Leu | Ile | |
| | | 115 | | | | | 120 | | | | | 125 | | | | |
| AGC | TAC | GAC | CGC | TTC | CTG | TCG | GTC | ACC | CGA | GCG | GTC | TCA | TAC | CGG | GCC | 432 |
| Ser | Tyr | Asp | Arg | Phe | Leu | Ser | Val | Thr | Arg | Ala | Val | Ser | Tyr | Arg | Ala | |
| | 130 | | | | | 135 | | | | | 140 | | | | | |
| CAG | CAG | GGT | GAC | ACG | CGG | CGG | GCA | GTG | CGG | AAG | ATG | CTG | CTG | GTG | TGG | 480 |
| Gln | Gln | Gly | Asp | Thr | Arg | Arg | Ala | Val | Arg | Lys | Met | Leu | Leu | Val | Trp | |
| 145 | | | | | 150 | | | | | 155 | | | | | 160 | |
| GTG | CTG | GCC | TTC | CTG | CTG | TAC | GGA | CCA | GCC | ATC | CTG | AGC | TGG | GAG | TAC | 528 |
| Val | Leu | Ala | Phe | Leu | Leu | Tyr | Gly | Pro | Ala | Ile | Leu | Ser | Trp | Glu | Tyr | |
| | | | | 165 | | | | | 170 | | | | | 175 | | |
| CTG | TCC | GGG | GGC | AGC | TCC | ATC | CCC | GAG | GGC | CAC | TGC | TAT | GCC | GAG | TTC | 576 |
| Leu | Ser | Gly | Gly | Ser | Ser | Ile | Pro | Glu | Gly | His | Cys | Tyr | Ala | Glu | Phe | |
| | | | 180 | | | | | 185 | | | | | 190 | | | |
| TTC | TAC | AAC | TGG | TAC | TTC | CTC | ATC | ACG | GCT | TCC | ACC | CTG | GAG | TTC | TTT | 624 |
| Phe | Tyr | Asn | Trp | Tyr | Phe | Leu | Ile | Thr | Ala | Ser | Thr | Leu | Glu | Phe | Phe | |
| | | 195 | | | | | 200 | | | | | 205 | | | | |
| ACG | CCC | TTC | CTC | AGC | GTC | ACC | TTC | TTT | AAC | CTC | AGC | ATC | TAC | CTG | AAC | 672 |
| Thr | Pro | Phe | Leu | Ser | Val | Thr | Phe | Phe | Asn | Leu | Ser | Ile | Tyr | Leu | Asn | |
| | 210 | | | | | 215 | | | | | 220 | | | | | |
| ATC | CAG | AGG | CGC | ACC | CGC | CTC | CGG | CTG | GAT | GGG | GCT | CGA | GAG | GCA | GCC | 720 |
| Ile | Gln | Arg | Arg | Thr | Arg | Leu | Arg | Leu | Asp | Gly | Ala | Arg | Glu | Ala | Ala | |
| 225 | | | | | 230 | | | | | 235 | | | | | 240 | |
| GGC | CCC | GAG | CCC | CCT | CCC | GAG | GCC | CAG | CCC | TCA | CCA | CCC | CCA | CCG | CCT | 768 |
| Gly | Pro | Glu | Pro | Pro | Pro | Glu | Ala | Gln | Pro | Ser | Pro | Pro | Pro | Pro | Pro | |
| | | | | 245 | | | | | 250 | | | | | 255 | | |
| GGC | TGC | TGG | GGC | TGC | TGG | CAG | AAG | GGG | CAC | GGG | GAG | GCC | ATG | CCG | CTG | 816 |
| Gly | Cys | Trp | Gly | Cys | Trp | Gln | Lys | Gly | His | Gly | Glu | Ala | Met | Pro | Leu | |
| | | | 260 | | | | | 265 | | | | | 270 | | | |
| CAC | AGG | TAT | GGG | GTG | GGT | GAG | GCG | GCC | GTA | GGC | GCT | GAG | GCC | GGG | GAG | 864 |
| His | Arg | Tyr | Gly | Val | Gly | Glu | Ala | Ala | Val | Gly | Ala | Glu | Ala | Gly | Glu | |
| | | 275 | | | | | 280 | | | | | 285 | | | | |
| GCG | ACC | CTC | GGG | GGT | GGC | GGT | GGG | GGC | GGC | TCC | GTG | GCT | TCA | CCC | ACC | 912 |
| Ala | Thr | Leu | Gly | Gly | Gly | Gly | Gly | Gly | Gly | Ser | Val | Ala | Ser | Pro | Thr | |
| | 290 | | | | | 295 | | | | | 300 | | | | | |
| TCC | AGC | TCC | GGC | AGC | TCC | TCG | AGG | GGC | ACT | GAG | AGG | CCG | CGC | TCA | CTC | 960 |
| Ser | Ser | Ser | Gly | Ser | Ser | Ser | Arg | Gly | Thr | Glu | Arg | Pro | Arg | Ser | Leu | |
| 305 | | | | | 310 | | | | | 315 | | | | | 320 | |
| AAG | AGG | GGC | TCC | AAG | CCG | TCG | GCG | TCC | TCG | GCC | TCA | CTG | GAG | AAG | CGC | 1008 |
| Lys | Arg | Gly | Ser | Lys | Pro | Ser | Ala | Ser | Ser | Ala | Ser | Leu | Glu | Lys | Arg | |
| | | | | 325 | | | | | 330 | | | | | 335 | | |
| ATG | AAG | ATG | GTG | TCC | CAG | AGC | TTC | ACC | CAG | CGC | TTT | CGG | CTG | TCT | CGG | 1056 |
| Met | Lys | Met | Val | Ser | Gln | Ser | Phe | Thr | Gln | Arg | Phe | Arg | Leu | Ser | Arg | |
| | | | 340 | | | | | 345 | | | | | 350 | | | |
| GAC | AGG | AAA | GTG | GCC | AAG | TCG | CTG | GCC | GTC | ATC | GTG | AGC | ATC | TTT | GGG | 1104 |
| Asp | Arg | Lys | Val | Ala | Lys | Ser | Leu | Ala | Val | Ile | Val | Ser | Ile | Phe | Gly | |
| | | 355 | | | | | 360 | | | | | 365 | | | | |
| CTC | TGC | TGG | GCC | CCA | TAC | ACG | CTG | CTG | ATG | ATC | ATC | CGG | GCC | GCC | TGC | 1152 |
| Leu | Cys | Trp | Ala | Pro | Tyr | Thr | Leu | Leu | Met | Ile | Ile | Arg | Ala | Ala | Cys | |
| | 370 | | | | | 375 | | | | | 380 | | | | | |
| CAT | GGC | CAC | TGC | GTC | CCT | GAC | TAC | TGG | TAC | GAA | ACC | TCC | TTC | TGG | CTC | 1200 |
| His | Gly | His | Cys | Val | Pro | Asp | Tyr | Trp | Tyr | Glu | Thr | Ser | Phe | Trp | Leu | |
| 385 | | | | | 390 | | | | | 395 | | | | | 400 | |
| CTG | TGG | GCC | AAC | TCG | GCT | GTC | AAC | CCT | GTC | CTC | TAC | CCT | CTG | TGC | CAC | 1248 |
| Leu | Trp | Ala | Asn | Ser | Ala | Val | Asn | Pro | Val | Leu | Tyr | Pro | Leu | Cys | His | |
| | | | | 405 | | | | | 410 | | | | | 415 | | |

| | | | | | | | | | | | | | | |
|---|---|---|---|---|---|---|---|---|---|---|---|---|---|---|
| CAC | AGC | TTC | CGC | CGG | GCC | TTC | ACC | AAG | CTG | CTC | TGC | CCC | CAG | AAG | CTC | 1296
| His | Ser | Phe | Arg | Arg | Ala | Phe | Thr | Lys | Leu | Leu | Cys | Pro | Gln | Lys | Leu |
| | | | 420 | | | | 425 | | | | | 430 | | | |

| AAA | ATC | CAG | CCC | CAC | AGC | TCC | CTG | GAG | CAC | TGC | TGG | AAG | 1335
| Lys | Ile | Gln | Pro | His | Ser | Ser | Leu | Glu | His | Cys | Trp | Lys |
| | | 435 | | | | | 440 | | | | | 445 |

( 2 ) INFORMATION FOR SEQ ID NO:4:

( i ) SEQUENCE CHARACTERISTICS:
        ( A ) LENGTH: 2218 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 119..1204

( x i ) SEQUENCE DESCRIPTION: SEQ ID NO:4:

| GGT | GCC | TTC | TGC | ATC | CCA | TTG | TAC | GTA | CCC | TAT | GTG | CTG | ACC | GGC | CGT | 48
|---|---|---|---|---|---|---|---|---|---|---|---|---|---|---|---|---|
| Gly | Ala | Phe | Cys | Ile | Pro | Leu | Tyr | Val | Pro | Tyr | Val | Leu | Thr | Gly | Arg |
| 1 | | | | 5 | | | | | 10 | | | | | 15 | |

| TGG | ACC | TTC | GGC | CGG | GGC | CTC | TGC | AAG | CTG | TGG | CTG | GTG | GTA | GAC | TAC | 96
| Trp | Thr | Phe | Gly | Arg | Gly | Leu | Cys | Lys | Leu | Trp | Leu | Val | Val | Asp | Tyr |
| | | | 20 | | | | 25 | | | | | 30 | | | |

| CTA | CTG | TGT | GCC | TCC | TCG | GTC | TTC | AAC | ATC | GTA | CTC | ATC | AGC | TAT | GAC | 144
| Leu | Leu | Cys | Ala | Ser | Ser | Val | Phe | Asn | Ile | Val | Leu | Ile | Ser | Tyr | Asp |
| | | 35 | | | | | 40 | | | | | 45 | | | |

| CGA | TTC | CTG | TCA | GTC | ACT | CGA | GCT | GTC | TCC | TAC | AGG | GCC | CAG | CAG | GGG | 192
| Arg | Phe | Leu | Ser | Val | Thr | Arg | Ala | Val | Ser | Tyr | Arg | Ala | Gln | Gln | Gly |
| | 50 | | | | | 55 | | | | | 60 | | | | |

| GAC | ACG | AGA | CGG | GCC | GTT | CGG | AAG | ATG | GCA | CTG | GTG | TGG | GTG | CTG | GCC | 240
| Asp | Thr | Arg | Arg | Ala | Val | Arg | Lys | Met | Ala | Leu | Val | Trp | Val | Leu | Ala |
| 65 | | | | | 70 | | | | | 75 | | | | | 80 |

| TTC | CTG | CTG | TAT | GGG | CCT | GCC | ATC | CTG | AGT | TGG | GAG | TAC | CTG | TCT | GGT | 288
| Phe | Leu | Leu | Tyr | Gly | Pro | Ala | Ile | Leu | Ser | Trp | Glu | Tyr | Leu | Ser | Gly |
| | | | | 85 | | | | | 90 | | | | | 95 | |

| GGC | AGT | TCC | ATC | CCC | GAG | GGC | CAC | TGC | TAT | GCT | GAG | TTC | TTC | TAC | AAC | 336
| Gly | Ser | Ser | Ile | Pro | Glu | Gly | His | Cys | Tyr | Ala | Glu | Phe | Phe | Tyr | Asn |
| | | | 100 | | | | 105 | | | | | 110 | | | |

| TGG | TAC | TTT | CTC | ATC | TCG | GCC | TCC | ACC | CTC | GAG | TTC | TTC | ACG | CCC | TTC | 384
| Trp | Tyr | Phe | Leu | Ile | Ser | Ala | Ser | Thr | Leu | Glu | Phe | Phe | Thr | Pro | Phe |
| | | 115 | | | | | 120 | | | | | 125 | | | |

| CTC | AGC | GTT | ACC | TTC | TTC | AAC | CTC | AGC | ATC | TAC | CTG | AAC | ATC | CAG | AGG | 432
| Leu | Ser | Val | Thr | Phe | Phe | Asn | Leu | Ser | Ile | Tyr | Leu | Asn | Ile | Gln | Arg |
| | 130 | | | | | 135 | | | | | 140 | | | | |

| CGC | ACC | CGC | CTT | CGG | CTT | GAT | GGG | GGC | CGT | GAG | GCT | GGC | CCA | GAA | CCC | 480
| Arg | Thr | Arg | Leu | Arg | Leu | Asp | Gly | Gly | Arg | Glu | Ala | Gly | Pro | Glu | Pro |
| 145 | | | | | 150 | | | | | 155 | | | | | 160 |

| CCA | CCA | GAT | GCC | CAG | CCC | TCG | CCA | CCT | CCA | GCT | CCC | CCC | AGC | TGC | TGG | 528
| Pro | Pro | Asp | Ala | Gln | Pro | Ser | Pro | Pro | Pro | Ala | Pro | Pro | Ser | Cys | Trp |
| | | | | 165 | | | | | 170 | | | | | 175 | |

| GGC | TGC | TGG | CCA | AAA | GGG | CAT | GGC | GAG | GCC | ATG | CCG | TTG | CAC | AGG | TAT | 576
| Gly | Cys | Trp | Pro | Lys | Gly | His | Gly | Glu | Ala | Met | Pro | Leu | His | Arg | Tyr |
| | | | 180 | | | | 185 | | | | | 190 | | | |

| GGG | GTG | GGT | GAG | GCA | GGC | CCT | GGT | GTT | GAG | GCT | GGG | GAG | GCT | GCC | CTC | 624
| Gly | Val | Gly | Glu | Ala | Gly | Pro | Gly | Val | Glu | Ala | Gly | Glu | Ala | Ala | Leu |
| | | | 195 | | | | 200 | | | | | 205 | | | |

| GGG | GGT | GGC | AGT | GGT | GGA | GGT | GCT | GCT | GCC | TCG | CCC | ACC | TCC | AGC | TCT | 672
| Gly | Gly | Gly | Ser | Gly | Gly | Gly | Ala | Ala | Ala | Ser | Pro | Thr | Ser | Ser | Ser |

```
                  210                         215                         220
GGC  AGC  TCC  TCA  AGG  GGC  ACT  GAG  AGG  CCA  CGC  TCA  CTC  AAA  AGG  GGC          720
Gly  Ser  Ser  Ser  Arg  Gly  Thr  Glu  Arg  Pro  Arg  Ser  Leu  Lys  Arg  Gly
225                      230                      235                      240

TCC  AAG  CCA  TCA  GCA  TCT  TCA  GCA  TCC  CTG  GAG  AAG  CGC  ATG  AAG  ATG          768
Ser  Lys  Pro  Ser  Ala  Ser  Ser  Ala  Ser  Leu  Glu  Lys  Arg  Met  Lys  Met
                    245                      250                      255

GTG  TCC  CAG  AGC  ATC  ACC  CAG  CGC  TTC  CGG  CTG  TCG  CGG  GAC  AAG  AAG          816
Val  Ser  Gln  Ser  Ile  Thr  Gln  Arg  Phe  Arg  Leu  Ser  Arg  Asp  Lys  Lys
               260                      265                      270

GTG  GCC  AAG  TCG  CTG  GCC  ATC  ATC  GTG  AGC  ATC  TTT  GGG  CTC  TGC  TGG          864
Val  Ala  Lys  Ser  Leu  Ala  Ile  Ile  Val  Ser  Ile  Phe  Gly  Leu  Cys  Trp
               275                      280                      285

GCG  CCG  TAC  ACG  CTC  CTA  ATG  ATC  ATC  CGA  GCT  GCT  TGC  CAT  GGC  CGC          912
Ala  Pro  Tyr  Thr  Leu  Leu  Met  Ile  Ile  Arg  Ala  Ala  Cys  His  Gly  Arg
          290                      295                      300

TGC  ATC  CCC  GAT  TAC  TGG  TAC  GAG  ACG  TCC  TTC  TGG  CTT  CTG  TGG  GCC          960
Cys  Ile  Pro  Asp  Tyr  Trp  Tyr  Glu  Thr  Ser  Phe  Trp  Leu  Leu  Trp  Ala
305                      310                      315                      320

AAC  TCG  GCC  GTC  AAC  CCC  GTC  CTC  TAC  CCA  CTG  TGC  CAC  TAC  AGC  TTC         1008
Asn  Ser  Ala  Val  Asn  Pro  Val  Leu  Tyr  Pro  Leu  Cys  His  Tyr  Ser  Phe
                    325                      330                      335

CGC  AGA  GCC  TTC  ACC  AAG  CTC  CTC  TGC  CCC  CAG  AAG  CTC  AAG  GTC  CAG         1056
Arg  Arg  Ala  Phe  Thr  Lys  Leu  Leu  Cys  Pro  Gln  Lys  Leu  Lys  Val  Gln
               340                      345                      350

CCC  CAC  GGC  TCC  CTG  GAG  CAG  TGC  TGG  AAG  TGAGCAGCTG  CCCCACCCTT               1106
Pro  His  Gly  Ser  Leu  Glu  Gln  Cys  Trp  Lys
          355                      360

CTGAGGCCAG  GCCCTTGTAC  TTGTTTGAGT  GGGCAGCCGG  AGCGTGGGCG  GGGCCCTGGT                 1166

CCATGCTCCG  CTCCAAATGC  CATGGCGGCC  TCTTAGATCA  TCAACCCCGC  AGTGGGGTAG                 1226

CATGGCAGGT  GGGCCAAGAG  CCCTAGTTGG  TGGAGCTAGA  GTGTGCTGGT  TAGCTCTGCC                 1286

GCCACATTCT  CCTTCACCAC  ACAGAAGAGA  CAATCCAGGA  GTCCCAGGCA  TGCCTTCCAC                 1346

CTACACACAC  ACACACACAC  ACACACACAC  ACACACCACA  GTGCAGTGCC  AGTGATGTCC                 1406

CCTTTTGCAT  ATTTAGTGGT  TGGTGTCCTC  CCTAATGCAA  ACCTCGGTGT  GTGCTCCCGG                 1466

CTCCGGCCCT  GGCAATGCGT  GCGTGCGCCC  TGCATGTGCT  CACACCCGCC  ACACACCCGC                 1526

CCGCCACACA  CTTGCAACAC  CTCCTCTCTC  CCAGAAGAGC  TGGGGACGAT  GCCCTTTGCT                 1586

GCCACTGTCT  CTTGCTTAAT  CCCAGAGCCT  GGCTCCTTAT  CCCCACTCT   CCCTTCAACT                 1646

CTGCCCCACA  AAGTGTCGAG  CGCCTCGGGA  AACTTGAAGC  TTCTCTGCTC  CTTCCACTCT                 1706

GGATGTTTTC  AGGAAGATGG  AGGAGAAGAA  AACACGTCTG  TGAACTTGAT  GTTCCTTGGA                 1766

TGTTTAATCA  AGAGAGACAA  AATTGCCGAG  GAGCTCGGGG  CTGGATTGGC  AGGTGTGGGC                 1826

TCCCACGCCC  TCCTCCCTCA  GTGCTGCAGC  TTCCGGCTGA  GCCGCGCCAG  CTGCTTCTGC                 1886

CTGCCCCGCC  CCCAGGCTTG  GGACGATGGC  CCTGCCCTGC  TTGCCCCGTC  TGTACAATCA                 1946

GAATTTGGGG  GTGGGTGGTT  ATGGGGTAGA  GCGGCTCTTC  ACTGTGCCCT  AAAGGTCCTG                 2006

AGGCTCACAG  GACAGTCAGC  AGGAGAGCAG  GCAGGCCCGC  GACACCTGGG  AGGAATGCTT                 2066

TGCCTCGTCC  TGTGTACTCA  CCTCAGGCTT  CTGCATGCTC  TGCTGCCCTT  GTGCCCTGGT                 2126

GTGCTGCCTC  TGCCAATGTG  AAAACACAAT  AAAGTGTATT  TTTTAAAAA  AAAAAAAAA                   2186

AAAAAAAAAA  AAAAAAAAAA  AAGGGCGGCC  GC                                                 2218
```

( 2 ) INFORMATION FOR SEQ ID NO:5:

( i ) SEQUENCE CHARACTERISTICS:

(A) LENGTH: 362 amino acids
(B) TYPE: amino acid
(D) TOPOLOGY: linear (ii) MOLECULE TYPE: protein (xi) SEQUENCE DESCRIPTION: SEQ ID NO:5:

| Gly | Ala | Phe | Cys | Ile | Pro | Leu | Tyr | Val | Pro | Tyr | Val | Leu | Thr | Gly | Arg |
|---|---|---|---|---|---|---|---|---|---|---|---|---|---|---|---|
| 1 | | | | 5 | | | | | 10 | | | | | 15 | |
| Trp | Thr | Phe | Gly | Arg | Gly | Leu | Cys | Lys | Leu | Trp | Leu | Val | Val | Asp | Tyr |
| | | | 20 | | | | | 25 | | | | | 30 | | |
| Leu | Leu | Cys | Ala | Ser | Ser | Val | Phe | Asn | Ile | Val | Leu | Ile | Ser | Tyr | Asp |
| | | 35 | | | | | 40 | | | | | 45 | | | |
| Arg | Phe | Leu | Ser | Val | Thr | Arg | Ala | Val | Ser | Tyr | Arg | Ala | Gln | Gln | Gly |
| | 50 | | | | | 55 | | | | | 60 | | | | |
| Asp | Thr | Arg | Arg | Ala | Val | Arg | Lys | Met | Ala | Leu | Val | Trp | Val | Leu | Ala |
| 65 | | | | | 70 | | | | | 75 | | | | | 80 |
| Phe | Leu | Leu | Tyr | Gly | Pro | Ala | Ile | Leu | Ser | Trp | Glu | Tyr | Leu | Ser | Gly |
| | | | | 85 | | | | | 90 | | | | | 95 | |
| Gly | Ser | Ser | Ile | Pro | Glu | Gly | His | Cys | Tyr | Ala | Glu | Phe | Phe | Tyr | Asn |
| | | | 100 | | | | | 105 | | | | | 110 | | |
| Trp | Tyr | Phe | Leu | Ile | Ser | Ala | Ser | Thr | Leu | Glu | Phe | Phe | Thr | Pro | Phe |
| | | 115 | | | | | 120 | | | | | 125 | | | |
| Leu | Ser | Val | Thr | Phe | Phe | Asn | Leu | Ser | Ile | Tyr | Leu | Asn | Ile | Gln | Arg |
| | 130 | | | | | 135 | | | | | 140 | | | | |
| Arg | Thr | Arg | Leu | Arg | Leu | Asp | Gly | Gly | Arg | Glu | Ala | Gly | Pro | Glu | Pro |
| 145 | | | | | 150 | | | | | 155 | | | | | 160 |
| Pro | Pro | Asp | Ala | Gln | Pro | Ser | Pro | Pro | Ala | Pro | Pro | Ser | Cys | Trp |
| | | | | 165 | | | | | 170 | | | | | 175 | |
| Gly | Cys | Trp | Pro | Lys | Gly | His | Gly | Glu | Ala | Met | Pro | Leu | His | Arg | Tyr |
| | | | 180 | | | | | 185 | | | | | 190 | | |
| Gly | Val | Gly | Glu | Ala | Gly | Pro | Gly | Val | Glu | Ala | Gly | Glu | Ala | Ala | Leu |
| | | 195 | | | | | 200 | | | | | 205 | | | |
| Gly | Gly | Gly | Ser | Gly | Gly | Gly | Ala | Ala | Ala | Ser | Pro | Thr | Ser | Ser | Ser |
| | 210 | | | | | 215 | | | | | 220 | | | | |
| Gly | Ser | Ser | Ser | Arg | Gly | Thr | Glu | Arg | Pro | Arg | Ser | Leu | Lys | Arg | Gly |
| 225 | | | | | 230 | | | | | 235 | | | | | 240 |
| Ser | Lys | Pro | Ser | Ala | Ser | Ser | Ala | Ser | Leu | Glu | Lys | Arg | Met | Lys | Met |
| | | | | 245 | | | | | 250 | | | | | 255 | |
| Val | Ser | Gln | Ser | Ile | Thr | Gln | Arg | Phe | Arg | Leu | Ser | Arg | Asp | Lys | Lys |
| | | | 260 | | | | | 265 | | | | | 270 | | |
| Val | Ala | Lys | Ser | Leu | Ala | Ile | Ile | Val | Ser | Ile | Phe | Gly | Leu | Cys | Trp |
| | | 275 | | | | | 280 | | | | | 285 | | | |
| Ala | Pro | Tyr | Thr | Leu | Leu | Met | Ile | Ile | Arg | Ala | Ala | Cys | His | Gly | Arg |
| | 290 | | | | | 295 | | | | | 300 | | | | |
| Cys | Ile | Pro | Asp | Tyr | Trp | Tyr | Glu | Thr | Ser | Phe | Trp | Leu | Leu | Trp | Ala |
| 305 | | | | | 310 | | | | | 315 | | | | | 320 |
| Asn | Ser | Ala | Val | Asn | Pro | Val | Leu | Tyr | Pro | Leu | Cys | His | Tyr | Ser | Phe |
| | | | | 325 | | | | | 330 | | | | | 335 | |
| Arg | Arg | Ala | Phe | Thr | Lys | Leu | Leu | Cys | Pro | Gln | Lys | Leu | Lys | Val | Gln |
| | | | 340 | | | | | 345 | | | | | 350 | | |
| Pro | His | Gly | Ser | Leu | Glu | Gln | Cys | Trp | Lys |
| | | 355 | | | | | 360 | | |

(2) INFORMATION FOR SEQ ID NO:6:

(i) SEQUENCE CHARACTERISTICS:
  (A) LENGTH: 1086 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..1086

(xi) SEQUENCE DESCRIPTION: SEQ ID NO:6:

| GGT | GCC | TTC | TGC | ATC | CCA | TTG | TAC | GTA | CCC | TAT | GTG | CTG | ACC | GGC | CGT | 48 |
| Gly | Ala | Phe | Cys | Ile | Pro | Leu | Tyr | Val | Pro | Tyr | Val | Leu | Thr | Gly | Arg | |
| 1 | | | | 5 | | | | | 10 | | | | | 15 | | |

| TGG | ACC | TTC | GGC | CGG | GGC | CTC | TGC | AAG | CTG | TGG | CTG | GTG | GTA | GAC | TAC | 96 |
| Trp | Thr | Phe | Gly | Arg | Gly | Leu | Cys | Lys | Leu | Trp | Leu | Val | Val | Asp | Tyr | |
| | | | 20 | | | | | 25 | | | | | 30 | | | |

| CTA | CTG | TGT | GCC | TCC | TCG | GTC | TTC | AAC | ATC | GTA | CTC | ATC | AGC | TAT | GAC | 144 |
| Leu | Leu | Cys | Ala | Ser | Ser | Val | Phe | Asn | Ile | Val | Leu | Ile | Ser | Tyr | Asp | |
| | | 35 | | | | | 40 | | | | | 45 | | | | |

| CGA | TTC | CTG | TCA | GTC | ACT | CGA | GCT | GTC | TCC | TAC | AGG | GCC | CAG | CAG | GGG | 192 |
| Arg | Phe | Leu | Ser | Val | Thr | Arg | Ala | Val | Ser | Tyr | Arg | Ala | Gln | Gln | Gly | |
| | 50 | | | | | 55 | | | | | 60 | | | | | |

| GAC | ACG | AGA | CGG | GCC | GTT | CGG | AAG | ATG | GCA | CTG | GTG | TGG | GTG | CTG | GCC | 240 |
| Asp | Thr | Arg | Arg | Ala | Val | Arg | Lys | Met | Ala | Leu | Val | Trp | Val | Leu | Ala | |
| 65 | | | | | 70 | | | | | 75 | | | | | 80 | |

| TTC | CTG | CTG | TAT | GGG | CCT | GCC | ATC | CTG | AGT | TGG | GAG | TAC | CTG | TCT | GGT | 288 |
| Phe | Leu | Leu | Tyr | Gly | Pro | Ala | Ile | Leu | Ser | Trp | Glu | Tyr | Leu | Ser | Gly | |
| | | | | 85 | | | | | 90 | | | | | 95 | | |

| GGC | AGT | TCC | ATC | CCC | GAG | GGC | CAC | TGC | TAT | GCT | GAG | TTC | TTC | TAC | AAC | 336 |
| Gly | Ser | Ser | Ile | Pro | Glu | Gly | His | Cys | Tyr | Ala | Glu | Phe | Phe | Tyr | Asn | |
| | | | 100 | | | | | 105 | | | | | 110 | | | |

| TGG | TAC | TTT | CTC | ATC | TCG | GCC | TCC | ACC | CTC | GAG | TTC | TTC | ACG | CCC | TTC | 384 |
| Trp | Tyr | Phe | Leu | Ile | Ser | Ala | Ser | Thr | Leu | Glu | Phe | Phe | Thr | Pro | Phe | |
| | | 115 | | | | | 120 | | | | | 125 | | | | |

| CTC | AGC | GTT | ACC | TTC | TTC | AAC | CTC | AGC | ATC | TAC | CTG | AAC | ATC | CAG | AGG | 432 |
| Leu | Ser | Val | Thr | Phe | Phe | Asn | Leu | Ser | Ile | Tyr | Leu | Asn | Ile | Gln | Arg | |
| | 130 | | | | | 135 | | | | | 140 | | | | | |

| CGC | ACC | CGC | CTT | CGG | CTT | GAT | GGG | GGC | CGT | GAG | GCT | GGC | CCA | GAA | CCC | 480 |
| Arg | Thr | Arg | Leu | Arg | Leu | Asp | Gly | Gly | Arg | Glu | Ala | Gly | Pro | Glu | Pro | |
| 145 | | | | | 150 | | | | | 155 | | | | | 160 | |

| CCA | CCA | GAT | GCC | CAG | CCC | TCG | CCA | CCT | CCA | GCT | CCC | CCC | AGC | TGC | TGG | 528 |
| Pro | Pro | Asp | Ala | Gln | Pro | Ser | Pro | Pro | Pro | Ala | Pro | Pro | Ser | Cys | Trp | |
| | | | | 165 | | | | | 170 | | | | | 175 | | |

| GGC | TGC | TGG | CCA | AAA | GGG | CAT | GGC | GAG | GCC | ATG | CCG | TTG | CAC | AGG | TAT | 576 |
| Gly | Cys | Trp | Pro | Lys | Gly | His | Gly | Glu | Ala | Met | Pro | Leu | His | Arg | Tyr | |
| | | | 180 | | | | | 185 | | | | | 190 | | | |

| GGG | GTG | GGT | GAG | GCA | GGC | CCT | GGT | GTT | GAG | GCT | GGG | GAG | GCT | GCC | CTC | 624 |
| Gly | Val | Gly | Glu | Ala | Gly | Pro | Gly | Val | Glu | Ala | Gly | Glu | Ala | Ala | Leu | |
| | | 195 | | | | | 200 | | | | | 205 | | | | |

| GGG | GGT | GGC | AGT | GGT | GGA | GGT | GCT | GCT | GCC | TCG | CCC | ACC | TCC | AGC | TCT | 672 |
| Gly | Gly | Gly | Ser | Gly | Gly | Gly | Ala | Ala | Ala | Ser | Pro | Thr | Ser | Ser | Ser | |
| | 210 | | | | | 215 | | | | | 220 | | | | | |

| GGC | AGC | TCC | TCA | AGG | GGC | ACT | GAG | AGG | CCA | CGC | TCA | CTC | AAA | AGG | GGC | 720 |
| Gly | Ser | Ser | Ser | Arg | Gly | Thr | Glu | Arg | Pro | Arg | Ser | Leu | Lys | Arg | Gly | |
| 225 | | | | | 230 | | | | | 235 | | | | | 240 | |

| TCC | AAG | CCA | TCA | GCA | TCT | TCA | GCA | TCC | TGA | GAA | GCG | CAT | G | AAG | ATG | 768 |
| Ser | Lys | Pro | Ser | Ala | Ser | Ser | Ala | Ser | Leu | Glu | Lys | Arg | Met | Lys | Met | |
| | | | | 245 | | | | | 250 | | | | | 255 | | |

| GTG | TCC | CAG | AGC | ATC | ACC | CAG | CGC | TTC | CGG | CTG | TCG | CGG | GAC | AAG | AAG | 816 |
| Val | Ser | Gln | Ser | Ile | Thr | Gln | Arg | Phe | Arg | Leu | Ser | Arg | Asp | Lys | Lys | |

|  |  |  | 260 |  |  |  | 265 |  |  |  | 270 |  |  |  |  |
|---|---|---|---|---|---|---|---|---|---|---|---|---|---|---|---|
| GTG | GCC | AAG | TCG | CTG | GCC | ATC | ATC | GTG | AGC | ATC | TTT | GGG | CTC | TGC | TGG | 864 |
| Val | Ala | Lys | Ser | Leu | Ala | Ile | Ile | Val | Ser | Ile | Phe | Gly | Leu | Cys | Trp |
|  |  | 275 |  |  |  |  | 280 |  |  |  |  | 285 |  |  |  |
| GCG | CCG | TAC | ACG | CTC | CTA | ATG | ATC | ATC | CGA | GCT | GCT | TGC | CAT | GGC | CGC | 912 |
| Ala | Pro | Tyr | Thr | Leu | Leu | Met | Ile | Ile | Arg | Ala | Ala | Cys | His | Gly | Arg |
|  |  | 290 |  |  |  |  | 295 |  |  |  |  | 300 |  |  |  |
| TGC | ATC | CCC | GAT | TAC | TGG | TAC | GAG | ACG | TCC | TTC | TGG | CTT | CTG | TGG | GCC | 960 |
| Cys | Ile | Pro | Asp | Tyr | Trp | Tyr | Glu | Thr | Ser | Phe | Trp | Leu | Leu | Trp | Ala |
| 305 |  |  |  |  | 310 |  |  |  |  | 315 |  |  |  |  | 320 |
| AAC | TCG | GCC | GTC | AAC | CCC | GTC | CTC | TAC | CCA | CTG | TGC | CAC | TAC | AGC | TTC | 1008 |
| Asn | Ser | Ala | Val | Asn | Pro | Val | Leu | Tyr | Pro | Leu | Cys | His | Tyr | Ser | Phe |
|  |  |  |  | 325 |  |  |  |  | 330 |  |  |  |  | 335 |  |
| CGC | AGA | GCC | TTC | ACC | AAG | CTC | CTC | TGC | CCC | CAG | AAG | CTC | AAG | GTC | CAG | 1056 |
| Arg | Arg | Ala | Phe | Thr | Lys | Leu | Leu | Cys | Pro | Gln | Lys | Leu | Lys | Val | Gln |
|  |  |  | 340 |  |  |  |  | 345 |  |  |  |  | 350 |  |  |
| CCC | CAC | GGC | TCC | CTG | GAG | CAG | TGC | TGG | AAG |  |  |  |  |  |  | 1086 |
| Pro | His | Gly | Ser | Leu | Glu | Gln | Cys | Trp | Lys |  |  |  |  |  |  |
|  |  | 355 |  |  |  |  | 360 |  |  |  |  |  |  |  |  |

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Thr | Ala | Val | Leu | Ala | Ala | Leu | Met | Ala | Leu | Leu | Ile | Val | Ala | Thr | Val |
|---|---|---|---|---|---|---|---|---|---|---|---|---|---|---|---|
| 1 |  |  |  | 5 |  |  |  |  | 10 |  |  |  |  | 15 |  |
| Leu | Gly | Asn | Ala | Leu | Val | Met | Leu | Ala | Phe |  |  |  |  |  |  |
|  |  |  | 20 |  |  |  |  | 25 |  |  |  |  |  |  |  |

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Leu | Leu | Asn | Leu | Ala | Ile | Ser | Asp | Phe | Leu | Val | Gly | Ala | Phe | Cys | Ile |
|---|---|---|---|---|---|---|---|---|---|---|---|---|---|---|---|
| 1 |  |  |  | 5 |  |  |  |  | 10 |  |  |  |  | 15 |  |
| Pro | Leu | Tyr |  |  |  |  |  |  |  |  |  |  |  |  |  |

( 2 ) INFORMATION FOR SEQ ID NO:9:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Leu | Trp | Leu | Val | Val | Asp | Tyr | Leu | Leu | Cys | Thr | Ser | Ser | Ala | Phe | Asn |
|---|---|---|---|---|---|---|---|---|---|---|---|---|---|---|---|
| 1 |  |  |  | 5 |  |  |  |  | 10 |  |  |  |  | 15 |  |
| Ile | Val | Leu | Ile | Ser | Tyr |  |  |  |  |  |  |  |  |  |  |
|  |  |  | 20 |  |  |  |  |  |  |  |  |  |  |  |  |

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ala  Val  Arg  Lys  Met  Leu  Leu  Val  Trp  Val  Leu  Ala  Phe  Leu  Leu  Tyr
 1              5                        10                       15
Gly  Pro  Ala  Ile  Leu  Ser  Trp
              20
```

( 2 ) INFORMATION FOR SEQ ID NO:11:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Tyr  Phe  Leu  Ile  Thr  Ala  Ser  Thr  Leu  Glu  Phe  Phe  Thr  Pro  Phe  Leu
 1              5                        10                       15
Ser  Val  Thr  Phe  Phe  Asn  Leu
              20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Leu  Ala  Val  Ile  Val  Ser  Ile  Phe  Gly  Leu  Cys  Trp  Ala  Pro  Tyr  Thr
 1              5                        10                       15
Leu  Leu  Met  Ile  Ile
              20
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Thr  Ser  Phe  Trp  Leu  Leu  Trp  Ala  Asn  Ser  Ala  Val  Asn  Pro  Val  Leu
 1              5                        10                       15
Tyr  Pro  Leu  Cys  His
              20
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Gly Ala Phe Cys Ile Pro Leu Tyr
 1                5

( 2 ) INFORMATION FOR SEQ ID NO:15:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

Leu Trp Leu Val Val Asp Tyr Leu Leu Cys Ala Ser Ser Val Phe Asn
 1                5                    10                      15

Ile Val Leu Ile Ser Tyr
                20

( 2 ) INFORMATION FOR SEQ ID NO:16:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Ala Val Arg Lys Met Ala Leu Val Trp Val Leu Ala Phe Leu Leu Tyr
 1                5                    10                      15

Gly Pro Ala Ile Leu Ser Trp
                20

( 2 ) INFORMATION FOR SEQ ID NO:17:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

Tyr Phe Leu Ile Ser Ala Ser Thr Leu Glu Phe Phe Thr Pro Phe Leu
 1                5                    10                      15

Ser Val Thr Phe Phe Asn Leu
                20

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Leu Ala Ile Ile Val Ser Ile Phe Gly Leu Cys Trp Ala Pro Tyr Thr
 1                5                    10                      15

Leu Leu Met Ile Ile
                20

( 2 ) INFORMATION FOR SEQ ID NO:19:

( i ) SEQUENCE CHARACTERISTICS:
 ( A ) LENGTH: 21 amino acids
 ( B ) TYPE: amino acid
 ( D ) TOPOLOGY: linear ( i i ) MOLECULE TYPE: protein ( x i ) SEQUENCE DESCRIPTION: SEQ ID NO:19:

Thr Ser Phe Trp Leu Leu Trp Ala Asn Ser Ala Val Asn Pro Val Leu
 1               5                   10                  15

Tyr Pro Leu Cys His
            20

( 2 ) INFORMATION FOR SEQ ID NO:20:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:20:

CCTGCGGGGC CATGGAG                                                    17

( 2 ) INFORMATION FOR SEQ ID NO:21:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:21:

GTGGCCCACC AGAGCCT                                                    17

( 2 ) INFORMATION FOR SEQ ID NO:22:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:22:

CAGCCACGCC TCTCTCA                                                    17

( 2 ) INFORMATION FOR SEQ ID NO:23:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:23:

TGAGCAGCTG CCCCAC                                                     16

( 2 ) INFORMATION FOR SEQ ID NO:24:

( i ) SEQUENCE CHARACTERISTICS:

(A) LENGTH: 16 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:24:

CTGAGGCCAG GCCCTT 16

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:25:

CAAGAACCCT TTAAGCCAAG 20

(2) INFORMATION FOR SEQ ID NO:26:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

GAAGAAGGTA ACGCTGAGGA 20

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:27:

CAGAACCCCC ACCAGATGCC 20

(2) INFORMATION FOR SEQ ID NO:28:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:28:

TAGTGGCACA GTGGGTAGAG 20